United States Patent
Wu et al.

(10) Patent No.: US 10,889,595 B2
(45) Date of Patent: Jan. 12, 2021

(54) [1,3]THIAZIN-2-AMINE COMPOUND, APPLICATION, AND PHARMACEUTICAL COMPOSITION

(71) Applicant: TETRANOV PHARMACEUTICAL CO., LTD., Zhengzhou (CN)

(72) Inventors: Yusheng Wu, Zhengzhou (CN); Apeng Liang, Zhengzhou (CN); Chengshan Niu, Zhengzhou (CN); Yang Geng, Zhengzhou (CN); Jingya Li, Zhengzhou (CN)

(73) Assignee: TETRANOV PHARMACEUTICAL CO., LTD., Zhengzhou (CN)

( * ) Notice: Subject to any disclaimer, the term of this patent is extended or adjusted under 35 U.S.C. 154(b) by 12 days.

(21) Appl. No.: 16/473,070

(22) PCT Filed: Dec. 14, 2017

(86) PCT No.: PCT/CN2017/116031
§ 371 (c)(1),
(2) Date: Jun. 24, 2019

(87) PCT Pub. No.: WO2018/121267
PCT Pub. Date: Jul. 5, 2018

(65) Prior Publication Data
US 2019/0330236 A1     Oct. 31, 2019

(30) Foreign Application Priority Data
Dec. 26, 2016 (CN) .......................... 2016 1 1219244

(51) Int. Cl.
| | | |
|---|---|---|
| A61K 31/542 | (2006.01) | |
| A61P 3/04 | (2006.01) | |
| A61P 3/10 | (2006.01) | |
| A61P 25/28 | (2006.01) | |
| C07D 471/04 | (2006.01) | |
| C07D 513/04 | (2006.01) | |

(52) U.S. Cl.
CPC ................... C07D 513/04 (2013.01)

(58) Field of Classification Search
CPC ........... A61K 31/542; A61P 3/04; A61P 3/10; A61P 25/28; C07D 471/04; C07D 513/04
See application file for complete search history.

(56) References Cited

U.S. PATENT DOCUMENTS

| | | |
|---|---|---|
| 2011/0207723 A1 | 8/2011 | Motoki et al. |
| 2013/0053373 A1 | 3/2013 | Brodney et al. |

FOREIGN PATENT DOCUMENTS

| | | |
|---|---|---|
| EP | 2511269 A1 | 10/2012 |
| WO | 2005058311 A1 | 6/2005 |
| WO | 2005097767 A1 | 10/2005 |
| WO | 2006041404 A1 | 4/2006 |
| WO | 2006/138264 A2 | 12/2006 |
| WO | 2008133273 A1 | 11/2008 |
| WO | 2009/091016 A1 | 7/2009 |
| WO | 2010038686 A1 | 4/2010 |
| WO | 2011/009898 A1 | 1/2011 |
| WO | 2011071109 A1 | 6/2011 |
| WO | 2012020848 A1 | 2/2012 |
| WO | 2012087237 A1 | 6/2012 |
| WO | 2012156284 A1 | 11/2012 |
| WO | 2013164730 A1 | 11/2013 |
| WO | 2014045162 A1 | 3/2014 |
| WO | 2014059185 A1 | 4/2014 |
| WO | 2014091325 A1 | 6/2014 |
| WO | 2014204730 A1 | 12/2014 |
| WO | 2016024010 A1 | 2/2016 |
| WO | 2016043966 A1 | 3/2016 |

OTHER PUBLICATIONS

International Search Report in International Application No. PCT/CN2017/116031, dated Feb. 26, 2018.
Written Opinion of the International Search Authority in International Application No. PCT/CN2017/116031, dated Feb. 26, 2018.
H. Braak, et al., "Neuropathological stageing of Alzheimer-related changes", Acta Neuropathol (1991), 82:239-259.
Susan J. Tyler, et al., "α-and ?-secretase: profound changes in Alzheimer's disease", Biochemical and Biophysical Research Communications 299 (2002), 373-376.
World Health Organization, "Call for Action by the participants in the First WHO Ministerial Conference on Global Action Against Dementia (Geneva, Mar. 16-17, 2015)".

(Continued)

*Primary Examiner* — Brenda L Coleman
(74) *Attorney, Agent, or Firm* — Ladas & Parry LLP

(57) ABSTRACT

The present invention is directed to a [1,3]thiazin-2-amine compound, an application and a pharmaceutical composition, belongs to the field of BACE inhibitors. The [1,3]thiazin-2-amine compound is a compound represented by formula (I) or a pharmaceutically acceptable salt, stereoisomer, solvate or prodrug thereof. The compound has a good inhibitory effect on BACE and can be used in preparing a medicament for treating a neurodegenerative disease, such as Alzheimer's disease.

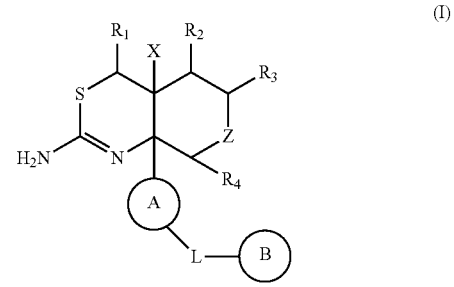

(I)

14 Claims, No Drawings

(56) References Cited

OTHER PUBLICATIONS

Gopal Thinakaran, et al., "Amyloid Precursor Protein Trafficking, Processing, and Function", J. Biol. Chem., Oct. 31, 2008, vol. 283, No. 44, 29615-29619.
Huaibin Cai, et al., "BACE1 is the major β-secretase for generation of Aβ peptides by neurons", Nature Neuroscience, vol. 4, No. 3, 2001, 233-234.
Liesi E. Hebert, ScD, et al., "Alzheimer disease in the United States (2010-2050) estimated using the 2010 census", Neurology 80, 2013, 1778-1783.
Eileen McGowan, et al., "Aβ42 Is Essential for Parenchymal and Vascular Amyloid Deposition in Mice", Neuron, vol. 47, 2005, 191-199.
Dennis J. Selkoe, "Alzheimer's Disease: Genes, Proteins, and Therapy", Physiological Reviews vol. 81, No. 2, 2001, 741-766.
Robert Vassar, et al., "β-Secretase Cleavage of Alzheimer's Amyloid Precursor Protein by the Transmembrane Aspartic Protease BACE", Science, vol. 286, 1999, 735-741.
Kwasi G. Mawuenyega, et al., "Decreased Clearance of CNS β-Amyloid in Alzheimer's Disease", Science, vol. 330, 2010, 1774.
Jason Greenwald, et al., "Biology of Amyloid: Structure, Function, and Regulation", Structure 18, 2010, 1244-1260.
English translation of the abstract of WO2008133273A1, 2008.
English translation of the abstract of WO2010038686A1, 2010.
English translation of the abstract of WO2011071109A1, 2011.

[1,3]THIAZIN-2-AMINE COMPOUND, APPLICATION, AND PHARMACEUTICAL COMPOSITION

RELATED APPLICATION

This application is an application under 35 U.S.C. 371 of International Application No. PCT/CN2017/116031 flied on 14 Dec. 2017, which claims priority from Chinese Application No. 201611219244.4 filed on 26 Dec. 2016, the disclosures of which are incorporated in their entirety by reference herein.

TECHNICAL FIELD

The present invention discloses a [1,3]thiazin-2-amine compound, as well as the use and the pharmaceutical composition thereof.

BACKGROUND OF THE INVENTION

Alzheimer's disease (AD) is a progressive neurodegenerative disease, and a primary cause inducing senile dementia. According to the research made by World Health Organization (WHO), nowadays, there are about 47.5 million patients with senile dementia in the world, and the medical fees for every year have already reached 200 billions of dollars. Considering that therapy of AD is only limited to the symptomatic treatment drugs with poor curative effect now, the total number of AD patients is estimated to reach 75 millions in 2030 and 135 millions in 2050, while the treatment costs will reach 1200 billions of dollars, and thus AD will become a major disease threatening human health (Neurology 2013, 80, 1778-1783; Dementia, Fact Sheet 362, World Health Organization: Geneva, 2015). Currently, only 5 drugs have been approved for symptomatic treatment of Alzheimer's disease, but the therapeutic effect is very poor, and none of the drugs can reverse the progession of AD. Thus, there is an urgent need for developing drugs can effectively suppress or reverse Alzheimer's disease.

As the deeping of research, scientists have found that the primary cause developing AD is NFTs (neurofibrillary tangles) formed by the extracellular abnormal deposition of β-amyloid protein in neurons and the abnormal phosphorylation of Tau protein, that in turn leads to the nerve degeneration and loss of its function (Acta Neuropathol. 1991, 82, 239-259). Clinically, AD is characterized by generalized dementia behaviors mainly including aphasia, apraxia, agnosia, visuospatial skill impairment, executive dysfunction, as well as personality and behavior change, etc. Research indicated that the deposition of Aβ-amyloid is caused by hydrolysis of β amyloid precursor protein (APP) under the action of a series of proteases. APP is a transmembrane protein, belongs to type I integral membrane glycoprotein, whose gene is consisted of 19 exons. The transcription products of APP gene include at least 8 isomers due to different splicing patterns, in which APP695, APP751 and APP770 are the main expression forms (Prog Clin Biol Res., 1989, 317, 971-984). Under the action of secretase, APP can be cleaved by two different pathways: the amyloidogenic pathway producing Aβ and the nonamyloidogenic pathway not producing Aβ. When the balance of both pathways is broken or the clearance of amyloid is damaged, the deposition of β-amyloid protein and the formation of plaques would occur (J. Biol. Chem. 2008, 283, 29615-29619; Science 2010, 330, 1774). Amongst, APP can be hydrolyzed by α-secretase in extracellular region and closer to the membrane (17 site of Aβ) of the APP and produce the soluble molecule sAPPα and the transmembrane segment αCTF (Biochem Biophys Res Commun, 2002, 299, 373-376). αCTF can further be hydrolyzed by γ-secretase to form p83 fragment. This is the nonamyloidogenic pathway for APP hydrolysis. The extracellular region of βAPP can firstly be hydrolysed by β-secretase at position 1 or 11 of Aβ, and the resultant transmembrance fragment βCTF can further be hydrolysed within membrane bilayers by γ-secretase, forming Aβ40 or Aβ42 (Nature nueroscience, 2001, 4(3), 233-234; Structure 2010, 18, 1244-1260), and this pathway is called as the amyloidogenic pathway. Aβ40 or 42 is secreted to the outside of cells, and goes through a series of fibering processes, and finally forms the amyloid precipitation. In the amyloid precipitation, Aβ42 has neurotoxicity and the hydrophobic interaction is stronger, and is more liable to aggregate (Neuron, 2005, 47191-199), it is thus considered as the main cause of forming the amyloid precipitation. After the amyloid precipitation, it can rapidly bind with microglia expressing surface antigens (such as CD45, HLA-DR), and be surrounded by activated astrocytes, to form senile plaques (microglias are usually located in the core area of senile plaque amyloids, and astrocytes surround them) (Physio. Rev., 2001, 81(2), 742-760). Since BACE (β-site amyloid precursor protein cleaving enzyme) includes β-site amyloid precursor protein cleaving enzyme-1 (BACE1) and the cognate BACE2, which is a protease related to the formation of β amyloid protein, and by now, the role of BACE1 in the formation of β amyloid protein has already been determined, but the role of BACE2 is still not confirmed (Science, 1999, 286, 735-741). Thus, inhibition of BACE1 is expected to suppress the formation of amyloid plaque, and finally alleviate or reverse the progression of the disease. Consequently, the drug development, targeting the inhibition of BACE for reducing the deposition of β-amyloid protein, has already made a great progress by far. Up to now, there are several clinical drugs and lots of patents and literatures, and the patents are as follows: WO2005058311, WO2005097767, WO2006041404, WO2008133273, WO2010038686, US2011/0207723, US2013/0053373, WO2013164730, WO2014045162, WO2014091325, WO2012020848, WO2014204730, WO2014059185, WO2012156284, WO2011071109, WO2012087237, WO2016024010, WO2016043996 etc.

Content of the Invention

The object of the present invention is to provide a [1,3]thiazin-2-amine compound, as shown by formula (I), or a pharmaceutically acceptable salt, stereoisomer, solvate or prodrug thereof:

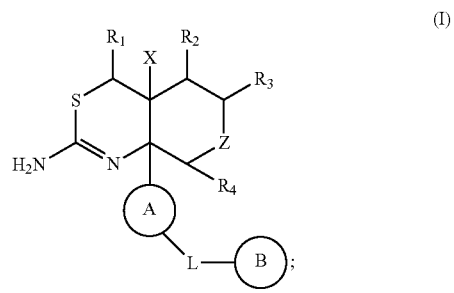

in formula (I), A is $C_{6-14}$ aryl, or $C_{6-14}$ aryl substituted by 1~4 substituents, or 5~6 membered heteroaryl, or 5~6 membered heteroaryl substituted by 1~4 substituents, or 9~10 membered benzo-fused heteroaryl, or 9~10 membered benzo-fused heteroaryl substituted by 1~4 substituents; said substituents are optionally selected from Group 1;

L is a single bond, oxygen atom, sulfur atom, —NR$_5$—, —NR$_5$CO—, —NR$_5$COR$_6$—, —NR$_5$CONR$_5$—, —NR$_5$COO—, —NR$_5$SO$_2$—, —NR$_5$SO—, or C$_{1-6}$ alkylene, or C$_{1-6}$ alkylene substituted by 1~3 substituents, or C$_{2-6}$ alkenylene, or C$_{2-6}$ alkenylene substituted by 1~3 substituents, or C$_{2-6}$ alkynylene, or C$_{2-6}$ alkynylene substituted by 1~3 substituents; wherein, R$_5$ is hydrogen atom, or C$_{1-6}$ alkyl, or C$_{1-6}$ alkyl substituted by 1~3 substituents; R$_6$ is C$_{1-6}$ alkyl, or C$_{1-6}$ alkyl substituted by 1~3 substituents; said substituents are optionally selected from Group 1;

B is C$_{1-6}$ alkyl, or C$_{1-6}$ alkyl substituted by 1~3 substituents, or C$_{3-8}$ cycloalkyl, or C$_{3-8}$ cycloalkyl substituted by 1~3 substituents, or C$_{6-14}$ aryl, or C$_{6-14}$ aryl substituted by 1~4 substituents, or 5~10 membered heteroaryl, or 5~10 membered heteroaryl substituted by 1~4 substituents; said substituents are optionally selected from Group 1;

R$_1$, R$_2$, and R$_4$ are independently from each other hydrogen atom, halogen atom, hydroxyl, amino, alkylamino, or C$_{1-6}$ alkyl, or C$_{1-6}$ alkyl substituted by 1~3 substituents, or C$_{1-6}$ alkoxyl, or C$_{1-6}$ alkoxyl substituted by 1~3 substituents, or 3~10 membered carbocyclic group, or 3~10 membered carbocyclic group substituted by 1~3 substituents, or C$_{6-14}$ aryl, or C$_{6-14}$ aryl substituted by 1~4 substituents, or 5~10 membered heteroaryl, or 5~10 membered heteroaryl substituted by 1~4 substituents; said substituents are optionally selected from Group 1;

R$_3$ is hydrogen atom, halogen atom, hydroxyl, amino, alkylamino, or C$_{1-6}$ alkyl, or C$_{1-6}$ alkyl substituted by 1~3 substituents, or C$_{1-6}$ alkoxyl, or C$_{1-6}$ alkoxyl substituted by 1~3 substituents, or 3~10 membered carbocyclic group, or 3~10 membered carbocyclic group substituted by 1~3 substituents, or C$_{6-14}$ aryl, or C$_{6-14}$ aryl substituted by 1~4 substituents, or 5~10 membered heteroaryl, or 5~10 membered heteroaryl substituted by 1~4 substituents; said substituents are optionally selected from Group 1;

Z is O, S, sulfoxide, sulfone, or —NR$_7$—, or C$_{3-8}$ cycloalkyl, or C$_{3-8}$ cycloalkyl substituted by 1~3 substituents, or C$_{1-6}$ alkoxylcarbonyl, or C$_{1-6}$ alkoxylcarbonyl substituted by 1~3 substituents, or C$_{6-14}$ aryloxycarbonyl, or C$_{6-14}$ aryloxycarbonyl substituted by 1~4 substituents, or C$_{1-6}$ alkoxylsulfonyl, or C$_{1-6}$ alkoxylsulfonyl substituted by 1~3 substituents, or C$_{6-14}$ aryloxysulfonyl, or C$_{6-14}$ aryloxysulfonyl substituted by 1~3 substituents, or C$_{6-14}$ aryl, or C$_{6-14}$ aryl substituted by 1~4 substituents, or 5~10 membered heteroaryl, or 5~10 membered heteroaryl substituted by 1~4 substituents; wherein R$_7$ is hydrogen atom, or C$_{1-6}$ alkyl, or C$_{1-6}$ alkyl substituted by 1~3 substituents, or C$_{6-14}$ aryl, or C$_{6-14}$ aryl substituted by 1~4 substituents, or 5-10 membered heteroaryl, or 5~10 membered heteroaryl substituted by 1~4 substituents; said substituents are optionally selected from Group 1;

Group 1 is hydrogen atom, halogen atom, hydroxyl, amino, cyano, amido, sulfonamido, difluoromethyl, trifluoromethyl, trifluoromethoxyl, C$_{1-6}$ alkylthio, C$_{1-6}$ alkoxyl, C$_{6-14}$ aryl, C$_{6-14}$ aryloxy, C$_{6-14}$ aryloxycarbonyl, C$_{6-14}$ arylcarbonyl, C$_{3-8}$ cycloalkyloxycarbonyl, C$_{3-8}$ cycloalkyl, C$_{3-8}$ cycloalkylthio, C$_{1-6}$ alkyl, C$_{1-6}$ alkylamino, C$_{1-6}$ alkylcarbonyl, C$_{2-6}$ alkenyl, C$_{2-6}$ alkynyl, 5~10 membered heteroaryl, or 5~10 membered heteroarylcarbonyl;

X is F, Cl, Br, or I, or C$_{1-4}$ alkyl, or C$_{1-4}$ alkyl substituted by 1~4 substituents; said substituents are optionally selected from Group 1;

The structure of formula (I) contains L and B, or may not contain L and B.

Further, the present invention provides a [1,3]thiazin-2-amine compound, as shown by formula (II), or a pharmaceutically acceptable salt, stereoisomer, solvate or prodrug thereof:

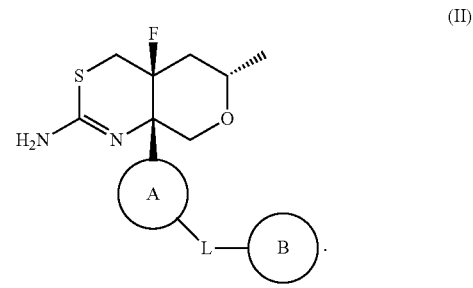

(II)

In formula (II), A is C$_{6-14}$ aryl, or C$_{6-14}$ aryl substituted by 1~4 substituents, or 5~6 membered heteroaryl, or 5~6 membered heteroaryl substituted by 1~4 substituents, or 9~10 membered benzo-fused heteroaryl, or 9~10 membered benzo-fused heteroaryl substituted by 1~4 substituents; said substituents are optionally selected from Group 1;

L is a single bond, oxygen atom, sulfur atom, —NR$_5$—, —NR$_5$CO—, —NR$_5$COR$_6$—, —NR$_5$CONR$_5$—, —NR$_5$COO—, —NR$_5$SO$_2$—, —NR$_5$SO—, or C$_{1-6}$ alkylene, or C$_{1-6}$ alkylene substituted by 1~3 substituents, or C$_{2-6}$ alkenylene, or C$_{2-6}$ alkenylene substituted by 1~3 substituents, or C$_{2-6}$ alkynylene, or C$_{2-6}$ alkynylene substituted by 1~3 substituents; wherein, R$_5$ is hydrogen atom, or C$_{1-6}$ alkyl, or C$_{1-6}$ alkyl substituted by 1~3 substituents; R$_6$ is C$_{1-6}$ alkyl, or C$_{1-6}$ alkyl substituted by 1~3 substituents; said substituents are optionally selected from Group 1;

B is C$_{1-6}$ alkyl, or C$_{1-6}$ alkyl substituted by 1~3 substituents, or C$_{3-8}$ cycloalkyl, or C$_{3-8}$ cycloalkyl substituted by 1~3 substituents, or C$_{6-14}$ aryl, or C$_{6-14}$ aryl substituted by 1~4 substituents, or 5~10 membered heteroaryl, or 5~10 membered heteroaryl substituted by 1~4 substituents; said substituents are optionally selected from Group 1;

Group 1 is hydrogen atom, halogen atom, hydroxyl, amino, cyano, amido, sulfonamido, difluoromethyl, trifluoromethyl, trifluoromethoxyl, C$_{1-6}$ alkylthio, C$_{1-6}$ alkoxyl, C$_{6-14}$ aryl, C$_{6-14}$ aryloxy, C$_{6-14}$ aryloxycarbonyl, C$_{6-14}$ arylcarbonyl, C$_{3-8}$ cycloalkyloxycarbonyl, C$_{3-8}$ cycloalkyl, C$_{3-8}$ cycloalkylthio, C$_{1-6}$ alkyl, C$_{1-6}$ alkylamino, C$_{1-6}$ alkylcarbonyl, C$_{2-6}$ alkenyl, C$_{2-6}$ alkynyl, 5~10 membered heteroaryl, or 5~10 membered heteroarylcarbonyl;

The structure of formula (II) contains L and B, or may not contain L and B.

Preferably, A is phenyl, or phenyl substituted by 1~4 substituents, or 5~6 membered heteroaryl, or 5~6 membered heteroaryl substituted by 1~4 substituents; said substituents are optionally selected from the group consisting of halogen atom, amino, cyano, difluoromethyl, trifluoromethyl, trifluoromethoxyl, C$_{1-6}$ alkoxyl, C$_{1-6}$ alkyl, C$_{2-6}$ alkynyl, and C$_{1-6}$ alkylamino.

L is a single bond, or oxygen atom, —NH—, or —NHCO—, or —NR$_5$SO$_2$—; B is 5~6 membered heteroaryl, or 5~6 membered heteroaryl substituted by 1~4 substituents; wherein, R$_5$ is hydrogen atom, or C$_{1-6}$ alkyl, or C$_{1-6}$ alkyl substituted by 1~3 substituents; said substituents are optionally selected from the group consisting of halogen atom, amino, cyano, difluoromethyl, trifluoromethyl, trifluoromethoxyl, C$_{1-6}$ alkoxyl, C$_{1-6}$ alkyl, C$_{2-6}$ alkynyl, and C$_{1-6}$ alkylamino.

The [1,3]thiazin-2-amine compound can be selected from the following compounds:
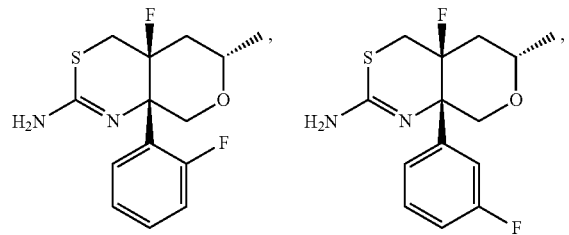
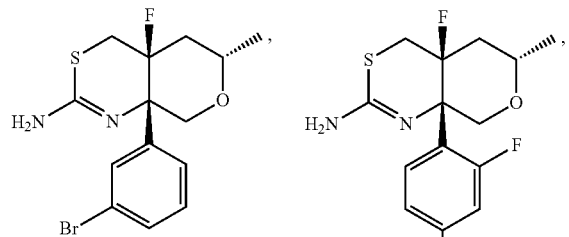
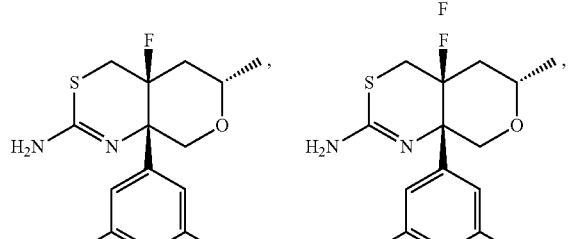
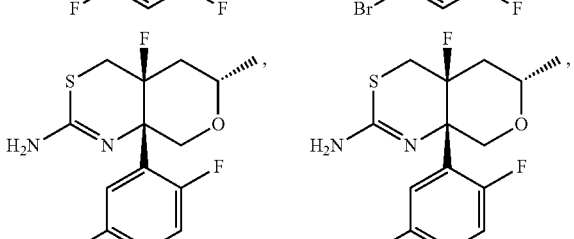
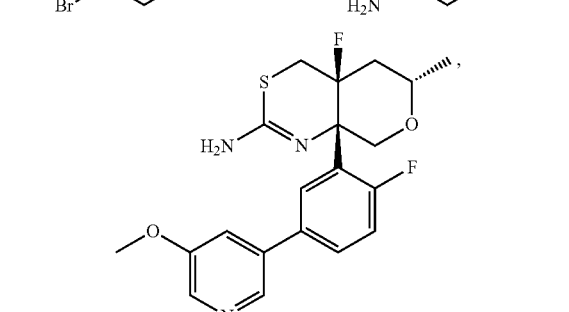
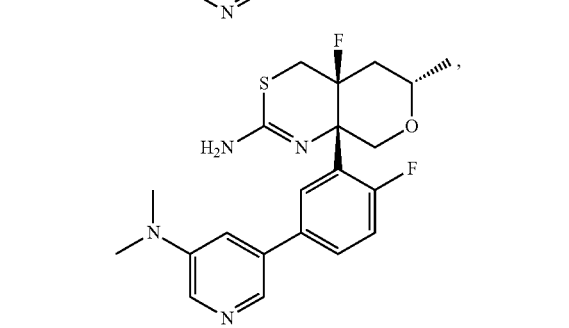
-continued
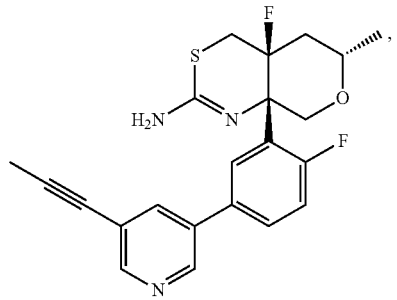
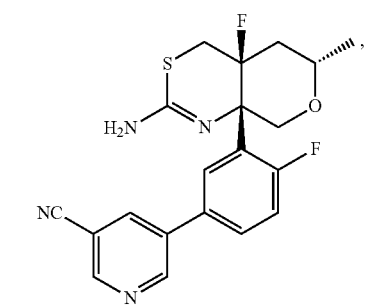
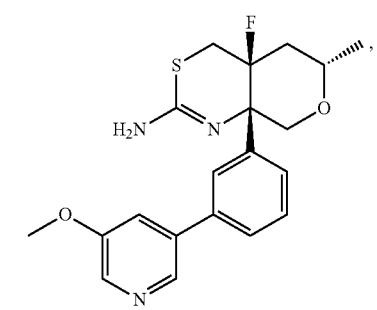
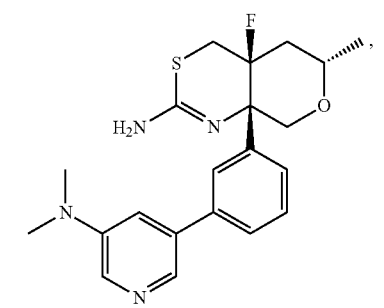
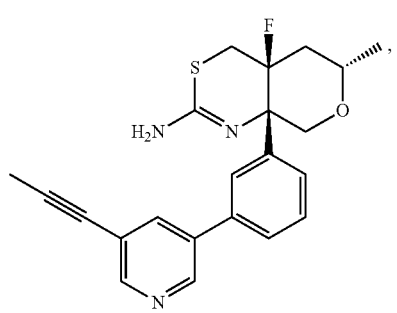

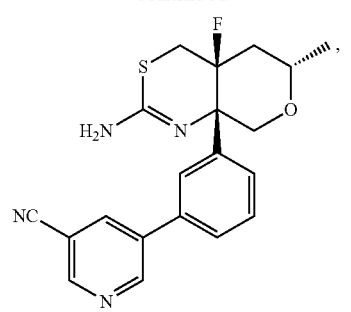
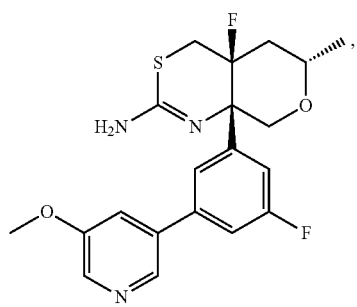
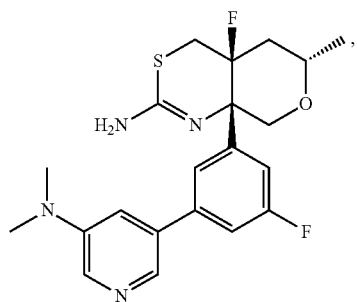
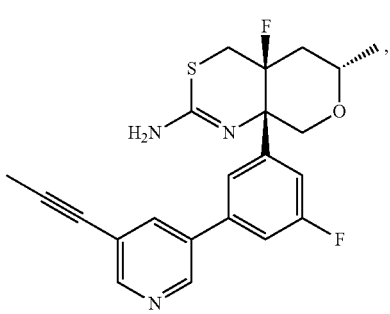
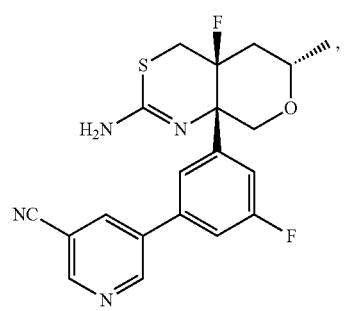
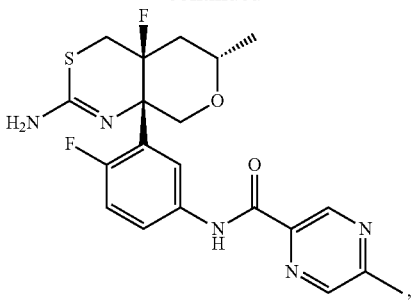
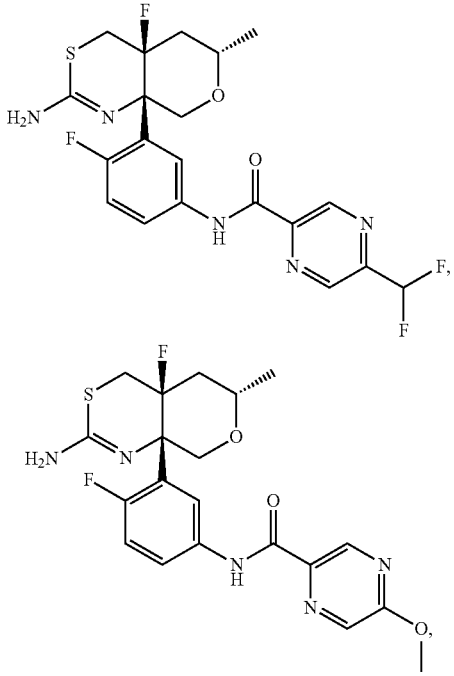
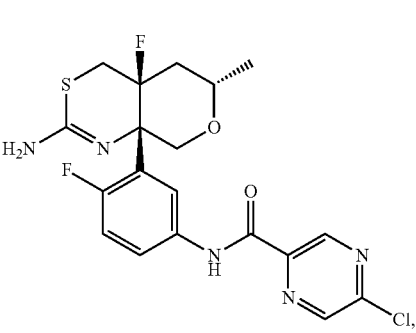
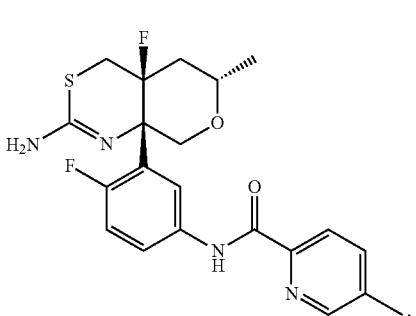

-continued
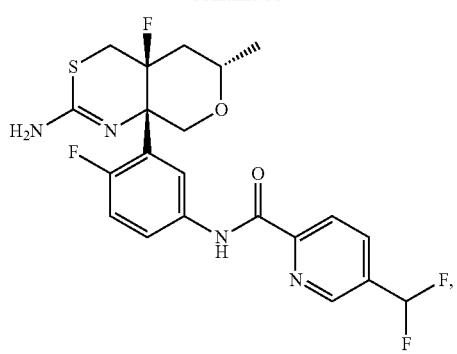
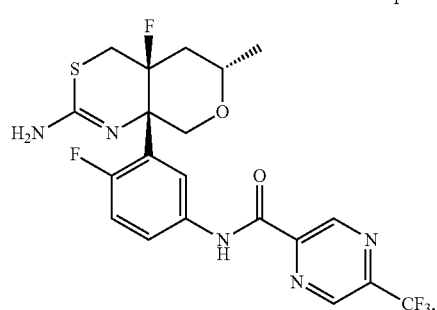
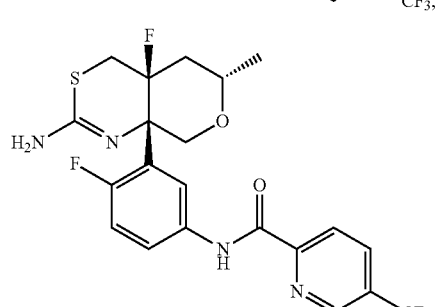
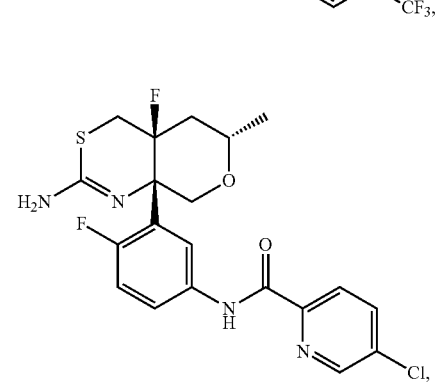
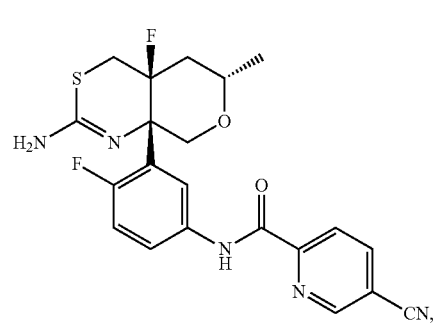
-continued
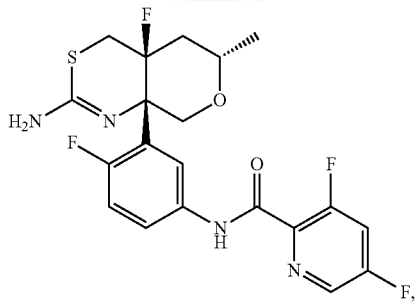
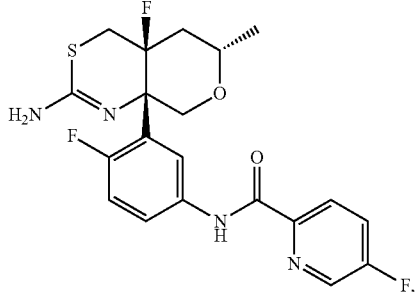
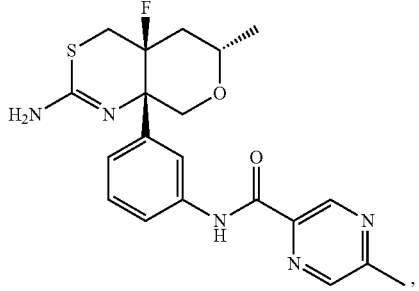
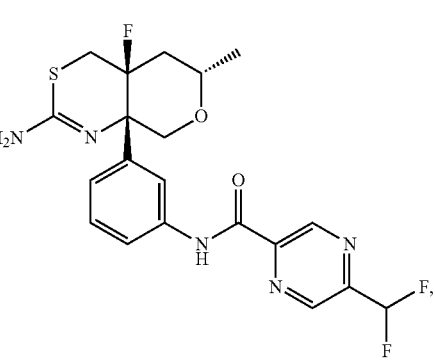
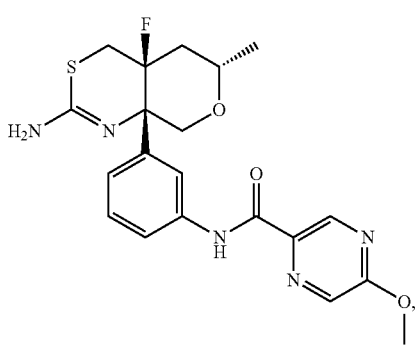

-continued
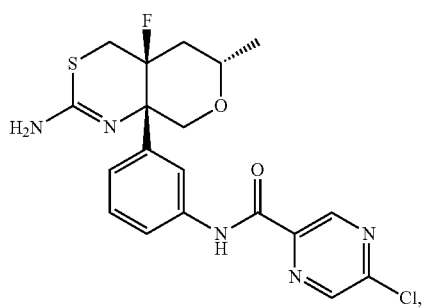
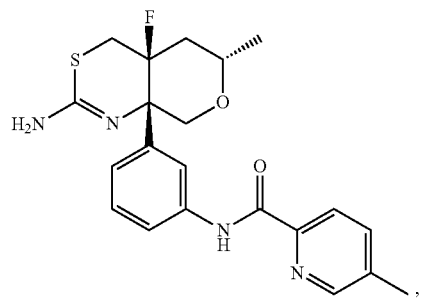
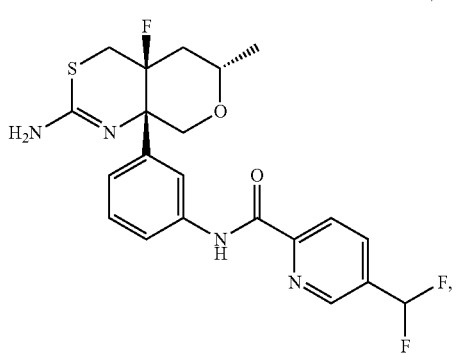
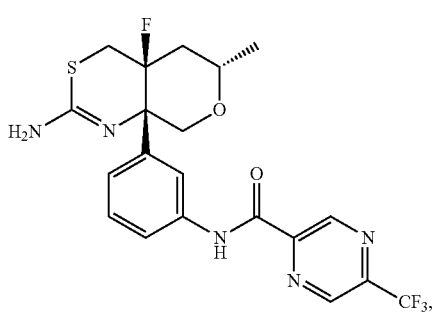
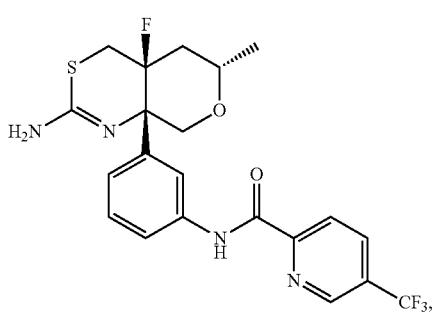
-continued
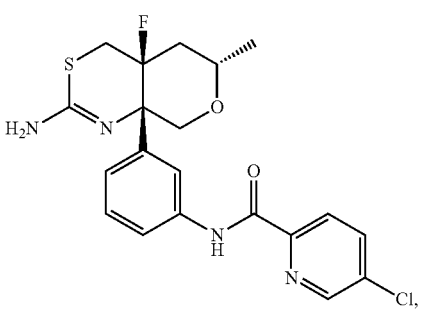
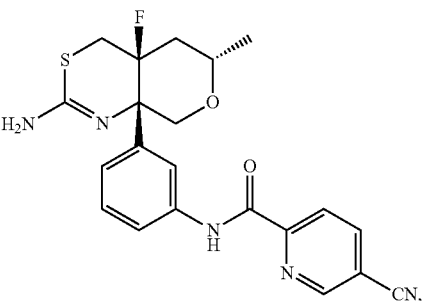
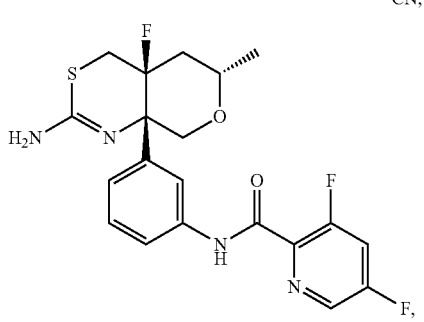
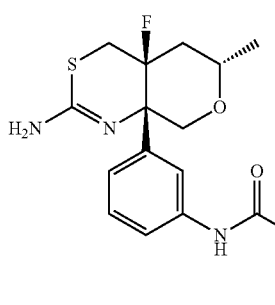
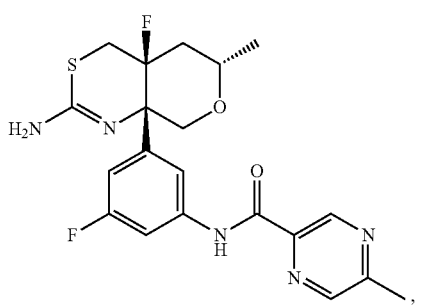

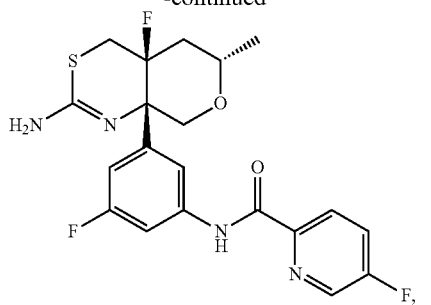

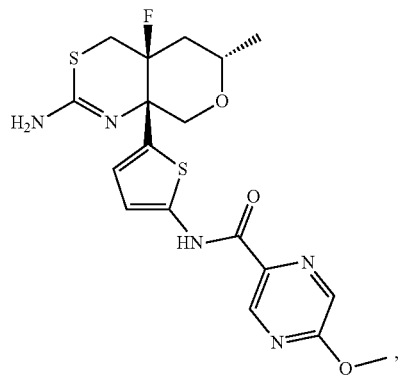

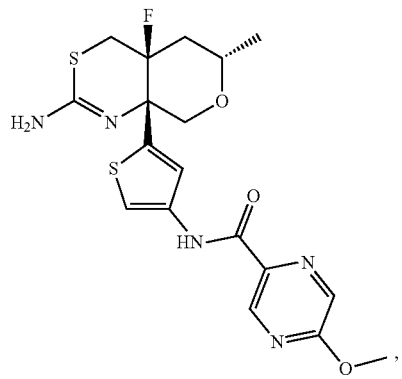

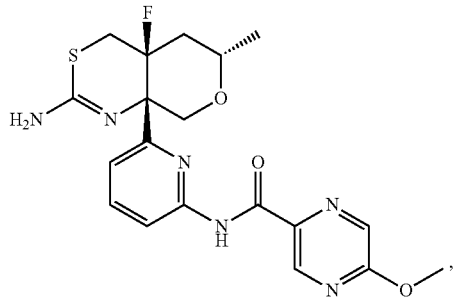

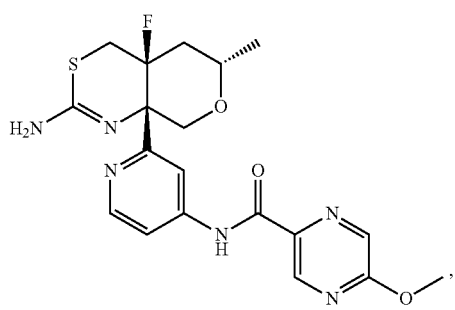

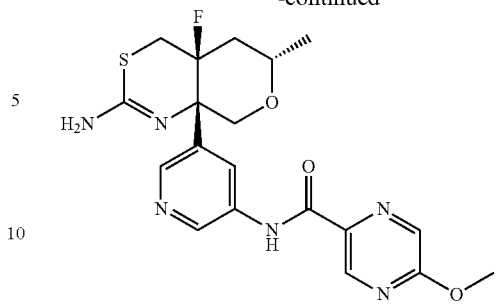

and

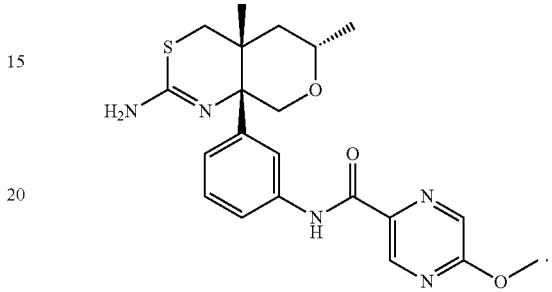

The [1,3]thiazin-2-amine compounds provided in the present invention have good inhibitory effect on BACE1, and can be used to prepare a medicament for treatment of BACE related diseases, especially a medicament used for neurodegenerative diseases such as Alzheimer's disease.

Pharmaceutically acceptable salts of the above compounds are inorganic acid salts or organic acid salts thereof, and said inorganic acid salts are selected from the group consisting of hydrochloride, hydrobromate, hydriodate, sulfate, disulfate, nitrate, phosphate, and acid phosphate; said organic acid salts are selected from the group consisting of formate, acetate, trifluoroacetate, propionate, pyruvate, glycolate, oxalate, malonate, fumarate, maleate, lactate, malate, citrate, tartrate, methanesulfonate, ethanesulfonate, benzenesulfonate, salicylate, picrate, glutamate, ascorbate, camphorate, and camphorsulfonate.

A pharmaceutical composition comprising a compound of formula (I) or formula (II), or a pharmaceutically acceptable salt, stereoisomer, solvate or prodrug thereof, together with a pharmaceutically acceptable carrier.

[1,3]Thiazin-2-amine compound of the present invention can be administrated in suitable dosage forms formulated with one or more pharmaceutically acceptable carriers. These dosage forms are suitable for oral, rectal, topical, buccal, and other parenteral (such as subcutaneous, intramuscular, intravenous etc) administration.

The pharmaceutical composition of the present invention is formulated, quantified, and administrated in a manner in accordance with the medical practice norms. The "effective dose" of compound depends on the specific condition to be treated, the subject to be treated, the cause of diseases, the target of the drug, as well as the mode of administration and the like.

Use of [1,3]thiazin-2-amine compound according to the present invention in the manufacture of a BACE inhibitor, especially the use in the manufacture of a BACE1 inhibitor. Said disease is selected from neurodegenerative diseases, neurological diseases, diabetes, and obesity.

The use of [1,3]thiazin-2-amine compound according to the present invention in the manufacture of a medicament for treatment of neurodegenerative diseases, especially in the manufacture of a medicament for treatment of Alzheimer's diseases (AD).

Compound of formula (I) or formula (II) provided in the present invention, or a pharmaceutically acceptable salt, stereoisomer, solvate or prodrug thereof etc. can be used in the treatment of neurodegenerative diseases alone, or in combination with other drugs or monoclonal antibody drugs, etc. These therapies can be parallelly, simultaneously, sequentially, or separately administrated in combination with the compound of the present invention.

Specific Mode for Carrying Out the Invention

Unless specifically stated, the following terms have the meaning provided below.

"Alkyl" refers to a straight- or branch-chain, monovalent, and saturated hydrocarbon group only consisting of carbon and hydrogen atoms, which has 1~12 carbon atoms. "Alkyl" preferably is the alkyl group having 1~6 carbon atoms, i.e. C1-C6 alkyl, more preferably C1-C4 alkyl. Examples of alkyl groups include but not limited to methyl, ethyl, propyl, iso-propyl, iso-butyl, sec-butyl, tert-butyl, pentyl, n-hexyl, octyl, dodecyl, etc.

"Alkoxyl" refers to the group of formula —OR$_a$ in which R$_a$ is the alkyl group defined herein. Examples of alkoxyl groups include but not limited to methoxyl, ethoxyl, iso-propoxy, tert-butoxy, etc.

"Halogen (halo)" refers to fluorine, chlorine, bromine, or iodine substituent.

"haloalkyl" refers to alkyl defined herein, in which one or more hydrogen(s) is replaced by same or different halogen(s). Examples of haloalkyl include —CH$_2$Cl, —CH$_2$CF$_3$, —CH$_2$CCl$_3$, perfluoro-alkyl (such as —CF$_3$), etc.

"haloalkoxyl" refers to the group of formula —OR$_b$, in which R$_b$ is the haloalkyl defined herein. Examples of haloalkoxyl include but not limited to trifluoromethoxyl, difluoromethoxyl, 2,2,2-trifluoroethoxyl, etc.

"Cycloalkyl" refers to monovalent saturated carbocyclic group consisting of a mono cycle or a bi-cycle, that has 3~12, preferably 3~10, more preferably 3~6 ring atoms. Cycloalkyl can be optionally substituted by one or more substituents, in which each of substituent is independently hydroxyl, alkyl, alkoxyl, halogen, haloalkyl, amino, mono-alkylamino, or di-alkylamino. Examples of cycloalkyl group include but not limited to cyclopropyl, cyclobutyl, cyclopentyl, cyclohexyl, cycloheptyl, etc.

"Cycloalkoxyl" refers to the group of formula —OR$_c$, in which R$_c$ is the cycloalkyl defined herein. Examples of cycloalkoxyl include but not limited to cyclopropoxyl, cyclobutoxyl, cyclopentyloxy, cyclohexyloxy, etc.

"Acyl" refers to the group of formula —C(O)R$_a$, in which R$_a$ is the alkyl defined herein. Examples of acyl include acetyl, n-propionyl, iso-propionyl, n-butyryl, iso-butyryl, tert-butyryl, etc.

"Ester group" refers to the group of formula —C(O)OR$_a$, in which R$_a$ is the alkyl defined herein. Examples of ester group include —C(O)OMe, —C(O)OEt, etc.

"alkylthio" refers to the group of formula —SR$_d$, in which R$_d$ is H or the alkyl defined herein.

"Alkylamino" refers to the group of formula —NR$_d$R$_a$, in which R$_d$ is H or the alkyl defined herein, and R$_a$ is the alkyl defined herein.

"Cycloalkylamino" refers to the group of formula —NR$_e$R$_e$, in which R$_e$ is H, or the alkyl defined herein, or the cycloalkyl defined herein, and R$_e$ is the cycloalkyl defined herein.

"heteroaryl" refers to mono-, bi-, or tri-cyclic aromatic ring having 5 to 12 ring atoms, which contains at least one (including one, two, or three) ring heteratoms selected from N, O, or S, and the remaining ring atoms are C. It should be clear that the attachment point of heteroaryl should be on the aromatic ring. The heteroaryl preferably has 5~8 ring atoms, more preferably 5~6 ring atoms. Examples of heteroaryl include but not limited to imidazolyl, oxazolyl, isoxazolyl, thiazolyl, isothiazolyl, oxadiazolyl, pyrazinyl, thienyl, furyl, pyranyl, pyridyl, pyrrolyl, pyrazolyl, pyrimidinyl, quinolyl, isoquinolyl, benzofuranyl, benzofuranyl, benzothienyl, benzothiapyranyl, benzimidazoyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridyl, carbazolyl, azepinyl, diazepinyl, acridinyl, etc.

The present invention provides three methods for preparation of [1,3]-thiazin-2-amine compound, as follows:

Preparation Method 1

The synthetic route is as follows:

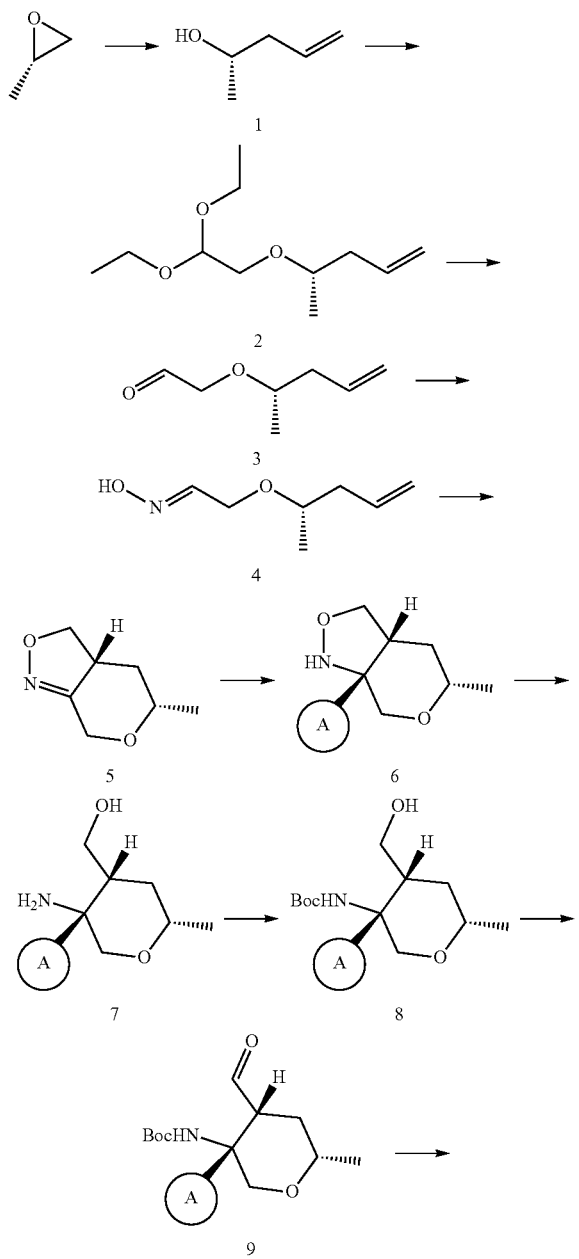

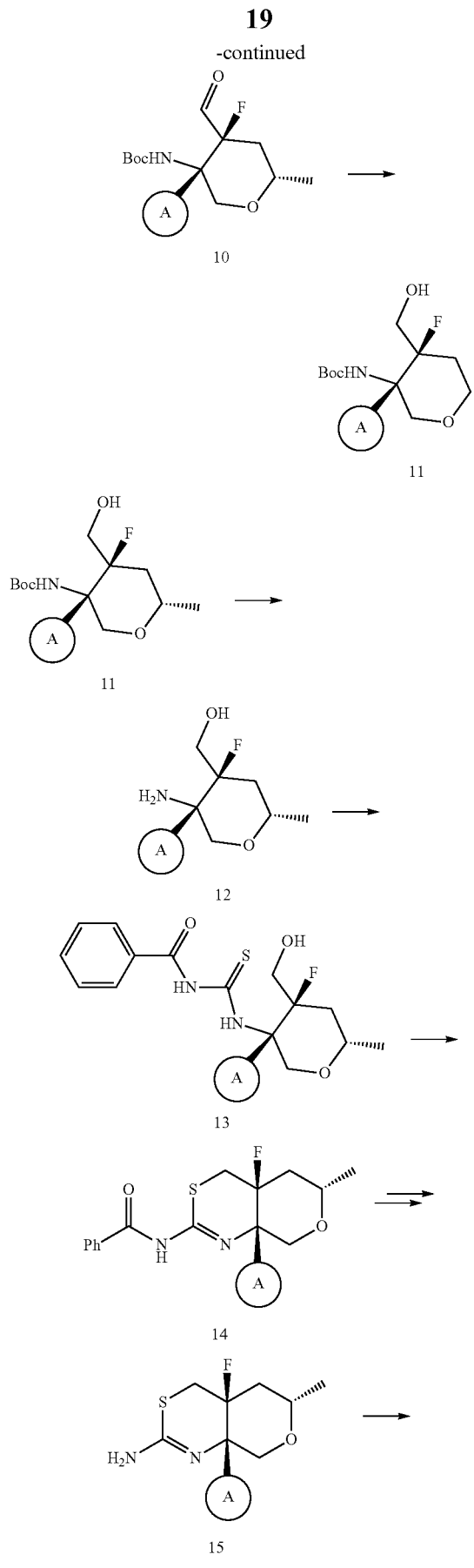

The preparation process includes the following steps:
1) S-epoxypropane is added in diethyl ether, to which a catalyst and vinyl magnesium bromide are added under protective atmosphere for carrying out a ring-opening reaction, to provide compound 1;
2) Compound 1 is added in tetrahydrofuran, to which NaH is added for reaction, then 2-bromo-1,1-diethoxyethane is added for reaction, to provide compound 2;
3) Compound 2 is dissolved in a solvent, to which aqueous HCl solution is added for reaction, to provide compound 3;
4) Compound 3 is dissolved in a solvent, to which hydroxylamine hydrochloride and sodium ethoxide are added for reaction, to provide compound 4;
5) Compound 4 is dissolved in a solvent, subjected to an intramolecular ring-closing reaction in the presence of triethylamine and aqueous sodium hypochlorite solution, to provide compound 5;
6) Compound 5 is dissolved in a solvent, to which boron trifluoride diethyl ether, halo-substituted A, and n-butyl lithium are added for carrying out a substitution reaction, to provide compound 6;
7) Compound 6 is dissolved in a solvent, to which zinc dust is added for carrying out a ring-opening reaction, to provide compound 7;
8) Compound 7 is dissolved in a solvent, to which (Boc)$_2$O and triethylamie are added for carrying out an amino protective reaction, to provide compound 8;
9) Compound 8 is dissolved in a solvent, to which IBX is added for carrying out a reflux reaction, to provide compound 9;
10) Compound 9 is dissolved in a solvent, to which D-proline and fluorinated reagent are added for carrying out a mono-fluoro substitution reaction, to provide compound 10;
11) Compound 10 is dissolved in a solvent, to which sodium borohydride is added for carrying out a reduction reaction, to provide compound 11;
12) Compound 11 is dissolved in a solvent, to which CF$_3$COOH is added for carrying out an amino-deprotection reaction, to provide compound 12;
13) Compound 12 is dissolved in a solvent, to which benzoyl isothiocyanate is added for carrying out a substitution reaction, to provide compound 13;
14) Compound 13 is dissolved in a solvent, to which pyridine and a dehydration condensing agent are added for carrying out a cyclization reaction, to provide compound 14;
15) Compound 14 is dissolved in a solvent, to which 1,8-diazabicycloundeca-7-ene is added for carrying out a reflux reaction, to provide compound 15;
16) Compound 15 is dissolved in a solvent, to which (Boc)$_2$O and triethylamine are adde for carrying out an amino-protection reaction, then it is subjected to a coupling reaction with

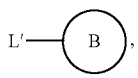

followed by an amino-deprotection reaction, to provide compound of formula (II).

In step 1), said catalyst is CuI; preferably, the molar ratio of CuI to S-epoxypropane is (0.05~0.07):1, and the amount of vinyl magnesium bromide is excessive relative to that of S-epoxypropane, for example, optionally, the molar ratio of vinyl magnesium bromide to S-epoxypropane is (1.1~1.2):1.

Further preferably, vinyl magnesium bromide is added dropwise at a temperature of −78° C.~−75° C., and the reaction is carried out at that temperature for 30 min, then warmed to room temperature to react for 16~20 h.

In step 2), under the protection of argon, the temperature is decreased to 0° C., and NaH is added batchwise, and the reaction is carried out at that temperature for 1 h, then warmed to room temperature to react for 1 h, then decreased to 0° C. 2-Bromo-1,1-diethoxyethane is added dropwise, and the reaction is heated to reflux for 10 h, then decreased to 0° C. again. 2-bromo-1,1-diethoxyethane is added dropwise, then the reaction is heated to reflux for 10 h once again. After that, the temperature is decreased to 0° C., and aqueous ammonium chloride solution is added dropwise to quench the reaction. The molar ratio of NaH to compound 1 is (0.4~0.5):1; the molar ratio of the firstly added 2-bromo-1,1-diethoxyethane to compound 1 is (1.2~1.6):1; the molar ratio of the secondly added 2-bromo-1,1-diethoxyethane to compound 1 is (1.2~1.6):1.

In step 3), said solvent is THF or other solvent that can dissolve compound 2 and have no adverse effect on the reaction.

Preferably, the aqueous HCl solution is added at room temperature, then the mixture is heated to 75° C. to react for 1 h. The concentration of aqueous HCl solution is 1~4 mol/L; the molar ratio of compound 2 to HCl is 1:(1.1~1.3).

In step 4), said solvent is a mixture of ethanol and water, and the volume ratio of ethanol to water is 200:(60~80); the reaction temperature is 60~65° C., and the reaction time is 16~20 h.

In step 5), said solvent is dichloromethane; after addition of triethylamine and sodium hypochlorite aqueous solution, the mixture is stirred at room temperature overnight. The molar ratio of compound 4 to triethylamine is (10~15):1; the mass concentration of sodium hypochlorite aqueous solution is 10%~15%, and the molar ratio of compound 4 to sodium hypochlorite is (5~10):1.

In step 6), said solvent is a mixture of toluene and diethyl ether with a volume ratio of 1:1. Said reaction is carried out for 3 h at −72° C.~−78° C. Wherein, the molar ratio of boron trifluoride diethyl ether to compound 5 is (2.2~2.6):1; calculated on the basis of the moles of halogen, the molar ratio of A substituted by halogen to compound 5 is (1.0~1.2):1; the molar ratio of n-butyl lithium to compound 5 is (1.0~1.2):1.

In step 7), said solvent is acetic acid; said reaction is carried out at room temperature under stirring for 16~20 h.

In step 8), said solvent is tetrahydrofuran; the molar ratio of (Boc)₂O to compound 7 is (1.2~1.6):1; the molar ratio of triethylamine to compound 7 is (3.0~3.3):1. The reaction temperature is 50~60° C., and the reaction time is 14~17 h.

In step 9), said solvent is ethyl acetate; the molar ratio of IBX (2-iodoxybenzoic acid, an oxidant) to compound 8 is (1.8~2.4):1; the reaction time under refluxing is 10~12 h.

In step 10), said solvent is trifluoroethanol; said fluorinated reagent is selectiluor, and calculated on the basis of the moles of fluorine, the molar ratio of the fluorinated reagent to compound 9 is (1.2~1.4):1; the reaction time for monofluoro substitution is 24~48 h.

In step 11), said solvent is ethanol; said reaction is carried out under stirring at room temperature for more than 2 h.

In step 12), said solvent is dichloromethane; the reaction time is more than 2 h.

In step 13), said solvent is dichloromethane; the molar ratio of benzoyl isothiocyanate to compound 12 is (1.0~1.6):1; and the reaction is stirred at room temperature overnight.

In step 14), said solvent is dichloromethane; said reaction is carried out at −50° C.~−60° C. for 2~5 h, then stirred at room temperature overnight; wherein, the molar ratio of pyridine to compound 13 is (4.0~8.0):1; the molar ratio of dehydration condensing agent to compound 13 is (2~4):1. Said dehydration condensing agent may be selected from trifluoromethanesulfonic anhydride or trifluoroacetic anhydride.

In step 15), said solvent is methanol; TLC is used to monitor the reaction until completion.

In step 16), L' has a structure corresponding to L, and L' may be the same as L or partly the same as L, this can be confirmed by the principle of group splicing.

Preparation Method 2

The synthetic route is as follows:

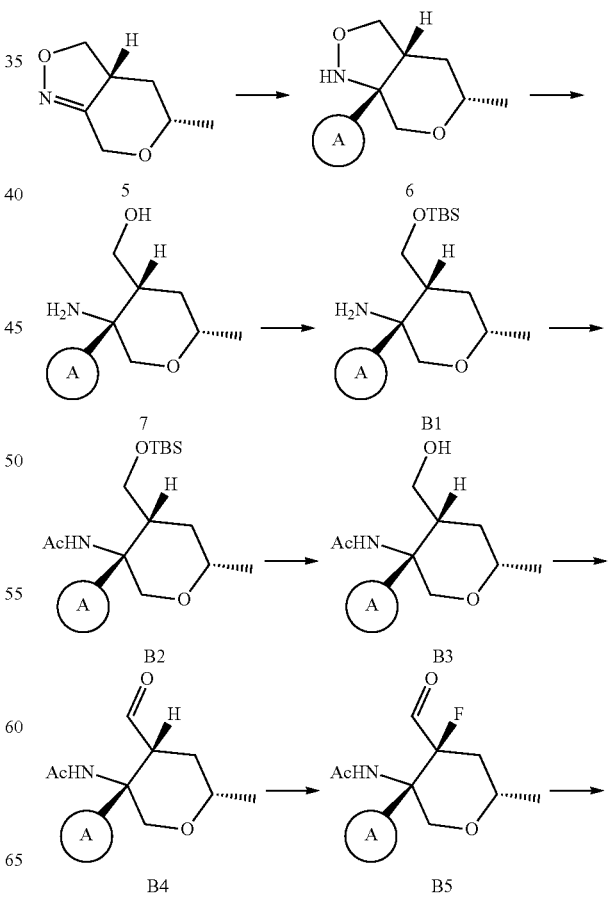

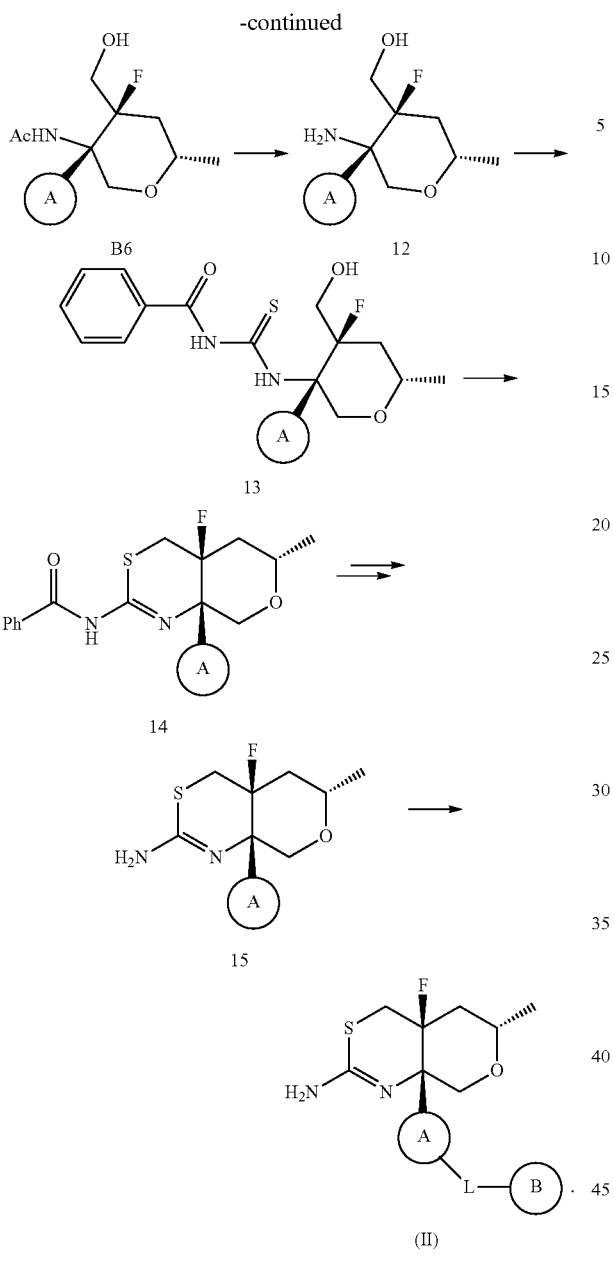

(II)

The preparation process includes the following steps:

a) S-epoxypropane is added in diethyl ether, to which a catalyst and vinyl magnesium bromide are added under protective atmosphere for carrying out a ring-opening reaction, to provide compound 1;

b) Compound 1 is added in tetrahydrofuran, to which NaH is added for reaction, then 2-bromo-1,1-diethoxyethane is added for reaction, to provide compound 2;

c) Compound 2 is dissolved in a solvent, to which aqueous HCl solution is added for reaction, to provide compound 3;

d) Compound 3 is dissolved in a solvent, to which hydroxylamine hydrochloride and sodium ethoxide are added for reaction, to provide compound 4;

e) Compound 4 is dissolved in a solvent, subjected to an intramolecular ring-closing reaction in the presence of triethylamine and aqueous sodium hypochlorite solution, to provide compound 5;

f) Compound 5 is dissolved in a solvent, to which boron trifluoride diethyl ether, halo-substituted A, and n-butyl lithium are added for carrying out a substitution reaction, to provide compound 6;

g) Compound 6 is dissolved in a solvent, to which zinc dust is added for carrying out a ring-opening reaction, to provide compound 7;

h) Compound 7 is dissolved in a solvent, to which 1H-imidazole and TBSCl are added for carrying out a protection reaction of primary alcohol, to provide compound B1;

i) Compound B1 is dissolved in a solvent, to which 4-dimethylaminopyridine, triethylamine, and acetic anhydride are added for carrying out an acylation reaction, to provide compound B2;

j) Compound B2 is dissolved in a solvent, to which tetrabutylammonium fluoride is added for carrying out a deprotection reaction of primary alcohol, to provide compound B3;

k) Compound B3 is dissolved in a solvent, to which IBX is added for carrying out an oxidization reaction, to provide compound B4;

l) Compound B4 is dissolved in a solvent, to which D-proline and a fluorinated reagen are added for carrying out a mono-fluorinated reaction, to provide compound B5;

m) Compound B5 is dissolved in a solvent, to which sodium borohydride is added for carrying out a reduction reaction, to provide compound B6;

n) To compound B6, HCl aqueous solution is added for carrying out a deacylation reaction, to provide compound 12;

o) Compound 12 is dissolved in a solvent, to which benzoyl isothiocyanate is added for carrying out a substitution reaction, to provide compound 13;

p) Compound 13 is dissolved in a solvent, to which pyridine and a dehydration condensing agent are added for carrying out a cyclization reaction, to provide compound 14;

q) Compound 14 is dissolved in a solvent, to which 1,8-diazabicycloundeca-7-ene is added for carrying out a reflux reaction, to provide compound 15;

r) Compound 15 is dissolved in a solvent, to which (Boc)$_2$O and triethylamine are adde for carrying out an amino-protection reaction, then it is subjected to a coupling reaction with

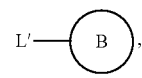

followed by an amino-deprotection reaction, to provide compound of formula (II).

Step a)~step g) are the same as step 1)~step 7).

In step h), said solvent is dichloromethane; the molar ratio of 1H-imidazole to compound 7 is (3~4):1; the molar ratio of TBSCl to compound 7 is (1.1~1.4):1. Said reaction is stirred at room temperature overnight.

In step i), said solvent is tetrahydrofuran; said reaction is carried out at 65° C.~75° C. for 16 h~18 h; wherein, the molar ratio of 4-dimethylaminopyridine to compound B1 is (0.1~0.2):1; the molar ratio of triethylamine to compound B1 is (1.4~1.6):1; the molar ratio of acetic anhydride to compound B1 is (1.4~1.6):1.

In step j), said solvent is tetrahydrofuran; said reaction is carried out at 25° C. for 1 h~2 h; the molar ratio of tetrabutylammonium fluoride to compound B2 is (1.8~2.2):1.

In step k), said solvent is dimethyl sulfoxide; the reaction time is carried out for 16 h~18 h; the molar ratio of IBX to compound B3 is (1.4~1.6):1.

In step l), said solvent is trifluoroethanol; the reaction time is 16 h~18 h; wherein, the molar ratio of D-proline to compound B4 is (2~3):1; the molar ratio of fluorinated reagent to compound B4 is (2~3):1.

In step m), said solvent is ethanol; the reaction time is 2 h~3 h; wherein, the molar ratio of sodium borohydride to compound B5 is (2~3):1.

In step n), the concentration of said HCl aqueous solution is 4~8 mol/L; the deacylation reaction is carried out at 100° C.~110° C. for 14 h~18 h.

Step o)~step r) are the same as step 13)~step 16).

Preparation Method 3

The synthetic route is as follows:

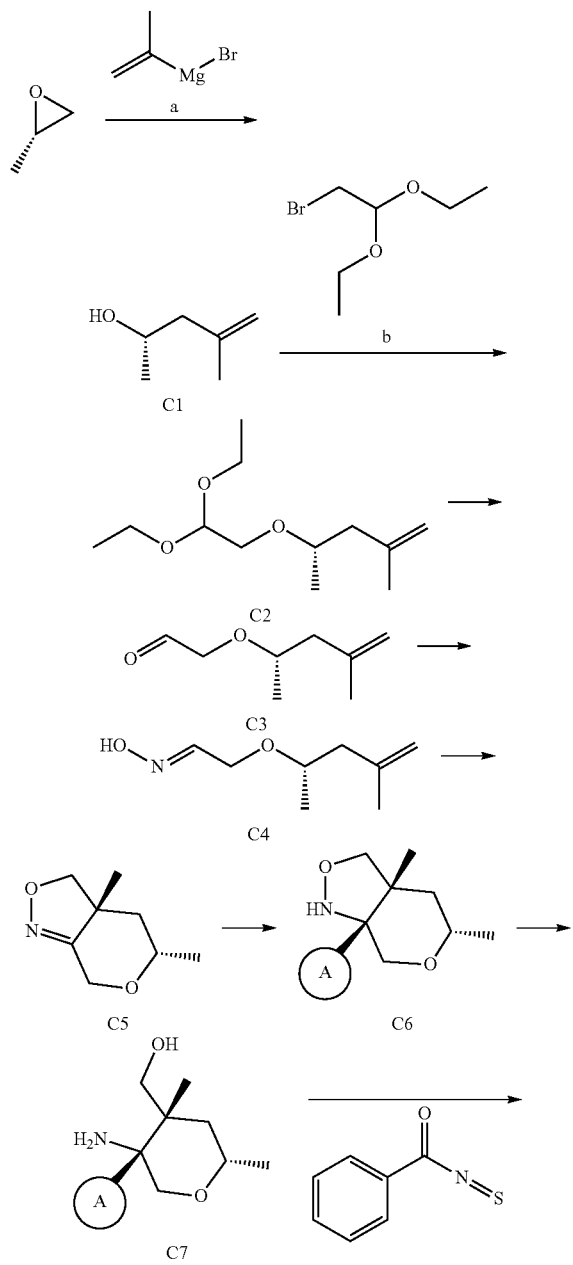

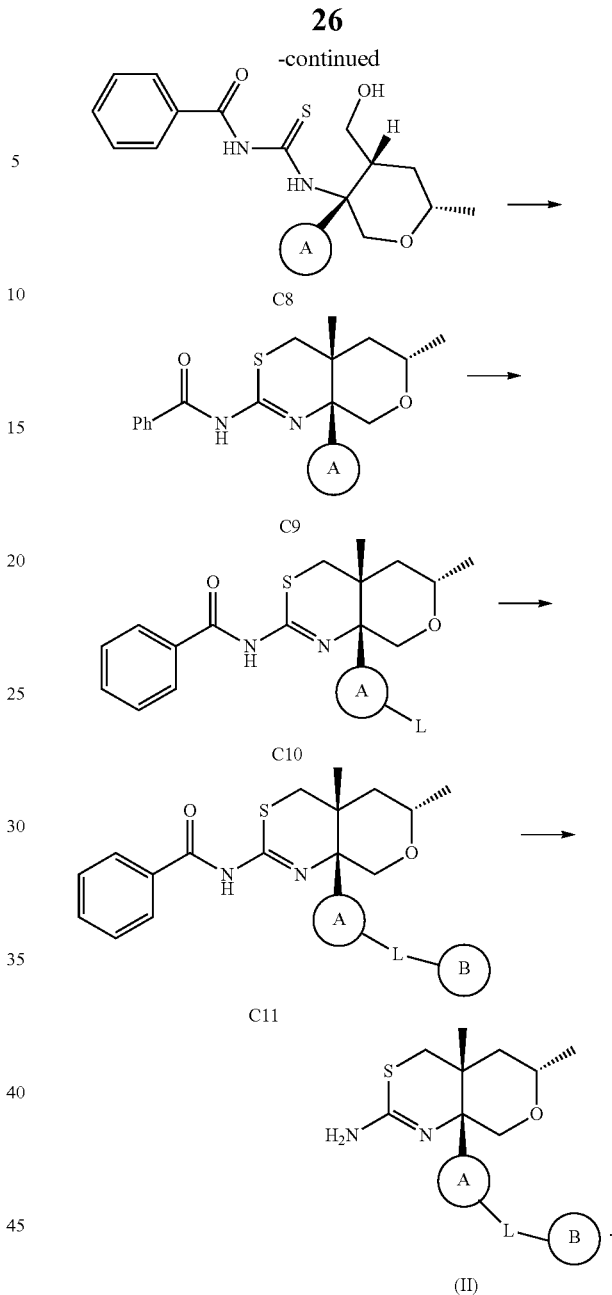

The preparative process includes the following steps:

1) S-epoxypropane is added in diethyl ether, to which a catalyst and isopropenyl magnesium bromide are added under protective gas for carrying out a ring-opening reaction, to provide compound C1;

2) Compound C1 is added in tetrahydrofuran, to which NaH is added, then 2-bromo-1,1-diethoxyethane is added for reaction, to provide compound C2;

3) Compound C2 is dissolved in a solvent, to which HCl aqueous solution is added for reaction, to provide compound C3;

4) Compound C3 is dissolved in a solvent, to which hydroxylamine hydrochloride and sodium ethoxide are added for reaction, to provide compound C4;

5) Compound C4 is dissolved in a solvent, and subjected to an intramolecular ring-closing reaction in the presence of triethylamine and sodium hypochlorite aqueous solution, to provide compound C5;

6) Compound C5 is dissolved in a solvent, to which boron trifluoride diethyl ether, halo-substituted A, and n-butyl lithium are added for carrying out a substitution reaction, to provide compound C6;

7) Compound 6 is dissolved in a solvent, to which zinc dust is added for carrying out a ring-opening reaction, to provide compound C7;

8) Compound C7 is dissolved in a solvent, to which benzoyl isothiocyanate is added for carrying out a substitution reaction, to provide compound C8;

9) Compound C8 is dissolved in a solvent, to which pyridine and a dehydration condensing agent are added for carrying out a cyclization reaction, to provide compound C9;

10) Compound C9 is dissolved in a solvent, subjected to a nitration-reduction reaction or coupling reaction, to provide compound C10;

11) Compound C10 is dissolved in a solvent, then subjected to a condensation reaction with carboxyl-substituted B to provide compound C11, then subjected to an amino-deprotection reaction, to provide compound of formula (II).

The present invention is further elucidated by the specific examples below.

EXAMPLE 1

(4aS,6S,8aS)-4a-fluoro-8a-(2-fluorophenyl)-6-methyl-4,4a,5,6,8,8a-hexahydropyrano[3,4-d][1,3]thiazin-2-amine its structure is

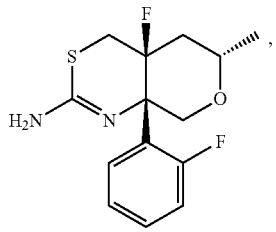 [SMILES: C[C@H]1C[C@@]2(F)CSC(N)=N[C@@]2(c2ccccc2F)CO1]

The synthetic route is as follows:

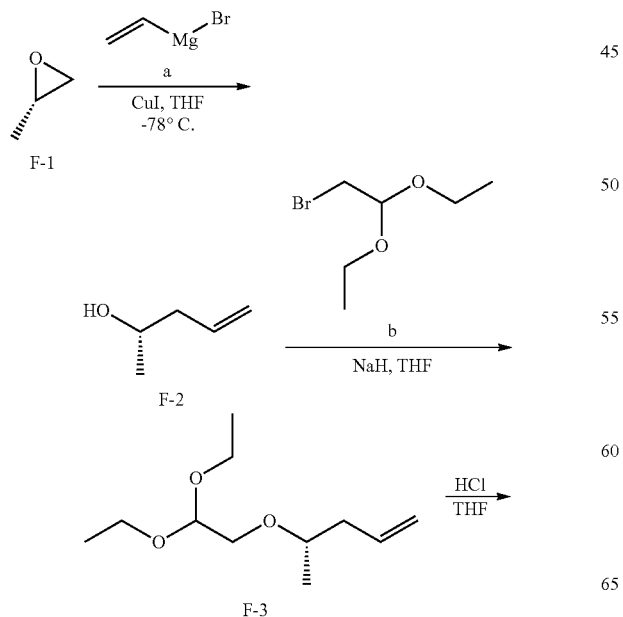

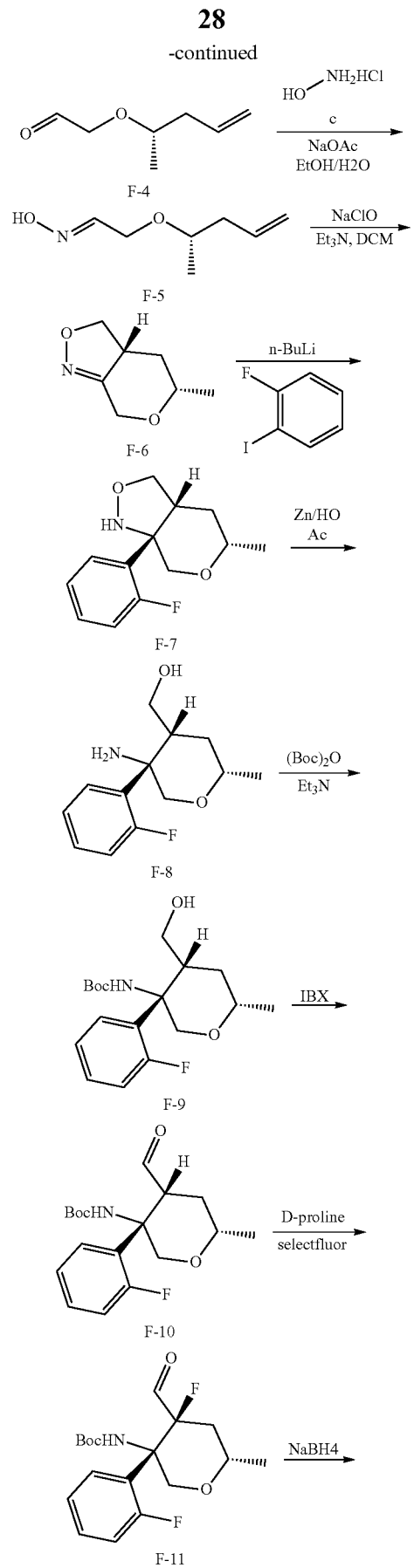

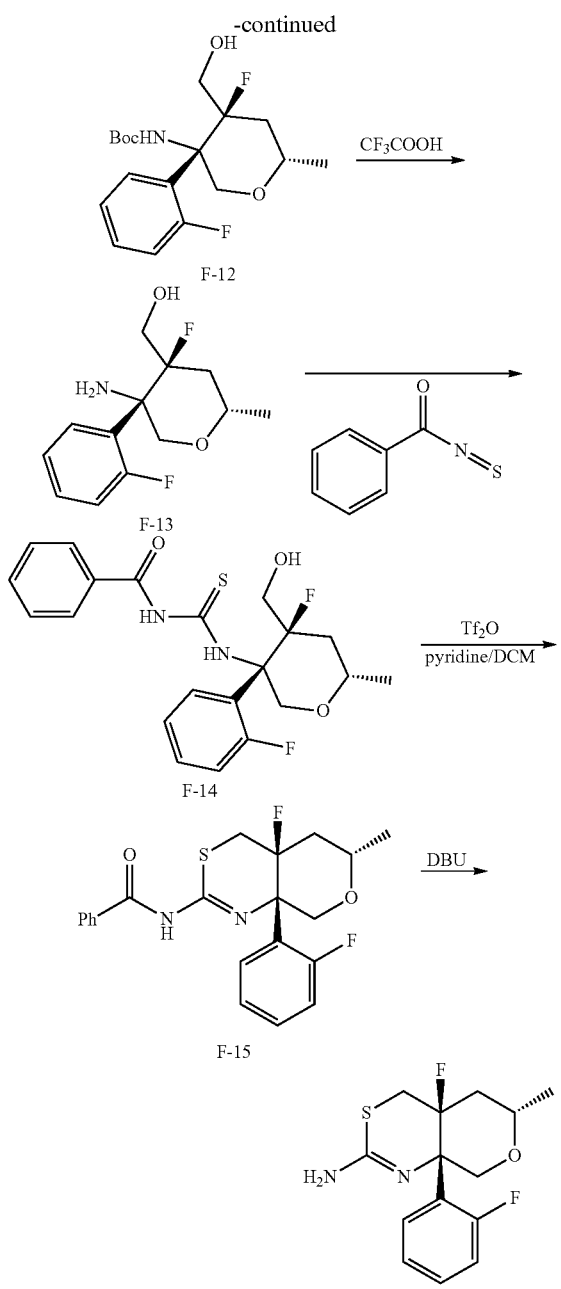

The preparation method of compound of this example includes the following steps:

1) Synthesis of compound F-2: S-epoxypropane (5.81 g, 0.10 mol) was added to anhydrous diethyl ether, then purged by argon. The temperature was decreased to −78° C. Under argon gas, CuI (1.08 g, 0.006 mol) was added, and the mixture was stirred for 30 min, then vinyl magnesium bromide (54.5 mL, 0.11 mol) was added dropwise at −78° C. The system temperature was kept at −78° C.~−75° C. After completion of addition, the mixture was stirred at this temperature for 30 min, then warmed to room temperature, and continually stirred for 18 h. The reaction solution was decreased to 0° C., then the reaction was quenched by addition of 50 mL ammonium chloride aqueous solution, extracted with diethyl ether (100 mL×3). The organic phases were combined, dried, rotationally evaporated to dryness, and directly used in the next step;

2) Synthesis of compound F-3: the crude product obtained in the above step was added in 250 mL THF, and under argon gas, the mixture was decreased to 0° C., then NaH (17.6 g, 0.44 mol) was added batchwise. After completion of addition, the reaction was carried out at 0° C. for one hour, then warmed to room temperature, and the reaction was continually carried out for 1 h, then the temperature was decreased to 0° C. again. Bromoacetaldehyde diethyl acetal(28.6 g, 0.145 mol) was added dropwise, and after completion of addition, the mixture was warmed to room temperature, then heated to reflux for 15 h, the temperature was decreased to 0° C. again. Bromoacetaldehyde diethyl acetal (28.6 g, 0.145 mol) was added dropwise, then the reaction was heated to reflux for 10 h. After the completion of reaction, the temperature was decreased to 0° C., and ammonium chloride aqueous solution was added to quench the reaction. The organic phase was extracted with ethyl acetate (200 mL×3), and the organic phases were combined, dried, rotationally evaporated to dryness, and roughly passed through a column, then subjected to distillation, to obtain the product (12.6 g), with a total yield of 62% for two steps;

Nuclear magnetic resonance information for compound F-3: $^1$H-NMR (CDCl$_3$, 400 MHz): δ 5.87-5.76 (m, 1 H), 5.09-5.02 (n, 2H), 4.59 (t, J=5.29 Hz, 1H), 3.74-3.67 (m, 7H), 2.36-2.29 (m, 1H), 2.21-2.14 (m, 1H), 1.24 (t, J=7.04 Hz, 6H), 1.15 (d, J=6.27 Hz, 3H);

3) Synthesis of compound F-4: compound F-3 (12.6 g, 0.0623 mol) was dissolved in 150 mL THF, to which 37.4 mL of 2 mol/L HCl aqueous solution was then added dropwise at room temperature. After completion of addition, the reaction solution was heated to 75° C. and stirred for 1 h. After the reaction was completed, the temperature was decreased to room temperature, and the reaction solution was rotationally evaporated to half of the volume, then ethyl acetate and water at a volume ratio of 1:1 were added. The phases were separated, and the aqueous phase was extracted with ethyl acetate (50 mL×3); the organic phases were combined, dried, rotationally evaporated to dryness, and directly used in the next step;

4) Synthesis of compound F-5: the crude F-4 obtained in the above step was dissolved in EtOH/H$_2$O (200 mL/70 mL), then hydroxylamine hydrochloride (14.7 g, 21.1 mmol) and sodium acetate (28.8 g, 351.5 mmol) were added batchwise. After completion of addition, the mixture was heated to 60° C. and reacted for 18 h, the reaction was completed by GC detection, 500 mL ethyl acetate and 100 mL water were added. The phases were separated, and the organic phase was dried, rotationally evaporated to dryness, passed through a column (PE~PE:EA=100~5:1), to obtain the product (6.0 g), with a total yield of 67% for two steps.

Nuclear magnetic resonance information for compound F-5: $^1$H-NMR (CDCl$_3$, 400 MHz) δ 7.49 (t, J=5.6 Hz, 0.5 H), 6.90 (t, J=3.6 Hz, 0.5 H), 5.85-5.76 (m, 1H), 5.11-5.06 (m, 2H), 4.38-4.36 (m, 1H), 4.13-4.09 (m, 1H), 3.55-3.51 (m, 1H), 2.34-2.20 (m, 2H), 1.16 (d, J=6.20 Hz, 3H);

5) Synthesis of compound F-6: compound F-5 (6.0 g, 42.0 mol) was dissolved in 160 mL dichloromethane, then placed in the water bath at room temperature, to which triethylamine (0.3 g, 3.0 mol) was added, then sodium hypochlorite aqueous solution (70 mL) was added dropwise. During the process of addition, the temperature of the system was kept no more than 25° C. After addition, the reaction was stirred at room temperature overnight, and after completion of the reaction, the solution was stood for phase separation. The organic phase was washed with saturated aqueous NaCl solution, and the organic phase was dried, rotationally evaporated to dryness, and passed through a column (PE~PE:EA=100~5:1), to obtain 3.6 g product, with a yield of 61%;

Nuclear magnetic resonance information for compound F-6: $^1$H-NMR (CDCl$_3$, 400 MHz) δ 4.69 (d, J=13.2 Hz, 1H), 4.60 (dd, J=8.0 Hz, 10.4 Hz, 1H), 4.19 (dd, J=1.2 Hz, 13.2 Hz, 1H), 3.77 (dd, J=8.0 Hz, 11.6 Hz, 1H), 3.65-3.60 (m, 1H), 3.47-3.42 (m, 1H), 2.19-2.14 (m, 1H), 1.46 (q, J=11.2 Hz, 2H), 1.26 (d, J=6.00 Hz, 3H); GC-MS: 140.99;

6) Synthesis of compound F-7: compound F-6 (3.0 g, 21.2 mmol) was dissolved in toluene/diethyl ether (50 mL/50 mL), then under argon gas, the reaction was decreased to −78° C., to which boron trifluoride diethyl ether (7.2 g, 51.0 mmol) was added dropwise. After addition, the mixture was stirred for 30 min at −78° C., then the starting material 2-bromofluorobenzene (4.1 g, 23.3 mmol) was added dropwise, then n-butyl lithium (9.4 mL, 22.5 mmol) was added dropwise. The temperature of the system was kept below −72° C., and after addition, the mixture was allowed to react at −78° C. for 3 h, then ammonium chloride aqueous solution was added to quench the reaction. The mixture was extracted with ethyl acetate (20 mL×3), and the organic phases were combined, dried, rotationally evaporated to dryness, and passed through a column (PE~PE:EA=100~3:1), to obtain the product (1.52 g), with a yield of 30%;

Nuclear magnetic resonance information for compound F-7: $^1$H-NMR (CDCl$_3$, 400 MHz) δ 7.96-7.92 (m, 1H), 7.28-7.24 (m, 1H), 7.18 (t, J=1.2 Hz, 1H), 7.14-7.00 (m, 1H), 6.31 (s, 1H), 4.16 (dd, J=2.0 Hz, 12.8 Hz, 1H), 3.83-3.69 (m, 3H), 3.54 (q, J=4.8 Hz, 1H), 3.13-3.10 (m, 1H), 1.88-1.82 (m, 1H), 1.47 (q, J=1.6 Hz, 1H), 1.26 (d, J=6.00 Hz, 3H); LC-MS (M+1): 238.01;

7) Synthesis of compound F-8: compound F-7 (1.5 g, 6.4 mmol) was dissolved in 20 mL acetic acid, then placed in water bath, to which zinc dust (6.2 g, 96.2 mmol) was added stepwise, and the temperature of the system was controlled to below 40° C. After addition, the mixture was stirred and reacted at room temperature for 18 h; filtered, and the filter cake was washed with acetic acid, then all of the filtrate was rotationally evaporated to dryness, to which ethyl acetate (50 mL) was then added, followed by addition of 50 mL saturated sodium carbonate aqueous solution. The mixture was stirred and reacted for 1 h, and the resulting mixture was extracted with ethyl acetate (50 mL×3). The organic phases were combined, dried, and rotationally evaporated to dryness, to obtain the product (1.3 g), with a yield of 86%;

Nuclear magnetic resonance information for compound F-8: $^1$H-NMR (CDCl$_3$, 400 MHz) δ 7.65-7.61 (m, 1H), 7.31-28 (m, 1H), 7.22-7.18 (m, 1H), 7.08-7.03 (m, 1H), 4.24 (dd, J=2.0 Hz, 11.2 Hz, 1H), 3.74-3.72 (m, 1H), 3.55 (dd, J=2.4 Hz, 11.2 Hz, 1H), 3.37-3.30 (m, 2H), 2.29 (m, 1H), 1.95-1.92 (m, 1H), 1.70-1.66 (m, 1H), 1.32 (d, J=6.4 Hz, 3H); LC-MS (M+1): 240.01;

8) Synthesis of compound F-9: compound F-8 (1.3 g, 5.4 mmol) was dissolved in 30 mL tetrahydrofuran, to which (Boc)$_2$O (1.8 g, 8.1 mmol) and triethylamine (1.6 g, 16.3 mmol) were then added, and the mixture was heated to 55° C. and reacted for 15 h; the temperature was decreased, and ammonium chloride aqueous solution was added to quench the reaction, then the reaction mixture was extracted with EA (50 mL×3). The organic phases were combined, dried, rotationally evaporated to dryness, and passed through a column (PE~PE:EA=100~5:1), to obtain the product (0.8 g), with a yield of 44%;

Nuclear magnetic resonance information for compound F-9: $^1$H-NMR (CDCl$_3$, 400 MHz) δ 7.58-7.54 (m, 1H), 7.36-7.30 (m, 1H), 7.24-7.20 (m, 1H), 7.09-7.03 (m, 1H), 4.32 (like d, J=12.9 Hz, 1H), 4.04-3.99 (m, 2H), 3.92 (like d, J=12.9 Hz, 1H), 3.80-3.77 (m, 1H), 2.95-2.90 (m, 1H), 1.95-1.84 (m, 1H), 1.70-1.64 (m, 1H), 1.55 (s, 9H), 1.28 (d, J=6.4 Hz, 3H);

9) Synthesis of compound F-10: compound F-9 (0.8 g, 2.35 mmol) was dissolved in 20 mL ethyl acetate, to which IBX (1.3 g, 4.70 mmol) was added, and the mixture was heated to reflux for 10 h; the reaction solution was filtered, rotationally evaporated to dryness, and passed through a column (PE~PE:EA=100~5:1), to obtain the product (0.2 g), with a yield of 25%;

Nuclear magnetic resonance information for compound F-10: $^1$H-NMR (CDCl$_3$, 400 MHz) δ=9.63 (s, 1H), 7.52-7.46 (m, 1H), 7.36-7.28 (m, 1H), 7.21-7.15 (m, 1H), 7.11-7.05 (m, 1H), 5.40 (br, 1H), 3.88-3.64 (m, 3H), 3.56-3.50 (m, 1H), 2.01-1.97 (m, 1H), 1.70-1.61 (m, 1H), 1.41 (s, 9H), 1.32 (d, J=6.4 Hz, 3H);

10) Synthesis of compounds F-11 and F-12: D-proline was added to the solution of F-10 (1.2 g, 3.6 mmol) in trifluoroethanol (16 mL) at room temperature, to which 4 Å molecular sieve (500 mg) was then added, and the mixture was stirred for 4 h. Selectfluor (1.63 g, 4.6 mmol) was added and stirred for additional 36 h, and the reaction solution was filtered and rotationally evaporated to dryness, then the mixed solution of saturated sodium carbonate aqueous solution (20 mL) and ethyl acetate (20 mL) was added to the residue obtained after rotatory evaporation. pH was adjusted to 8, then the organic phase was separated, and the aqueous phase was extracted with ethyl acetate (20 mL×3). The organic phases were combined, dried, and rotationally evaporated to dryness, to obtain the crude product of F-11; the crude product was dissolved in 20 mL ethanol, to which sodium borohydride (0.3 g) was added, and the mixture was stirred and reacted 2 h at room temperature, then quenched with saturated ammonium chloride aqueous solution, extracted with ethyl acetate (50 mL×3); the organic phases were combined, dried, rotationally evaporated to dryness, and passed through a column (PE~PE:EA=100~5:1), to obtain the product (0.3 g), with a yield of 25%;

Nuclear magnetic resonance information for compound F-12: $^1$H-NMR (CDCl$_3$, 400 MHz) δ=8.07 (br, 1H), 7.26-7.21 (m, 2H), 7.12-7.07 (m, 1H), 6.98-6.93 (m, 1H), 5.65 (br, 1H), 4.00-3.71 (m, 5H), 1.94-1.72 (m, 2H), 1.39 (s, 9H), 1.26 (d, J=6.4 Hz, 3H); MS (M+1): 358.1;

11) Synthesis of compound F-13: compound F-12 (0.3 g, 0.8 mmol) was dissolved in DCM (20 mL), to which CF$_3$COOH (4 mL) was then added dropwise in the ice bath, and after the mixture was warmed to room temperature, it was additionally stirred for 2 h. TLC indicated the starting material was completely reacted, and the reaction solution was rotationally evaporated to dryness directly. The residue was dissolved with EA (50 mL), then the organic phase was washed with saturated sodium bicarbonate aqueous solution twice. The organic phase was dried, rotationally evaporated to dryness to obtain the crude product, MS (M+1): 258.2;

12) Synthesis of compound F-14: the crude product F-13 obtained in the above step was dissolved in DCM (15 mL), to which benzoyl isothiocyanate (0.2 g, 1.2 mmol) was added dropwise, and after addition, the mixture was stirred at room temperature overnight. TLC indicated the staring material was completely reacted, to which silica gel was directly added, the mixture was rotationally evaporated to dryness, and passed through a column, to obtain the product F-14 (0.4 g);

Nuclear magnetic resonance information for compound F-14: $^1$H-NMR (CDCl$_3$, 400 MHz) δ=8.97 (br, 1H), 7.88-7.86 (m, 2H), 7.65-7.50 (m, 3H), 7.36-7.28 (m, 1H), 7.18-

7.14 (m, 2H), 7.01-6.95 (m, 1H), 4.05-3.90 (m, 5H), 1.99-1.88 (m, 2H), 1.34 (d, J=6.4 Hz, 3H); LC-MS (M+1): 421.1;

13) Synthesis of compound. F-15: F-14 (0.4 g, 0.95 mmol) was dissolved in DCM (10 mL), to which pyridine (0.3 g, 3.62 mmol) was then added, and the temperature was decreased to −50° C.~−60° C. The solution of trifluoromethanesulfonic anhydride (0.5 g, 1.90 mmol) in DCM (10 mL) was added dropwise, and after addition, the resulting mixture was stirred at −50° C. for 3 h, then at room temperature overnight. TLC indicated the starting material was completely reacted, and the reaction was quenched by ammonium chloride aqueous solution and extracted with DCM. The organic phases were combined, rotationally evaporated to dryness, and passed through a column, to obtain the product F-15 (0.3 g);

Nuclear magnetic resonance information for compound F-15: $^{1}$H-NMR (CDCl$_3$, 400 MHz) δ=8.13 (br, 1H), 7.56-7.34 (m, 6H), 7.21-7.00 (m, 3H), 4.89 (d, J=12.0 Hz, 1H), 4.12-4.01 (m, 1H), 3.86 (d, J12.0 Hz, 1H), 3.13-2.90 (m, 1H), 2.61-2.53 (m, 1H), 2.45-2.28 (m, 1H), 1.98-1.91 (m, 1H), 1.29 (d, J=6.4 Hz, 3H); LC-MS (M+1): 403.2;

14) Synthesis of (4aS,6S,8aS)-4a-fluoro-8a-(2-fluorophenyl)-6-methyl-4,4a,5,6,8,8a-hexahydropyrano[3,4-d][1,3]thiazin-2-amine: F-15 (0.3 g) was dissolved in methanol (10 mL), to which 1,8-diazabicycloundeca-7-ene (0.15 g) was then added, and the reaction was heated to reflux till TLC indicated the reaction was completed. The temperature was decreased, and silica gel was added, then the mixture was rotationally evaporated to dryness and passed through a column to obtain the product (0.2 g), LC-MS (M+1): 299.2.

EXAMPLE 2

(4aS,6S,8aS)-8a-(5-bromo-2-fluorophenyl)-4a-fluoro-6-methyl-4,4a,5,6,8,8a-hexahydropyrano[3,4-d][1,3]thiazin-2-amine its structure is:

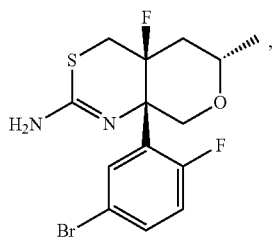

The synthetic route is as follows:

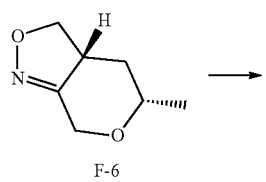
F-6

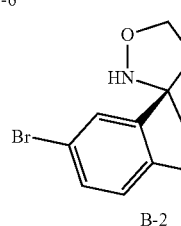
B-2

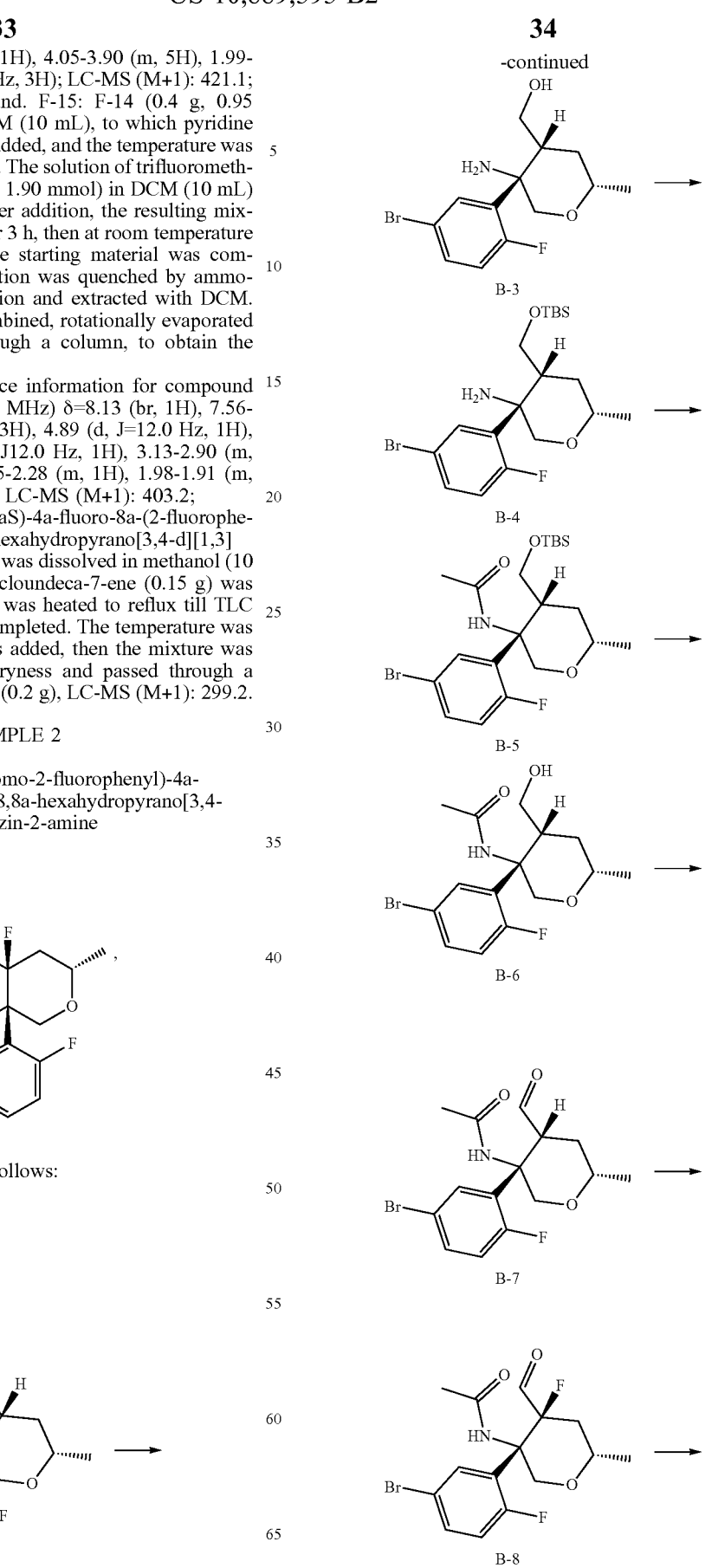

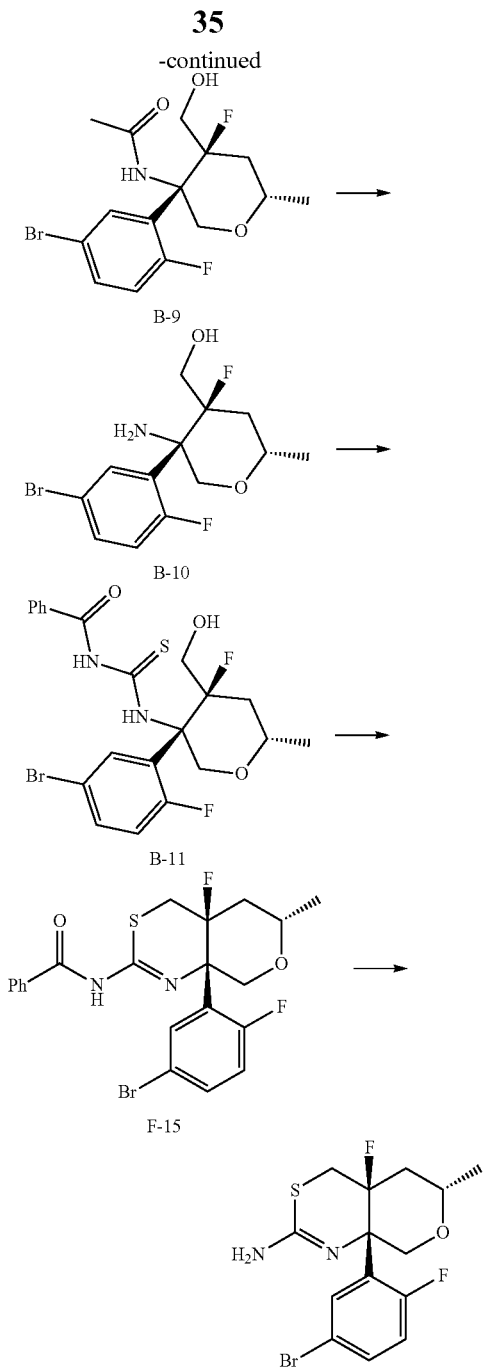

B-9

B-10

B-11

F-15

The preparation method for compound of this example includes the following steps:

1) Synthesis of compound B-2: using compound F-6 and 4-bromo-1-fluoro-2-iodobenzene as starting materials to synthesize compound B-2, the experimental procedures and work-up can refer to the synthesis of compound F-7 in example 1;

Nuclear magnetic resonance information for compound B-2: $^1$H-NMR (CDCl$_3$, 400 MHz) δ=8.09 (dd, $J_1$=1.6 Hz, $J_2$=8.0 Hz, 1H), 7.40-7.36 (m, 1H), 6.92 (dd, $J_1$=8.0 Hz, $J_2$=12.0 Hz, 1H), 6.27 (s, 1H), 4.11-4.07 (m, 1H), 3.81-3.69 (m, 3H), 3.57-3.54 (m, 1H), 3.11-3.05 (m, 1H), 1.88-1.82 (m, 1H), 1.49-1.39 (m, 1H), 1.25 (d, J=6.4 Hz, 3H);

2) Synthesis of compound B-3: compound B-2 (3.63 g, 11.48 mmol) was dissolved in 80 ml glacial acetic acid, to which zinc dust (11.2 g, 172 mmol) was then added batchwise, and the reaction was stirred for 16 h at room temperature; TLC detection indicated the reaction was completed. The reaction solution was filtered through celite, and the filtrate was concentrated in vacuum to remove acetic acid, then pH was adjusted to 8 by adding saturated sodium carbonate aqueous solution, then the mixture was extracted with ethyl acetate (100 ml×3) for three times. The organic phase was washed with 100 ml saturated aqueous NaCl solution, dried by anhydrous sodium sulphate, concentrated to provide 3.62 g crude product as yellow oil, which was directly used in the next step without purification;

3) Synthesis of compound B-4: the crude product of compound B-3 (3.62 g, 11.38 mmol) and 1H-imidazole (2.32 g, 34.14 mmol) were dissolved in 100 ml dichloromethane, to which TBSCl (2.06 g, 13.66 mmol) was then added batchwise in ice-water bath, then the reaction was naturally warmed to room temperature and stirred overnight. TLC detection showed that the reaction was completed, and the reaction solution was concentrated to provide a crude product, which was purified by column chromatography to obtain compound B-4 (4.2 g);

4) Synthesis of compound B-5: compound B-4 (4.2 g, 9.75 mmol) was dissolved in redistilled tetrahydrofuran (65 ml), to which DMAP (119 mg, 0.975 mmol), triethylamine (2 ml, 14.62 mmol), and acetic anhydride (1.4 ml, 14.62 mmol) were then added. The solution was stirred for 16 h at 70° C. TLC detection indicated that the reaction was completed, and the reaction solution was cooled to room temperature and concentrated, to obtain the crude product, which was purified by column chromatography to obtain B-5 (3.3 g);

Nuclear magnetic resonance information for compound B-5: $^1$H-NMR (CDCl$_3$, 400 MHz) δ=7.38-7.35 (dd, $J_1$=2.51 Hz, $J_2$=2.33 Hz, 1H), 7.28-7.32 (m, 2H), 6.87-6.81 (q, 1H), 4.97-4.94 (d, J=11.85 Hz, 1H), 3.83-3.80 (d, J=11.85 Hz, 1H), 3.68-3.62 (m, 1H), 3.47-3.38 (m, 21-1), 2.22-2.18 (m, 1H), 2.04 (s, 3H), 1.88-1.79 (q, 1H), 1.52-1.48 (m, 1H), 1.24-1.23 (d, J=6.18 Hz, 3H), 8.07 (s, 9H), 0.03 (s, 6H);

5) Synthesis of compound B-6: compound B-5 (3.3 g, 6.95 mmol) was dissolved in 100 ml tetrahydrofuran, to which tetrabutylammonium fluoride (4.4 g, 13.89 mmol) was then added, and the reaction solution was stirred at 25° C. for 1 h. TLC detection indicated that the reaction was completed, and the reaction solution was concentrated, to obtain the crude product, which was purified by column chromatography to obtain B-6 (1.8 g);

Nuclear magnetic resonance information for compound B-6: $^1$H-NMR (CDCl$_3$, 400 MHz) δ=7.71 (br, 1H), 7.36-7.32 (m, 1H), 6.89-6.84 (m, 1H), 6.49 (br, 1H), 4.08 (br, 1H), 4.13-3.52 (m, 2H), 3.48-3.42 (m, 2H), 2.80 (br, 1H), 2.12 (s, 3H), 1.55-1.53 (q, 1H), 1.36 (br, 1H), 1.27-1.26 (d, J=6.39, 3H);

6) Synthesis of compound B-7: compound B-6 (1.8 g, 5 mmol) was dissolved in 50 ml DMSO, to which IBX (2.1 g, 7.5 mmol) was added, then the reaction was stirred for 16 h at room temperature; TLC detection indicated that the reaction was completed, and under the conditions of keeping the temperature below 25° C., 50 ml saturated sodium bicarbonate solution was slowly added to the solution, then 50 ml ethyl acetate was added. The resulting mixture was stirred for 15 mm at room temperature, and filtered through celite. The filtrate was extracted with ethyl acetate (100 mL×3) for three times, and the organic phase was washed with 100 ml saturated aqueous NaCl solution, dried by anhydrous sodium sulfate, concentrated to obtain the crude product, which was purified by column chromatography to obtain B-7 (1.2 g);

Nuclear magnetic resonance information for compound B-7: $^1$H-NMR (CDCl$_3$, 400 MHz) δ=9.64 (s, 1H), 7.52-7.49 (dd, J$_1$=2.54 Hz, J$_2$=2.37 Hz, 1H), 7.43-7.40 (m, 1H), 6.99-6.95 (q, 1H), 6.16 (s, 1H), 3.82-3.79 (d, J=12.04 Hz, 1H), 3.70-3.63 (m, 2H), 3.47-3.439 (dd, J$_1$=J$_2$=3.53 Hz, 1H), 2.09 (s, 3H), 2.038-1.987 (m, 1H), 1.65-1.61 (m, 1H), 1.33-1.32 (d, J=6.18 Hz, 3H);

7) Synthesis of compound B-8: compound B-7 (1.2 g, 3.35 mmol) was dissolved in 20 ml trifluoroethanol, to which D-proline (0.85 g, 7.37 mmol), 4 Å molecular sieve (1.2 g), and glacial acetic acid (20 mg) were added sequentially; after the reaction solution was stirred at room temperature for 16 h, Selectfluor reagent (2.96 g, 8.38 mmol) was added. After the reaction was stirred at room temperature for additional 16 h, trifluoroethanol was removed by evaporation under reduced pressure, and the reaction solution was adjusted to pH 8 by saturated sodium bicarbonate solution, then extracted three times with ethyl acetate (100 mL×3). The organic phase was dried with anhydrous sodium sulfate, and concentrated to provide the crude product, which was directly used in the next step without purification;

8) Synthesis of compound B-9: the crude product obtained in the above step was directly dissolved in 40 ml ethanol, to which sodium borohydride (255 mg, 6.7 mmol) was added batchwise at room temperature, then the reaction was stirred at room temperature for 2 h. The reaction was concentrated under reduced pressure to evaporate ethanol, to which saturated ammonium chloride solution (60 ml) was added, and the resulting mixture was extracted three times with dichloromethane (50 mL×3). The organic phase was dried with anhydrous sodium sulfate, and concentrated to provide the crude product, which was simply separated by column chromatography to obtain the slightly impurified product (0.7 g), which was directly used in the next step;

9) Synthesis of compound B-10: To 100 ml reaction bottle containing the crude compound B-9 obtained in the above step (0.7 g, 1.85 mmol), was added 6N HCl (32 ml), then stirred at 105° C. for 16 h. The reaction solution was concentrated under reduced pressure to evaporate HCl, then was adjusted to pH 8 with 15% NaOH solution, and extracted three times with ethyl acetate (50 mL×3). The organic phase was dried over anhydrous sodium sulfate, and concentrated to provide a brown oily liquid (0.6 g), which was directly used in the next step;

10) Synthesis of compound B-11: the crude product obtained in the above step (0.6 g, 1.79 mmol) was dissolved in 25 ml dichloromethane, to which benzoyl isothiocyanate (0.26 ml, 1.96 mmol) was then added, and the reaction was stirred at room temperature overnight, and concentrated to provide the crude product, which was purified by column chromatography to obtain B-11 (258 mg);

Nuclear magnetic resonance information for compound B-11: $^1$H-NMR (CDCl$_3$, 400 MHz) δ=11.96-11.56 (2br, 1H), 8.89 (S, 1H), 7.89-7.87 (d, J=8.08 Hz, 2H), 7.66-7.63 (t, 1H), 7.55-7.51 (t, 2H), 7.41 (br, 1H), 6.87 (br, 1H), 4.08-3.55 (m, 4H), 1.88 (br, 1H), 1.34-1.33 (d, J=6.06 Hz, 3H), 1.28-1.24 (m, 3H);

11) Synthesis of compound B-12: compound B-11 (258 mg, 0.517 mmol) was dissolved in 30 ml dichloromethane, to which pyridine (310 mg, 3.93 mmol) was then added, then the reaction was cooled to −78° C., and trifluoroacetic anhydride (584 mg, 2.068 mmol) was added dropwise at this temperature. After completion of addition, the mixture was naturally warmed to room temperature, and then stirred overnight. Then, 10 ml saturated ammonium chloride solution was added dropwise to quench the reaction, and the mixture was extracted with dichloromethane. The organic phase was dried with anhydrous sodium sulfate, concentrated, and separated by column chromatography to obtain B-12 (87 mg);

Nuclear magnetic resonance information for compound B-12: $^1$H-NMR (CDCl$_3$, 400 MHz) δ=8.07-8.05 (d, J=7.13 Hz, 1H), 7.56-7.45 (m, 5H), 7.02-6.97 (q, 1H), 4.79-4.76 (dd, J$_1$=J$_2$=1.21 Hz, 1H), 4.05-4.02 (m, 1H), 3.87-3.84 (d, J=12.31 Hz, 1H), 3.07-3.01 (q, 1H), 2.61-2.56 (m, 1H), 2.42-2.28 (m, 1H), 1.97-1.90 (m, 1H), 1.29-1.24 (n, 3H);

12) Synthesis of (4aS,6S,8aS)-8a-(5-bromo-2-fluorophenyl)-4a-fluoro-6-methyl-4,4a,5,6,8,8a-hexahydropyrano[3,4-d][1,3]thiazin-2-amine: compound B-12 (56 mg) was dissolved in methanol (10 ml), to which 1,8-diazabicycloundeca-7-ene (40 μL) was then added, and the reaction was heated to reflux till TLC indicated the reaction was completed. The temperature was decreased, and silica gel was added, then the mixture was rotationally evaporated to dryness and passed through a column to obtain the product (35 mg).

Nuclear magnetic resonance information for the compound: $^1$H-NMR (CDCl$_3$, 400 MHz) δ=7.47-7.45 (dd, J$_1$=2.70 Hz, J$_2$=6.59 Hz, 1H), 7.43-7.39 (m, 1H), 6.97-6.92 (q, 1H), 4.80-4.77 (dd, J$_1$=1.45 Hz, J$_2$=11.18 Hz, 1H), 4.03-4.00 (m, 1H), 3.78-3.75 (d, J=11.64 Hz, 1H), 2.98-2.93 (q, 1H), 2.50-2.46 (dd, J$_1$=4.92, J$_2$=11.90 Hz, 1H), 2.39-2.22 (m, 1H), 1.87-1.80 (m, 1H), 1.30-1.28 (m, 5H).

EXAMPLE 3-6

For example 3-6 compounds, refer to the procedures in example 2, in step 1)

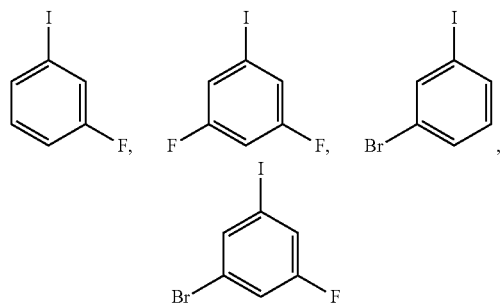

was used instead of 4-bromo-1-fluoro-iodobenzene in example 2 respectively, to synthesize example 3-6 compounds as shown in Table 1 respectively.

TABLE 1

| Example 3-6 compounds | | |
|---|---|---|
| Example name Example No. | Structure of compound Structure of compound | molecular weight molecular weight |
| 3 | ![structure] | 298.35 |

TABLE 1-continued

Example 3-6 compounds

| Example name Example No. | Structure of compound Structure of compound | molecular weight molecular weight |
|---|---|---|
| 4 | | 316.34 |
| 5 | | 359.26 |
| 6 | | 377.25 |

EXAMPLE 7

(4aS,6S,8aS)-8a-(5-amino-2-fluorophenyl)-4a-fluoro-6-methyl-4,4a,5,6,8,8a-hexahydropyrano[3,4-d][1,3]thiazin-2-amine Its structure is:

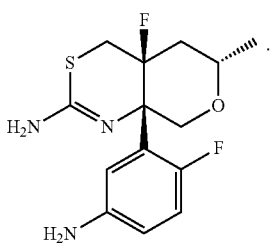 [SMILES: C[C@H]1C[C@@]2(F)CSC(N)=N[C@@]2(c2cc(N)ccc2F)CO1]

The synthetic route for the compounds of this example is as follows:

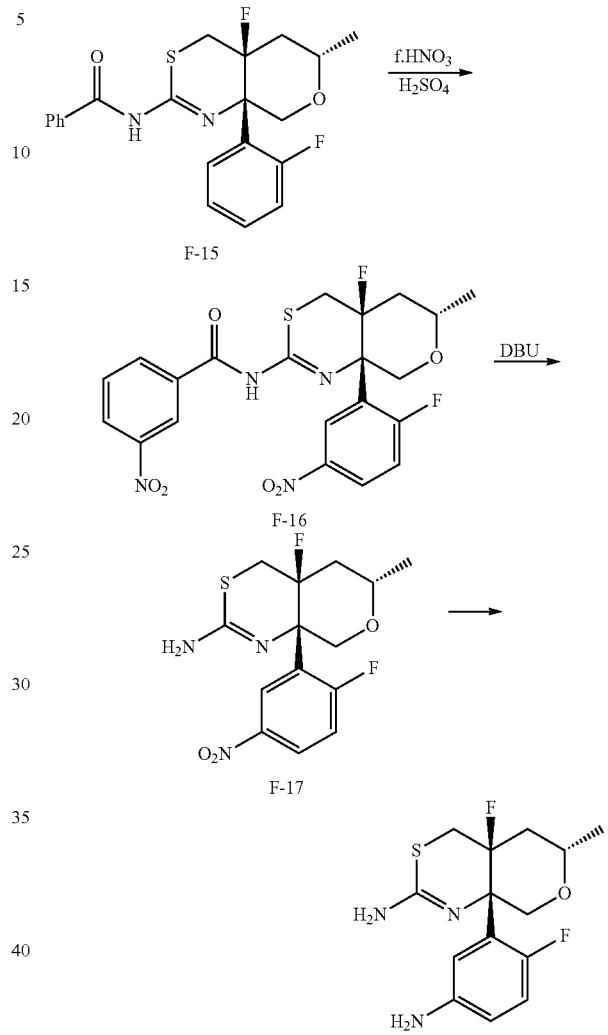

The preparation method for the compound of this example includes the following steps:

1) Synthesis of compound F-16: F-15 (0.3 g, 0.7 mmol) was added to concentrated sulfuric acid (10 mL) in ice bath, then fuming nitric acid (0.2 mL) was added dropwise at this temperature, and the temperature of this system was kept below 5° C. After completion of addition, the reaction was continued for 30 min in ice bath, then warmed to room temperature to react for 2 h; LC-MS detection indicated the completion of reaction. The reaction solution was directly poured into the mixed solution of ice and water, and extracted three times with ethyl acetate. The organic phases were combined and washed with saturated sodium bicarbonate aqueous solution, dried, rotationally evaporated to dryness, and passed through column chromatography to obtain the product F-16 (0.4 g);

Nuclear magnetic resonance information for compound F-16: $^1$H-NMR (CDCl$_3$, 400 MHz) δ=11.31 (br, 1H), 9.04 (t, J=4.0 Hz, 1H), 8.50 (dt, J$_1$=1.2 Hz, J$_2$=8.0 Hz, 1H), 8.46 (dd, J$_1$=2.8 Hz, J$_2$=8.0 Hz, 1H), 8.39-8.36 (m, 1H), 8.33-8.29 (m, 1H), 7.64 (t, J=8.0 Hz, 1H), 7.34-7.29 (m, 1H), 4.72-4.68 (m, 1H), 3.95 (d, J=12.0 Hz, 1H), 3.17-3.12 (m, 1H), 2.80-2.76 (m, 1H), 2.47-2.31 (m, 1H), 2.02-1.98 (m, 1H), 1.32 (d, J=6.4 Hz, 3H); MS (M+1): 493.1.

2) Synthesis of compound F-17: F-16 (0.3 g, 0.6 mmol) was dissolved in 10 mL methanol, then 1,8-diazabicycloundeca-7-ene (DBU) (0.1 g, 0.66 mmol) was added, and the reaction was refluxed overnight. TLC indicated the starting material was reacted completely, and silica gel was directly added. The mixture was rotationally evaporated to dryness and passed through a column to obtain F-17 (96 mg);

Nuclear magnetic resonance information for compound F-17: $^1$H-NMR (CDCl$_3$, 400 MHz) δ=8.37-8.34 (m, 1H), 8.22-8.18 (m, 1H), 7.22-7.17 (m, 1H), 4.79 (dt, J$_1$=4.0 Hz, J$_2$=8.0 Hz, 1H), 4.08-4.00 (m, 1H), 3.79 (d, J=8.0 Hz, 1H), 2.90-2.84 (m, 1H), 2.55-2.50 (m, 1H), 2.41-2.24 (m, 1H), 1.89-1.82 (m, 1H), 1.30 (d, J=6.4 Hz, 3H); MS (M+1): 344.0;

3) Synthesis of (4aS,6S,8aS)-8a-(5-amino-2-fluorophenyl)-4a-fluoro-6-methyl-4,4a,5,6,8,8a-hexahydropyrano[3,4-d][1,3]thiazin-2-amine: F-17 (100 mg, 0.3 mmol) was dissolved in 10 mL methanol, then 30 mg wet Palladium on carbon was added. The reaction was carried out at room temperature under hydrogen gas for 1.5 h, and LC-MS detection was used to monitor completion of reaction. The reaction mixture was filtered by suck, and rotationally evaporated to dryness to remove methanol and provide the product, MS (M+1): 314.0.

EXAMPLE 8

(4aS,6S,8aS)-4a-fluoro-8a-(2-fluoro-5-(5-(propyn-1-yl)pyridin-3-yl)phenyl)-6-methyl-4,4a,5,6,8,8a-hexahydropyrano[3,4-d][1,3]thiazin-2-amine Its structure is:

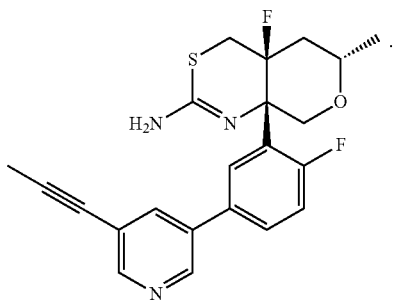 [SMILES: CC#Cc1cncc(-c2cccc([C@]34CO[C@@H](C)C[C@@]3(F)CSC(N)=N4)c2)c1]

The synthetic route for compound of this example is:

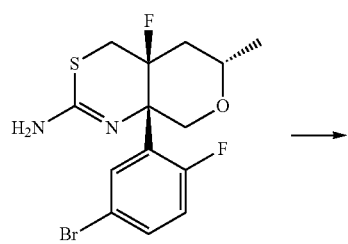

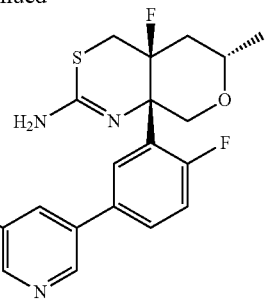

The preparation method for compound of this example: (4aS,6S,8aS)-8a-(5-bromo-2-fluorophenyl)-4a-fluoro-6-methyl-4,4a,5,6,8,8a-hexahydropyrano[3,4-d][1,3]thiazin-2-amine (44 mg, 0.117 mmol), [5-(propyn-1-yl)pyridin-3-yl]boric acid (28.2 mg, 0.175 mmol), palladium acetate (1.35 mg, 0.006 mmol), 1,1'-bis(diphenylphosphino)ferrocene (6.65 mg, 0.012 mmol), and potassium carbonate (65 mg, 0.468 mmol) were added to the mixed solution of dioxane/water (2 ml/0.5 ml), and reacted overnight at 105° C. under the nitrogen protection. The reaction was cooled to room temperature and concentrated, to which water (10 mL) was added. The mixture was extracted with ethyl acetate, and the organic phase was dried, rotationally evaporated to dryness, passed through a column, to obtain the product (11 mg).

Nuclear magnetic resonance information for the compound: $^1$H-NMR (CDCl$_3$, 400 MHz) δ=8.69-8.68 (d, J=2.11 Hz, 1H), 8.59-8.58 (d, J=1.88 Hz, 1H), 7.81-7.80 (t, 1H), 7.64-7.54 (m, 1H), 7.52-7.45 (m, 1H), 7.44-7.36 (m, 1H), 7.19-7.14 (q, 1H), 4.90-4.87 (dd, J$_1$=1.45 Hz, J$_2$=11.25 Hz, 1H), 4.15-4.05 (m, 2H), 3.85-3.82 (d, J=11.25 Hz, 1H), 3.01-2.96 (q, 1H), 2.53-2.49 (dd, J$_1$=4.97 Hz, J$_2$=11.53 Hz), 2.41-2.24 (m, 1H), 2.11 (s, 1H), 1.90-1.86 (m, 1H), 1.62-1.59 (dd, J$_1$=2.41 Hz, J$_2$=6.75 Hz, 1H), 1.32-1.30 (d, J=6.28 Hz, 3H).

EXAMPLES 9-10

For Examples 9-10,

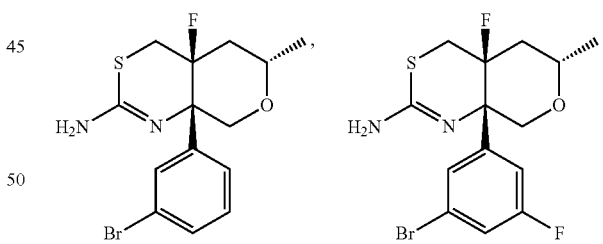

was used as starting material to replace

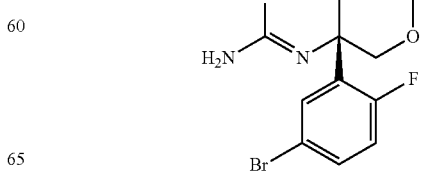

in example 8, respectively. The following compounds may be synthesized according to the procedures in example 8:
EXAMPLE 9
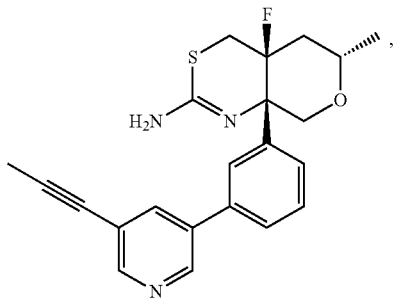
EXAMPLE 10
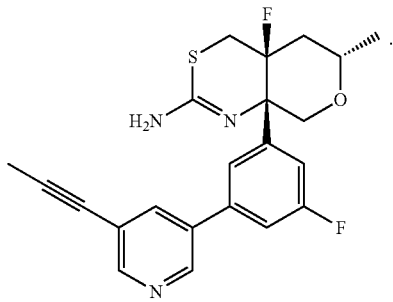
EXAMPLE 11
N-(3-((4aS,6S,8aS)-2-amino-4a-fluoro-6-methyl-4,4a,5,6,8,8a-hexahydropyrano[3,4-d][1,3]thiazin-8a-yl)-4-fluorophenyl)-5-chloropicolinamide
Its structure is:
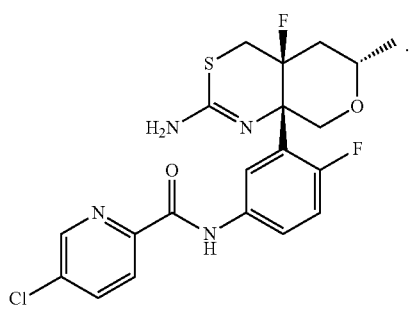 [SMILES: C[C@H]1C[C@@]2(F)CSC(N)=N[C@@]2(c2cc(NC(=O)c3ccc(Cl)cn3)ccc2F)CO1]
The synthetic route for compound of this example was as follows:
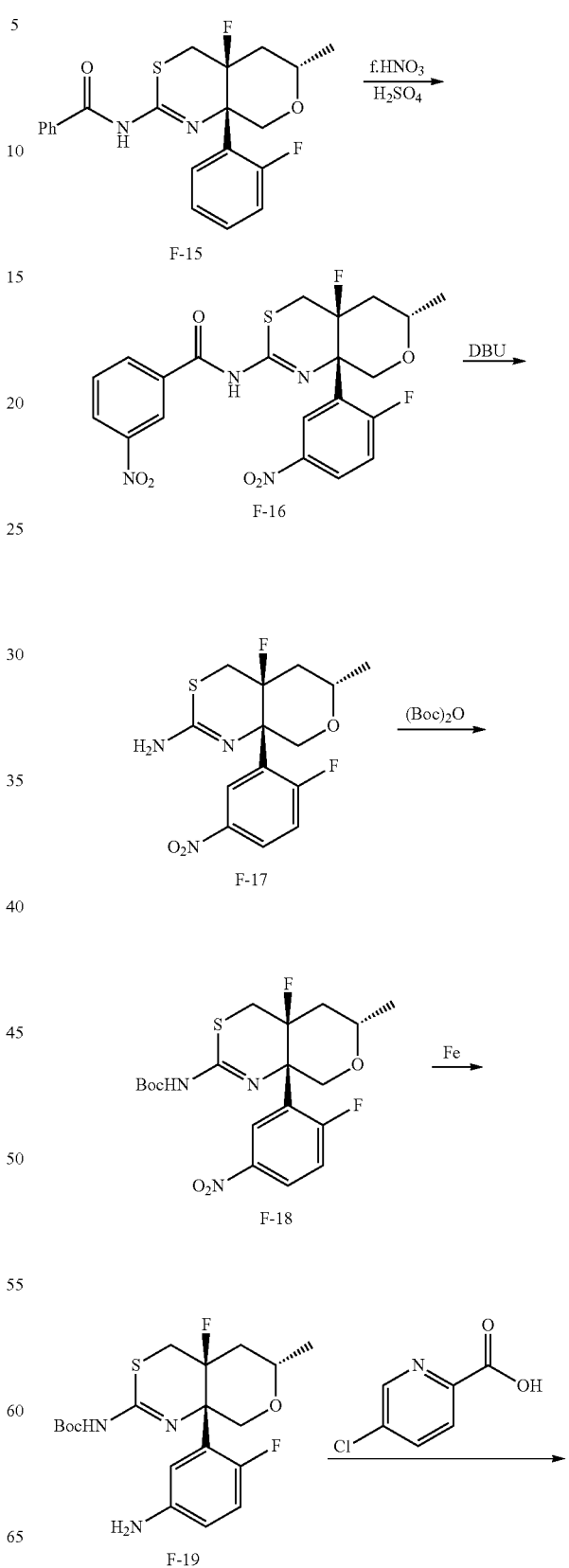

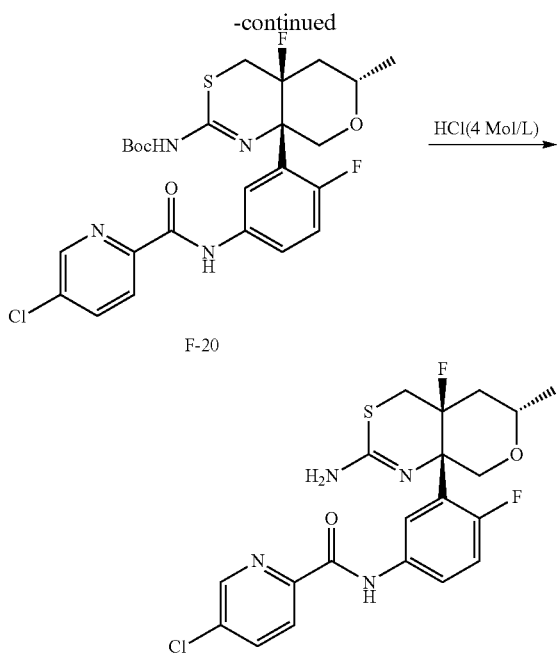

F-20

The preparation method for compound of this example included the following steps:

1) F-15, F-16, and F-17 were synthesized by referrence to example 1 and example 7, 2) Synthesis of compound F-18: F-17 (90 mg, 0.26 mmol) was dissolved in THF (10 mL), then triethylamine (216 μL, 1.56 mmol) was added, and di-tertbutyl dicarbonate (119 μL, 0.52 mmol) was added dropwise in ice-water bath. The reaction was naturally warmed to room temperature overnight. The starting material was completely reacted as indicated by TLC detection, silica gel was added, then the mixture was rotationally evaporated to dryness and passed through a column, to obtain the product (100 mg);

Nuclear magnetic resonance information for compound F-18: $^1$H-NMR (CDCl$_3$, 400 MHz) δ=8.25-8.21 (m, 2H), 7.52 (br, 1H), 7.24-7.21 (m, 1H), 4.76 (d, J=12.0 Hz, 1H), 4.07-3.98 (m, 1H), 3.82-3.79 (m, 1H), 2.85-2.79 (m, 1H), 2.52-2.24 (m, 2H), 1.94-1.86 (m, 1H), 1.52 (s, 9H), 1.30 (d, J=6.4 Hz, 3H);

3) Synthesis of compound F-19: compound F-18 (56 mg, 0.12 mmol) was dissolved in EtOH (8 mL), then saturated ammonium chloride aqueous solution (0.8 mL) was added, then powdered iron (0.5 g) was added. The mixture was heated to reflux for 3 h. The starting material was completely reacted as indicated by TLC detection, and the reaction was concentrated, extracted with dichloromethane. The organic phases were combined, dried, rotationally evaporated to dryness, and passed through a column, to obtain the product (35 mg);

Nuclear magnetic resonance information for compound F-19: $^1$H-NMR (CDCl$_3$, 400 MHz) δ=6.89-6.84 (m, 1H), 6.62-6.52 (m, 2H), 4.84-4.81 (m, 1H), 4.04-3.99 (m, 1H), 3.75 (d, J=12.0 Hz, 1H), 3.63 (br, 2H), 3.04-2.99 (m, 1H), 2.49-2.20 (m, 2H), 1.90-1.83 (m, 1H), 1.51 (s, 9H), 1.28 (d, J=6.4 Hz, 3H); 1H. 4) Synthesis of compound F-20: compound F-19 (18 mg, 0.04 mmol) was dissolved in dichloromethane (3 mL), to which 1H-benzotriazol-1-yloxytripyrrolidinophosphonium hexafluorophosphate (PyBOP) (57 mg, 0.1 mmol), diisopropylethylamine (21.6 μL, 0.13 mmol), 5-chloropyridin-2-carboxylic acid (15 mg, 0.09 mmol) were added. The mixture was reacted at room temperature overnight. The starting material was completely reacted as indicated by TLC detection. Dichloromethane (5 mL) was added, then the organic phase was washed with saturated aqueous NaCl solution. The organic phase was dried, rotationally evaporated to dryness, and passed through a column, to obtain the product (26 mg);

Nuclear magnetic resonance information for compound F-20: $^1$H-NMR (CDCl$_3$, 400 MHz) δ=9.73 (br, 1H), 8.53-8.45 (m, 1H), 8.17 (d, J=8.0 Hz, 1H), 7.96-7.68 (m, 2H), 7.30-7.28 (m, 1H), 7.07-7.02 (m, 1H), 4.77-4.74 (m, 1H), 4.00-3.95 (m, 1H), 3.76-3.59 (m, 3H), 2.98-2.93 (m, 1H), 2.46-2.17 (m, 2H), 1.88-1.84 (m, 1H), 1.46 (s, 9H), 1.22 (d, J=6.4 Hz, 3H);

5) Synthesis of N-(3-((4aS,6S,8aS)-2-amino-4a-fluoro-6-methyl-4,4a,5,6,8,8a-hexahydropyrano[3,4-d][1,3]thiazin-8a-yl)-4-fluorophenyl)-5-chloropicolinamide: F-20 (26 mg, 0.04 mmol) was dissolved in 5 mL dichloromethane, then 0.5 mL trifluoroacetic acid was added, and the mixture was reacted for 4 h at room temperature. The starting material was completely reacted by TLC detection, then the reaction solution was rotationally evaporated to dryness, to which saturated sodium carbonate aqueous solution was added, and the mixture was extracted with ethyl acetate. The organic phases were combined, dried, rotationally evaporated to dryness, and passed through a column, to obtain the product (13 mg); Nuclear magnetic resonance information: $^1$H-NMR (CDCl$_3$, 400 MHz) δ=9.73 (br, 1H), 8.50 (dd, J$_1$=0.4 Hz, J$_2$=2.4 Hz, 1H), 8.18 (dd, J$_1$=0.4 Hz, J$_2$=8.0 Hz, 1H), 7.81 (dd, J$_1$=2.4 Hz, J$_2$=8.0 Hz, 1H), 7.72-7.68 (m, 1H), 7.63-7.60 (m, 1H), 7.03-6.98 (m, 1H), 4.79 (dd, J$_1$=1.6 Hz, J$_2$=12.0 Hz, 1H), 4.01-3.96 (m, 1H), 3.75 (d, J=12.0 Hz, 1H), 3.02-2.96 (m, 1H), 2.44-2.18 (m, 2H), 1.81-1.74 (m, 1H), 1.23 (d, J=6.4 Hz, 3H); LC-MS (M+1): 453.1, 455.1.

EXAMPLE 12

In the present example, the following compound was synthesized by referring to the procedures in example 11:

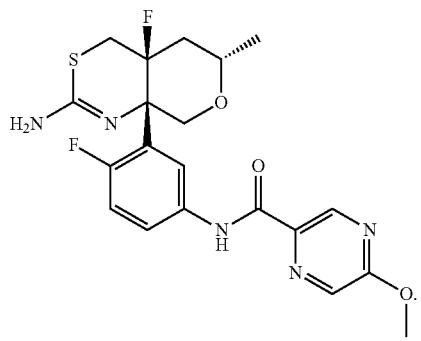 [SMILES: COc1cnc(C(=O)Nc2ccc(F)c([C@]34CO[C@@H](C)C[C@@]3(F)CSC(N)=N4)c2)cn1]

Compound of this example is synthesized as follows. Compound F-19 (50 mg, 0.12 mmol) was dissolved in 3 mL dichloromethane, to which 5-methoxypyrazin-2-carboxylic acid (25 mg, 0.16 mmol) was added, and subjected to a condensation reaction according to the conditions in step 4) of example 11. After work-up, a product was obtained; it was then subjected to the Boc-removal method in the last step of example 11 to obtain the product.

$^1$H-NMR (400 MHz, CDCl$_3$) δ 9.46 (s, 1H), 9.02 (d, J=1.3 Hz, 1H), 8.16 (d, J=1.4 Hz, 1H), 7.81-7.73 (m, 1H), 7.64 (dd, J=6.5, 2.7 Hz, 1H), 7.05 (dd, J=12.0, 8.8 Hz, 1H), 4.84 (dd, J=11.3, 1.7 Hz, 1H), 4.09-3.99 (m, 4H), 3.83 (d, J=11.3

Hz, 1H), 3.06 (dd, J=11.7, 9.1 Hz, 2H), 2.49 (dd, J=11.8, 5.1 Hz, 1H), 2.42-2.24 (m, 1H), 1.89-1.80 (m, 1H), 1.30 (d, J=6.2 Hz, 3H).
EXAMPLE 13
N-(3-((4aS,6S,8aS)-2-amino-4a-fluoro-6-methyl-4,4a,5,6,8,8a-hexahydropyrano[3,4-d][1,3]thiazin-8a-yl)phenyl)-5-chloro picolinamide
Its structure is:
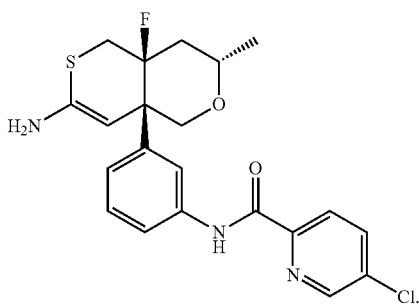 [SMILES: C[C@H]1C[C@@]2(F)CSC(N)=C[C@@]2(c2cccc(NC(=O)c3ccc(Cl)cn3)c2)CO1]
The synthetic route for compound of this example is:
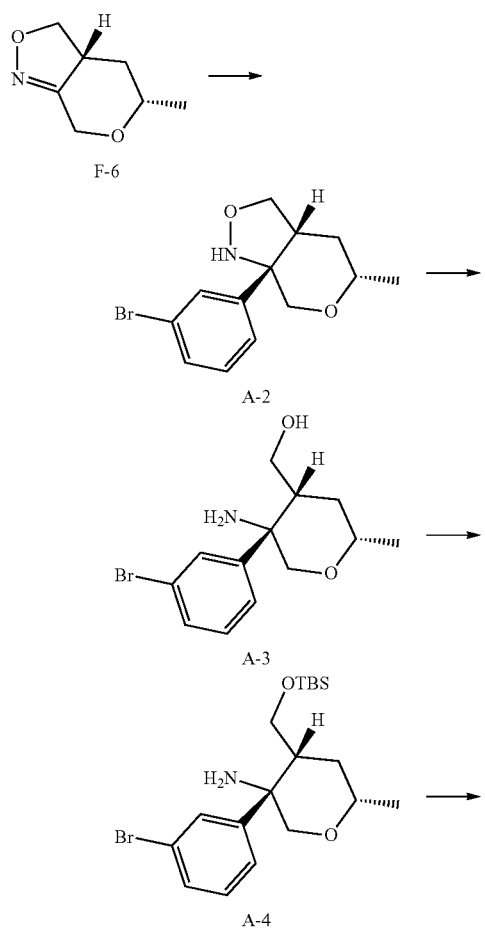
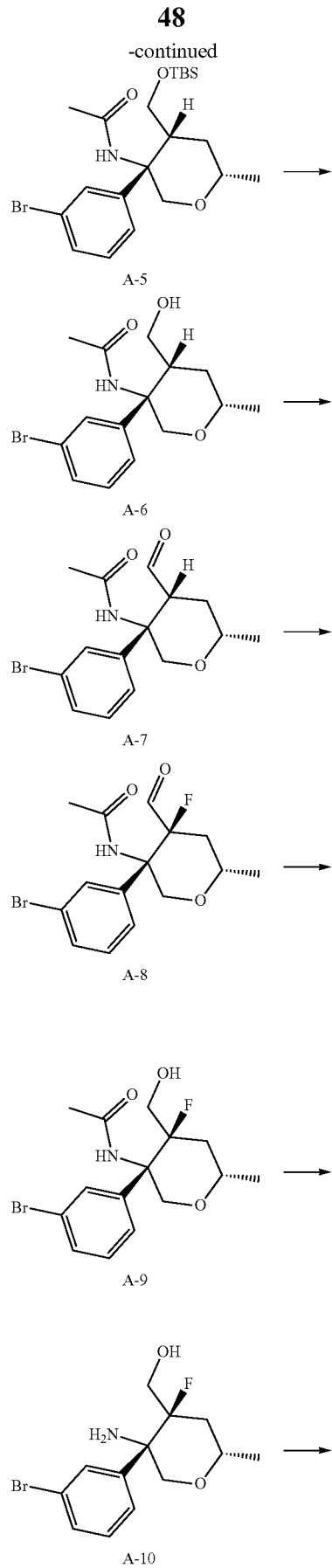

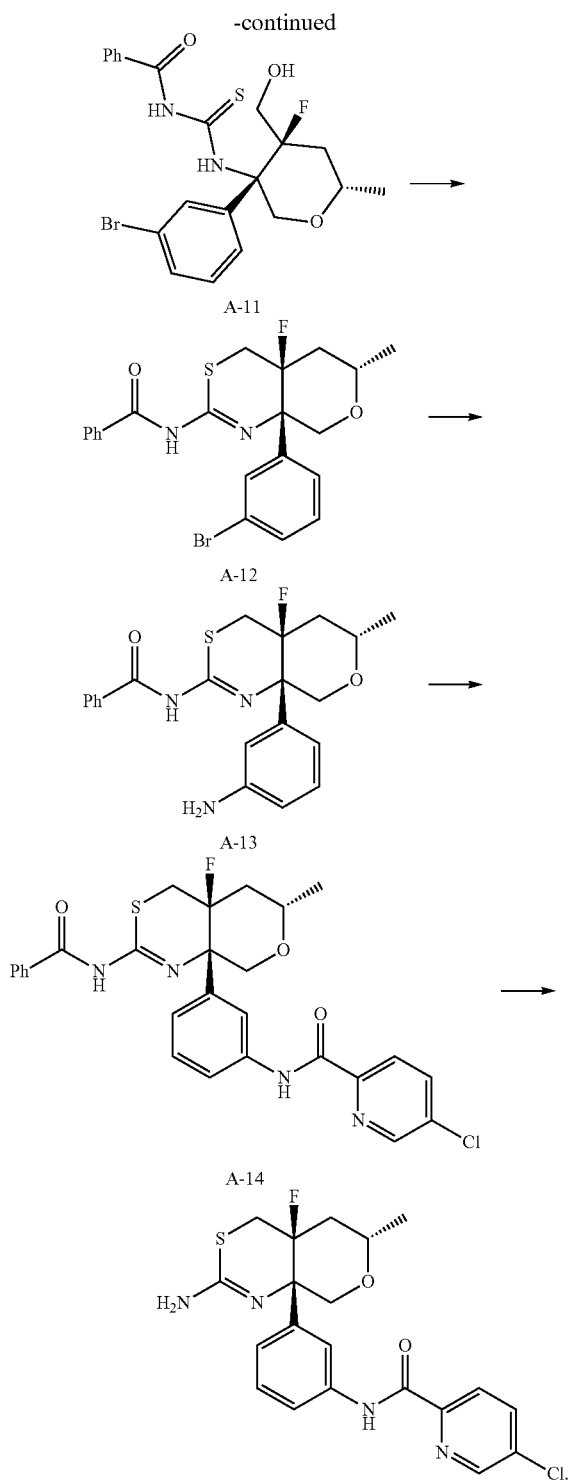

The preparation method for compound of this example includes the following steps:

1) Compounds A-2, 3, 4, 5, 6, 7, 8, 9, 10, 11, and 12 were synthesized by reference to the method in example 2;

2) Synthesis of compound A-13: A-12 (50 mg, 0.11 mmol) was dissolved in toluene (1.5 ml), to which Pd$_2$(dba)$_3$ (5.0 mg, 0.0055 mmol) and 2-(dicyclohexylphosphino)biphenyl (4.0 mg, 0.011 mmol) were then added, and lithium bis(trimethylsilyl)amide (0.32 ml, 0.32 mmol) was added dropwise at room temperature under the protection of argon gas. After completion of addition, the mixture was heated to 80° C. and reacted for 16 h. TLC detection indicated that the reaction was completed, and the mixture was naturally cooled to room temperature, then further decreased to 0° C., to which diethyl ether (2.0 ml) and 1M HCl (1.0 ml) were added and stirred for 20 min. Then the reaction mixture was adjusted to be basic with saturated sodium carbonate solution, and extracted three times with ethyl acetate. The organic phases were combined, washed twice with saturated NaCl solution, dried by anhydrous sodium sulfate, and filtered. After the filtrate was rotationally evaporated to dryness, it was purified through a column using petroleum ether and ethyl acetate, to obtain A-13 (17 mg);

Nuclear magnetic resonance information for compound A-13: $^1$H-NMR (CDCl$_3$, 400 MHz) δ=8.16 (d, J=8.0 Hz, 1H), 7.54-7.42 (m, 3H), 7.16 (t, J=8.0 Hz, 1H), 6.81-6.79 (m, 1H), 6.72-6.65 (m, 2H), 4.30 (dd, J$_1$=2.0 Hz, J$_2$=12.0 Hz, 1H), 4.14-4.05 (m, 1H), 3.76-3.73 (m, 3H), 3.11-3.05 (m, 1H), 2.59-2.55 (m, 1H), 2.43-2.26 (m, 1H), 1.93-1.86 (m, 1H), 1.29 (d, J=6.4 Hz, 3H);

3) Synthesis of compound A-14: A-13 (50 mg, 0.125 mmol) was dissolved in DCM (5 ml), to which diisopropylethylamine (62 µl, 0.375 mmol), 1H-benzotriazol-1-yloxytripyrrolidinophosphonium hexafluorophosphate (PyBOP) (163 mg, 0.313 mmol), and 5-chloropyridin-2-carboxylic acid (30 mg, 0.188 mmol) were successively added. After completion of addition, the mixture was reacted at room temperature overnight. After TLC detection indicated that the reaction was completed, the solvent was removed by rotary evaporation and the residue was purified by a column (petroleum ether and ethyl acetate as eluent), to obtain A-14 (80 mg);

Nuclear magnetic resonance information for compound A-14: $^1$H-NMR (CDCl$_3$, 400 MHz) δ=9.86 (br, 1H), 8.56-8.53 (m, 1H), 8.24 (d, J=8.0 Hz, 1H), 8.16-8.14 (m, 2H), 7.92-7.84 (m, 2H), 7.77-7.71 (m, 1H), 7.55-7.40 (m, 4H), 7.25-7.23 (m, 1H), 4.40 (dd, J$_1$=2.0 Hz, J$_2$=12.0 Hz, 1H), 4.14-4.05 (m, 1H), 3.81-3.66 (in, 3H), 3.08-3.02 (m, 1H), 2.63-2.58 (m, 1H), 2.45-2.28 (m, 1H), 1.95-19.1 (m, 1H), 1.31 (d, J=6.4 Hz, 3H);

4) Synthesis of N-(3-((4aS,6S,8aS)-2-amino-4a-fluoro-6-methyl-4,4a,5,6,8,8a-hexahydropyrano[3,4-d][1,3]thiazin-8a-yl)phenyl)-5-chloropicolinamide: A-14 (73 mg, 0.135 mmol) was dissolved in ethanol (8 ml), to which methoxyamine hydrochloride (113 mg, 1.35 mmol) and pyridine (110 µl, 1.36 mmol) were successively added at room temperature. The mixture was warmed to 50° C. and reacted overnight. After TLC detection indicated that the reaction was completed, the solvent was rotationally evaporated, and the reaction system was adjusted to be basic with saturated sodium carbonate solution, then stirred for 10 min. Then, the reaction solution was extracted with DCM, rotationally evaporated to dryness, and purified by a column (using DCM and methanol as eluent), to obtain 46 mg final product. Nuclear magnetic resonance information: $^1$H-NMR (CDCl$_3$, 400 MHz) δ=9.76 (br, 1H), 8.50 (d, J=2.0 Hz, 1H), 8.19 (d, J=8.0 Hz, 1H), 7.82-7.76 (m, 2H), 7.65 (d, J=8.0 Hz, 1H), 7.31 (t, J=8.0 Hz, 1H), 7.16 (s, 1H), 4.25 (dd, J$_1$=1.6 Hz, J$_2$=12.0 Hz, 1H), 4.04-3.99 (m, 1H), 3.68 (d, J=12.0 Hz, 1H), 2.97-2.92 (m, 1H), 2.44-2.16 (m, 2H), 1.78-1.71 (m, 1H), 1.24 (d, J=6.4 Hz, 3H); LC-MS (M+1): 435.1, 437.1.

EXAMPLE 14

N-(3-((4aS,6S,8aS)-2-amino-4a-fluoro-6-methyl-4, 4a,5,6,8,8a-hexahydropyrano[3,4-d][1,3]thiazin-8a-yl)phenyl)-5-methoxypyrazin-2-carboxamide Its structure is:

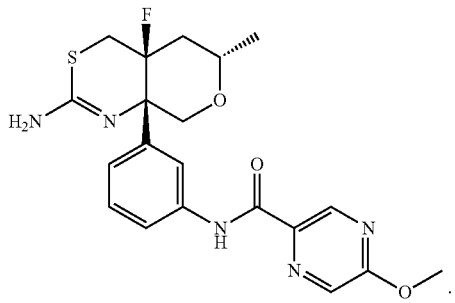 [SMILES: COc1cnc(C(=O)Nc2cccc([C@]34CO[C@@H](C)C[C@@]3(F)CSC(N)=N4)c2)cn1]

The synthetic route of compound of this example is as follows:

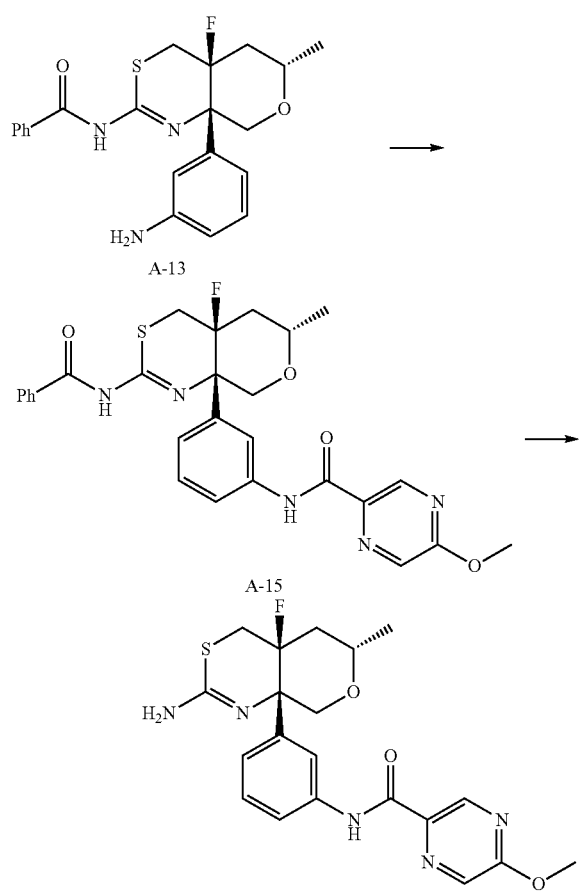

1) Synthesis of compound A-15: A-13 (50 mg, 0.125 mmol) was dissolved in DCM (5 ml), to which diisopropylethylamine (62 μl, 0.375 mmol), 1H-benzotriazol-1-yloxytripyrrolidinophosphonium hexafluorophosphate (Py-BOP) (163 mg, 0.313 mmol), and 5-methoxypyrazin-2-carboxylic acid (30 mg, 0.188 mmol) were successively added. After completion of addition, the mixture was reacted at room temperature overnight. After TLC detection indicated that the reaction was completed, the solvent was rotationally evaporated, and the residue was purified by a column (petroleum ether and ethyl acetate as eluent), to obtain A-15 (70 mg);

2) Synthesis of N-(3-((4aS,6S,8aS)-2-amino-4a-fluoro-6-methyl-4,4a,5,6,8,8a-hexahydropyrano[3,4-d][1,3]thiazin-8a-yl)phenyl)-5-methoxypyrazin-2-carboxamide: A-15 (70 mg, 0.135 mmol) was dissolved in ethanol (8 ml), to which methoxyamine hydrochloride (113 mg, 1.35 mmol) and pyridine (110 μl, 1.36 mmol) were successively added. The mixture was warmed to 50° C. and reacted overnight. After TLC detection indicated that the reaction was completed, the solvent was rotationally evaporated, and the reaction solution was adjusted to be basic with saturated sodium carbonate solution, then stirred for 10 min. Then, the reaction mixture was extracted with DCM, rotationally evaporated to dryness, and purified by a column (using DCM and methanol as eluent), to obtain 46 mg final product. Nuclear magnetic resonance information: $^1$H-NMR (400 MHz, CDCl$_3$) δ 9.51 (s, 1H), 9.04 (d, J=1.3 Hz, 1H), 8.17 (d, J=1.3 Hz, 1H), 7.83 (d, J=7.9 Hz, 1H), 7.69 (d, J=1.7 Hz, 1H), 7.38 (t, J=8.0 Hz, 1H), 7.24 (d, J=8.1 Hz, 1H), 4.32 (dd, J=11.3, 2.4 Hz, 1H), 4.14-4.01 (m, 4H), 3.74 (d, J=11.2 Hz, 1H), 3.02 (dd, J=11.4, 9.9 Hz, 1H), 2.49 (dd, J=11.5, 4.6 Hz, 1H), 2.31 (ddd, J=42.4, 14.2, 11.4 Hz, 1H), 1.86-1.76 (m, 1H), 1.31 (d, J=6.2 Hz, 3H).

EXAMPLE 15

N-(3-((4aS,6S,8aS)-2-amino-4a-fluoro-6-methyl-4, 4a,5,6,8,8a-hexahydropyrano[3,4-d][1,3]thiazin-8a-yl)phenyl)-5-methylpyrazin-2-carboxamide Its structure is:

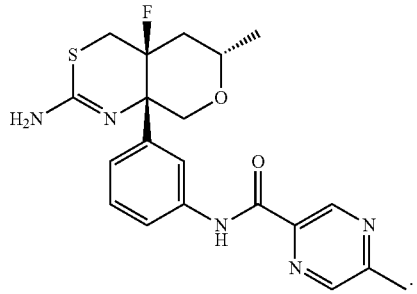 [SMILES: Cc1cnc(C(=O)Nc2cccc([C@]34CO[C@@H](C)C[C@@]3(F)CSC(N)=N4)c2)cn1]

The synthetic route of this example is:

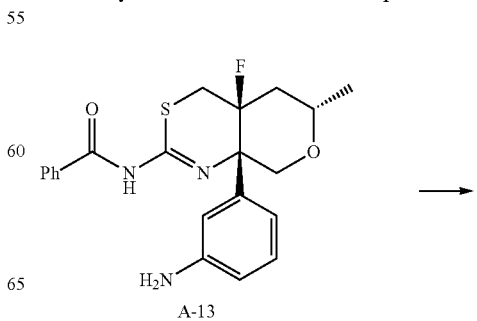

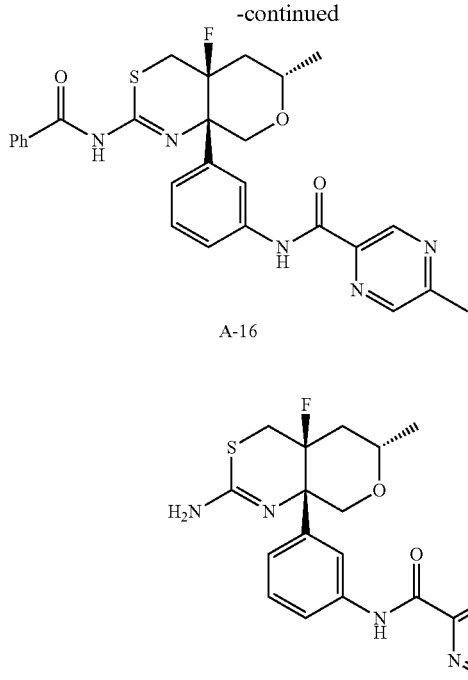

A-16

1) Synthesis of compound A-16: A-13 (50 mg, 0.125 mmol) was dissolved in DCM (5 ml), to which diisopropylethylamine (62 μl, 0.375 mmol), 1H-benzotriazol-1-yloxytripyrrolidinophosphonium hexafluorophosphate (PyBOP) (163 mg, 0.313 mmol), and 5-methylpyrazin-2-carboxylic acid (26 mg, 0.188 mmol) were successively added. After completion of addition, the mixture was reacted at room temperature overnight. After TLC detection indicated that the reaction was completed, the solvent was rotationally evaporated, and the residue was purified by a column (petroleum ether and ethyl acetate as eluent), to obtain A-16 (64 mg);

2) Synthesis of N-(3-((4aS,6S,8aS)-2-amino-4a-fluoro-6-methyl-4,4a,5,6,8,8a-hexahydropyrano[3,4-d][1,3]thiazin-8a-yl)phenyl)-5-methylpyrazin-2-carboxamide: A-16 (64 mg, 0.135 mmol) was dissolved in ethanol (8 ml), to which methoxyamine hydrochloride (113 mg, 1.35 mmol) and pyridine (110 μl, 1.36 mmol) were successively added. The mixture was warmed to 50° C. and reacted overnight. After TLC detection indicated that the reaction was completed, the solvent was rotationally evaporated, and the reaction solution was adjusted to be basic with saturated sodium carbonate solution, then stirred for 10 min. Then, the mixture was extracted with DCM, rotationally evaporated to dryness, and purified by a column (using DCM and methanol as eluent), to obtain 36 mg product;

Nuclear magnetic resonance information: $^1$H-NMR (400 MHz, CDCl$_3$) δ 9.63 (s, 1H), 9.39 (d, J=1.3 Hz, 1H), 8.45 (d, J=1.0 Hz, 1H), 7.83 (d, J=7.9 Hz, 1H), 7.73 (d, J=1.7 Hz, 1H), 7.39 (t, J=8.0 Hz, 1H), 7.25-7.20 (m, 1H), 4.32 (dd, J=11.3, 2.5 Hz, 1H), 4.14-4.01 (m, 1H), 3.75 (d, J=11.4 Hz, 1H), 3.02 (dd, J=11.4, 9.9 Hz, 1H), 2.70 (s, 3H), 2.50 (dd, J=11.5, 4.6 Hz, 1H), 2.32 (ddd, J=42.2, 14.2, 11.4 Hz, 1H), 1.86-1.77 (m, 1H), 1.3.1 (d, J=6.2 Hz, 3H).

EXAMPLE 16

N-(3-((4aS,6S,8aS)-2-amino-4a-fluoro-6-methyl-4,4a,5,6,8,8a-hexahydropyrano[3,4-d][1,3]thiazin-8a-yl)phenyl)-5-difluoromethylpyrazin-2-carboxamide Its structure is:

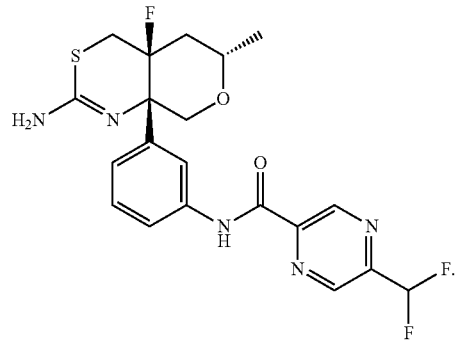 [SMILES: C[C@H]1C[C@@]2(F)CSC(N)=N[C@@]2(c2cccc(NC(=O)c3cnc(C(F)F)cn3)c2)CO1]

The synthetic route of this example is:

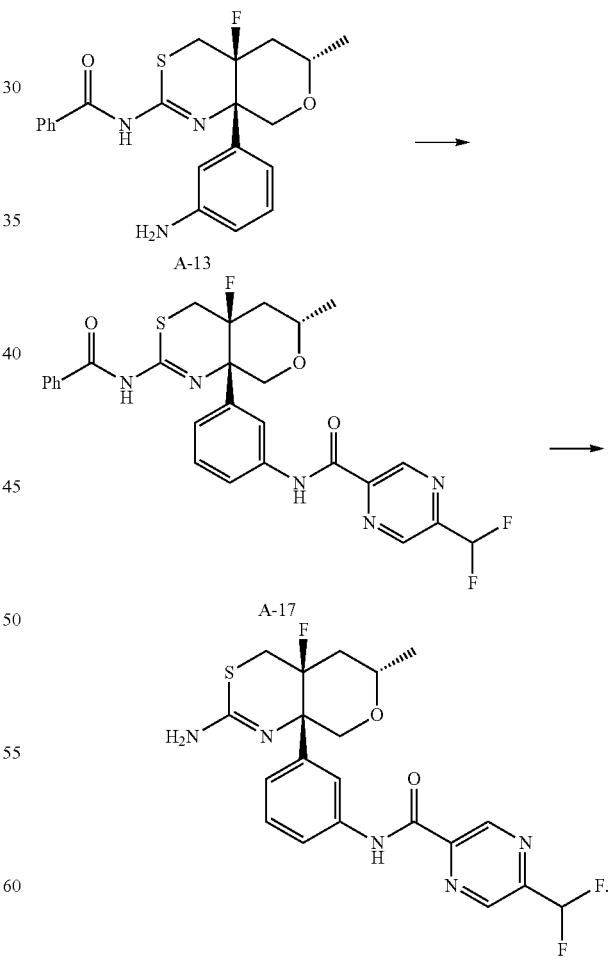

1) Synthesis of compound A-17: A-13 (50 mg, 0.125 mmol) was dissolved in DCM (5 ml), to which diisopropylethylamine (62 μl, 0.375 mmol), 1H-benzotriazol-1- yloxytripyrrolidinophosphonium hexafluorophosphate (PyBOP) (163 mg, 0.313 mmol), and 5-difluoromethylpyrazin-2-carboxylic acid (33 mg, 0.188 mmol) were successively added. After completion of addition, the mixture was reacted at room temperature overnight. After TLC detection indicated that the reaction was completed, the solvent was rotationally evaporated, and the residue was purified by a column (petroleum ether and ethyl acetate), to obtain A-17 (68 mg);

2) Synthesis of N-(3-((4aS,6S,8aS)-2-amino-4a-fluoro-6-methyl-4,4a,5,6,8,8a-hexahydropyrano[3,4-d][1,3]thiazin-8a-yl)phenyl)-5-difluoromethylpyrazin-2-carboxamide:
A-17 (68 mg, 0.122 mmol) was dissolved in ethanol (8 ml), to which methoxyamine hydrochlorate (113 mg, 1.35 mmol) and pyridine (110 µl, 1.36 mmol) were successively added. The mixture was warmed to 50° C. and reacted overnight. After TLC detection indicated that the reaction was completed, the solvent was rotationally evaporated, and the reaction system was adjusted to be basic with saturated sodium carbonate solution, then stirred for 10 min. Then, the mixture was extracted with DCM, rotationally evaporated to dryness, and purified by a column (using DCM and methanol), to obtain 36 mg product; Nuclear magnetic resonance information: $^1$H-NMR (400 MHz, CDCl$_3$) δ 9.64 (s, 1H), 9.53 (s, 1H), 8.92 (s, 1H), 7.82 (d, J=8.0 Hz, 1H), 7.73 (s, 1H), 7.39 (t, J=8.0 Hz, 1H), 7.29 (d, J=7.4 Hz, 1H), 6.79 (t, J=54.5 Hz, 1H), 4.31 (dd, J=11.4, 2.3 Hz, 1H), 4.16-4.01 (m, 1H), 3.75 (d, J=11.3 Hz, 1H), 3.01 (dd, J=11.3, 10.1 Hz, 1H), 2.51 (dd, J=11.5, 4.5 Hz, 1H), 2.31 (ddd, J=42.3, 14.2, 11.4 Hz, 1H), 1.88-1.76 (m, 1H), 1.31 (d, J=6.2 Hz, 3H).

EXAMPLE 17

N-(3-((4aS,6S,8aS)-2-amino-4a-fluoro-6-methyl-4,4a,5,6,8,8a-hexahydropyrano[3,4-d][1,3]thiazin-8a-yl)-4-fluorophenyl)-5-difluoromethylpyrazin-2-carboxamide Its structure is:

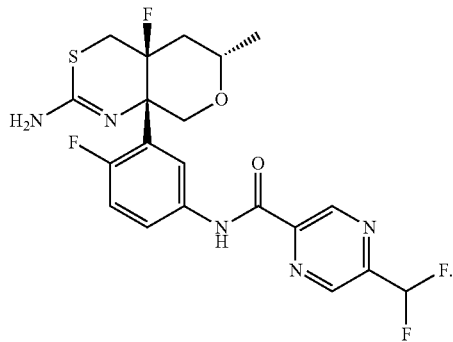 [SMILES: C[C@H]1C[C@@]2(F)CSC(N)=N[C@@]2(c2cc(NC(=O)c3cnc(C(F)F)cn3)ccc2F)CO1]

The synthetic route of this example is as follows:

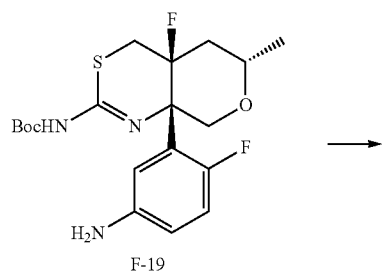

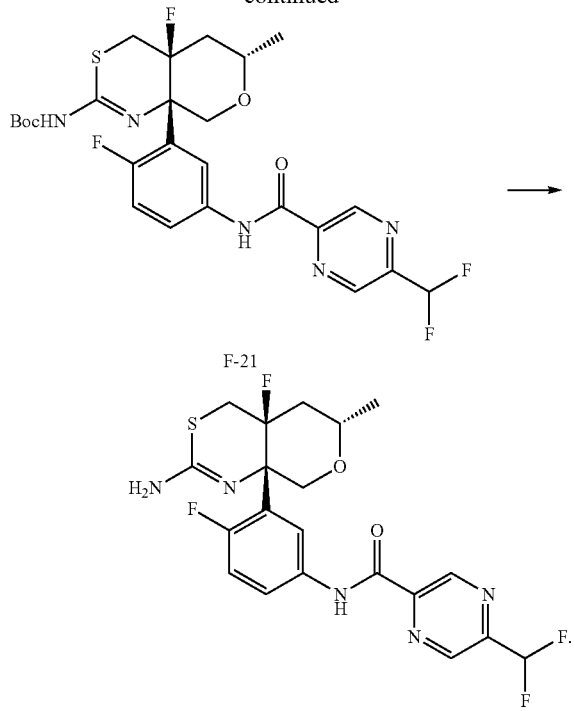

1) Synthesis of compound F-21: compound A-19 (18 mg, 0.04 mmol) was dissolved in dichloromethane (3 mL), to which 1H-benzotriazol-1-yloxytripyrrolidinophosphonium hexafluorophosphate (PyBOP) (57 mg, 0.1 mmol), diisopropylethylamine (21.6 µl, 0.13 mmol), and 5-difluoromethylpyrazin-2-carboxylic acid (16 mg, 0.09 mmol) were successively added. After completion of addition, the mixture was reacted at room temperature overnight. After TLC detection indicated that the reaction was completed, dichloromethane (5 mL) was added, then the organic phase was washed with saturated aqueous NaCl solution, dried, rotationally evaporated to dryness, and passed through a column, to obtain the product (23 mg);

2) Synthesis of N-(3-((4aS,6S,8aS)-2-amino-4a-fluoro-6-methyl-4,4a,5,6,8,8a-hexahydropyrano[3,4-d][1,3]thiazin-8a-yl)-4-fluorophenyl)-5-difluoromethylpyrazin-2-carboxamide: compound F-21 (23 mg, 0.03 mmol) was dissolved in dichloromethane (5 ml), to which 0.5 mL trifluoroacetic acid was then added, and the mixture was reacted for 4 h at room temperature. The reaction was completed as indicated by TLC, then the reaction solution was rotationally evaporated to dryness, and saturated Na$_2$CO$_3$ aqueous solution was added. The mixture was extracted with ethyl acetate. The organic phases were combined, dried, rotationally evaporated to dryness, and passed through a column, to obtain the product (13 mg); Nuclear magnetic resonance information: $^1$H-NMR (400 MHz, CDCl$_3$) δ 9.62 (s, 1H), 9.53 (s, 1H), 8.93 (s, 1H), 7.82-7.64 (m, 2H), 7.09 (dd, J=11.8, 8.8 Hz, 1H), 6.79 (t, J=54.4 Hz, 1H), 4.85 (d, J=11.8 Hz, 1H), 4.14-3.98 (m, 1H), 3.84 (d, J=11.3 Hz, 1H), 3.14-2.99 (m, 1H), 2.51 (dd, J=11.8, 5.2 Hz, 1H), 2.43-2.23 (m, 1H), 1.93-1.78 (m, 1H), 1.31 (d, J=6.2 Hz, 3H); LC-MS (M+1): 470.3.

EXAMPLE 18
N-(3-((4aS,6S,8aS)-2-amino-4a-fluoro-6-methyl-4,4a,5,6,8,8a-hexahydropyrano[3,4-d][1,3]thiazin-8a-yl)-5-fluorophenyl)-5-methoxypyrazin-2-carboxamide
The reaction procedures and work-up of each step can refer to the synthetic method of example 13, and the detailed synthetic route is as follows:
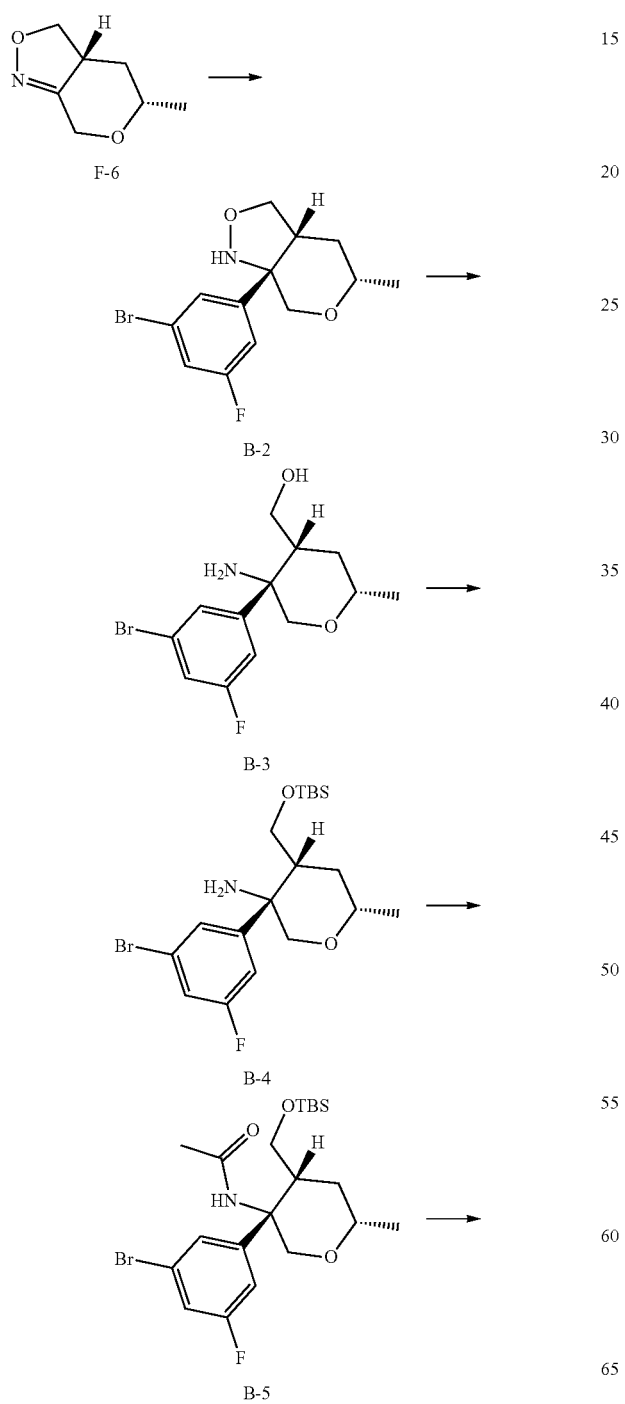
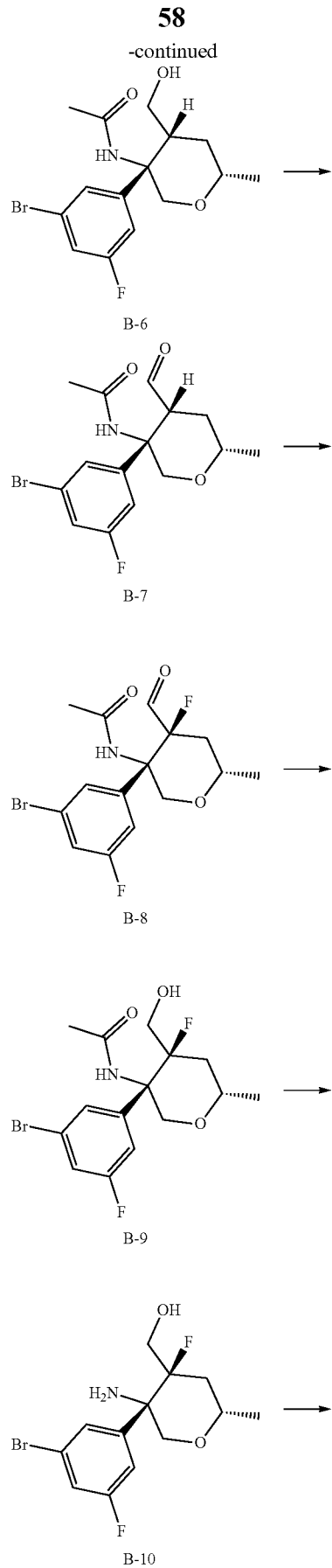

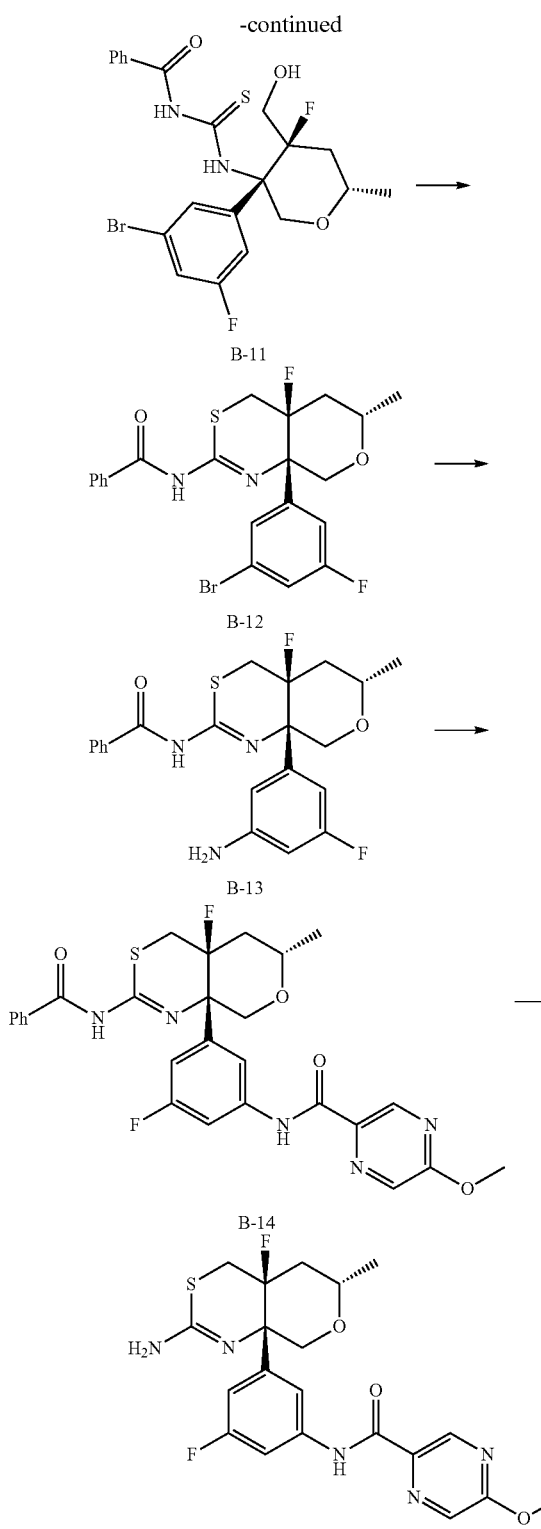

$J_1$=4.30 Hz, $J_2$=11.45 Hz, 1H), 2.38-2.03 (m, 1H), 1.86-1.80 (m, 1H), 1.44-1.42 (d, J=6.49 Hz, 2H), 1.32-1.31 (d, J=6.19 Hz, 3H).

EXAMPLE 19

N-(3-((4aS,6S,8aS)-2-amino-4a-fluoro-6-methyl-4,4a,5,6,8,8a-hexahydropyrano[3,4-d][1,3]thiazin-8a-yl)-4-fluorophenyl)-5-methylpyrazin-2-carboxamide Its structure is:

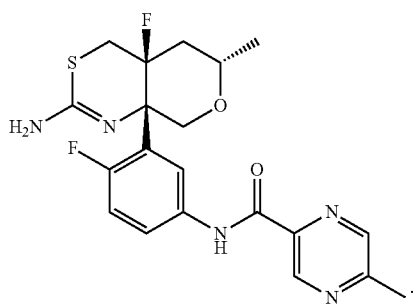 [SMILES: Cc1cnc(C(=O)Nc2ccc(F)c([C@]34CO[C@@H](C)C[C@@]3(F)CSC(N)=N4)c2)cn1]

The synthetic route for compound of this example is as follows:

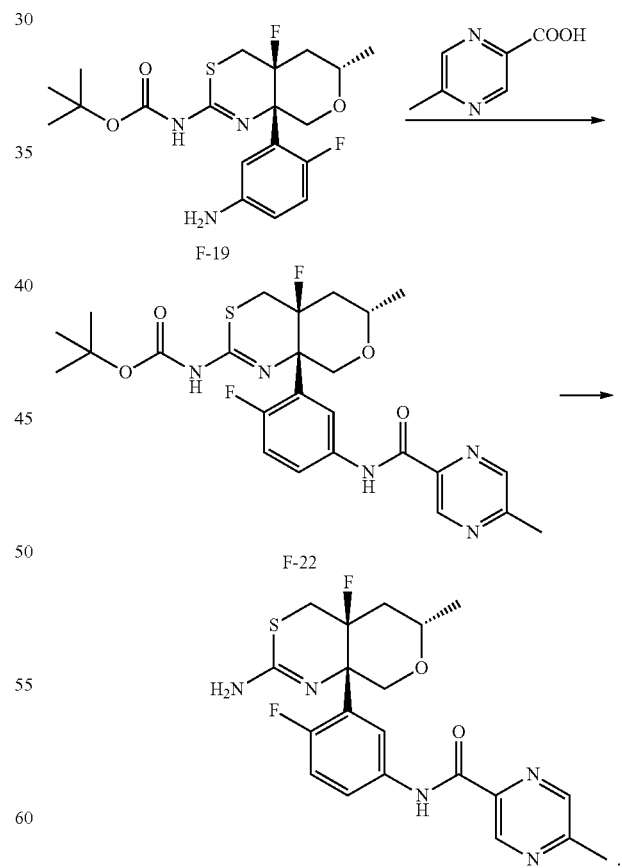

NMR data of N-(3((4aS,6S,8aS)-2-amino-4a-fluoro-6-methyl-4,4a,5,6,8,8a-hexahydropyrano[3,4-d][1,3]thiazin-8a-yl)-5-fluorophenyl)-5-methoxypyrazin-2-carboxamide is as follows: $^1$H-NMR (CDCl$_3$, 400 MHz) δ=9.56 (s, 1H), 9.02-9.02 (d, J=1.17 Hz, 1H), 8.16-8.16 (d, J=1.17 Hz, 1H), 7.81-7.79 (m, 1H), 7.34 (s, 1H), 6.98-6.95 (m, 1H), 4.25-4.21 (dd, $J_1$=2.35 Hz, $J_2$=11.45 Hz, 1H), 4.11-4.05 (m, 5H), 3.78-3.75 (d, J=11.40 Hz), 3.06-3.01 (t, 1H), 2.57-2.53 (dd, Wherein synthesis of F-19 referred to example 11, synthesis of F-22 referred to example 17. The carboxylic acid condensed with F-19 should be replaced by 5-methylpyrazin-2-carboxylic acid, and the experimental procedures and the work-up for Boc-removal was the same as step 2) in example 17, to provide the product N-(3-((4aS,6S,8aS)-2-amino-4a-fluoro-6-methyl-4,4a,5,6,8,8a-hexahydro-pyrano[3,4-d][1,3]thiazin-8a-yl)-4-fluorophenyl)-5-methylpyrazin-2-carboxamide; Nuclear magnetic resonance information: $^1$H-NMR (CDCl$_3$, 400 MHz) δ=9.51 (s, 1H), 9.32-9.31 (d, 1.18 Hz), 8.40 (s, 1H), 7.73-7.63 (m, 2H), 6.97-6.91 (q, 1H), 4.84-4.81 (dd, J$_1$=1.19 Hz, J$_2$=11.20 Hz, 1H), 4.06-4.02 (m, 1H), 3.85-3.82 (d, J=11.26 Hz, 1H), 3.03-2.97 (m, 1H), 2.67 (s, 3H), 2.49-2.45 (m, 1H), 2.40-2.23 (m, 1H), 1.86-1.79 (m, 1H), 1.29-1.27 (d, J=6.06 Hz, 3H); MS [M+H] 434.1.

EXAMPLES 20-22

Referring to the experimental procedures and the work-up of example 17, the carboxylic acid condensed with F-19 was replaced by

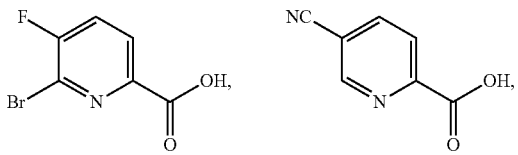

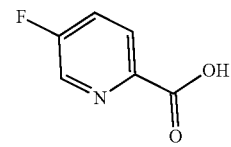

respectively to synthesize the compounds shown in Table 2:

TABLE 2

Compounds of examples 20-22

| Ex. | Structure of compound | Structural Characterization |
|---|---|---|
| 20 | | $^1$H-NMR (CDCl$_3$, 400 MHz) δ = 9.44 (s, 1H), 8.29-8.26 (dd, J$_1$ = 3.68 Hz, J$_2$ = 8.28 Hz, 1H), 7.72-7.66 (m, 2H), 7.63-7.59 (q, 1H), 7.02-6.97 (q, 1H), 4.97 (br, 2H), 4.85-4.82 (dd, J$_1$ = 1.29 Hz, J$_2$ = 11.29 Hz, 1H), 4.09-4.04 (m, 1H), 3.86-3.83 (d, J = 11.88 Hz), 3.06-3.01 (q, 1H), 2.51-2.47 (dd, J$_1$ = 5.04 Hz, J$_2$ = 11.80 Hz, 1H), 2.42-2.25 (m, 1H), 1.88-1.81 (m, 1H), 1.31-1.29 (d, J = 5.9 Hz, 3H); MS [M +H] 515.0. |
| 21 | | $^1$H-NMR (CDCl$_3$, 400 MHz) δ = 9.81 (s, 1H), 8.91 (s, 1H), 8.45-8.43 (dd, J$_1$ = 0.73 Hz, J$_2$ = 8.11 Hz, 1H), 8.22-8.19 (dd, J$_1$ = 2.14 Hz, J$_2$ = 8.14 Hz, 1H), 7.80-7.77 (m, 1H), 7.71-7.69 (q, 1H), 7.11-6.05 (q, 1H), 4.87-4.84 (dd, J$_1$ = 1.83 Hz, J$_2$ = 11.30 Hz, 1H), 4.08-4.04 (m, 1H), 3.84-3.81 (d, J = 11.30 Hz), 3.10-3.02 (q, 1H), 2.52-2.48 (dd, J$_1$ = 4.89 Hz, J$_2$ = 11.9 Hz, 1H), 2.42-2.25 (m, 1H), 1.89-1.82 (m, 1H), 1.31-1.30 (d, J = 6.11 Hz, 3H); MS [M + H] 441.1. |
| 22 | | $^1$H-NMR (CDCl$_3$, 400 MHz) δ = 9.76 (s, 1H), 8.46-8.45 (d, J = 2.85 Hz, 1H), 8.35-8.32 (q, 1H), 7.80-7.76 (m, 1H), 7.68-7.66 (dd, J$_1$ = 2.65 Hz, J$_2$ = 6.52 Hz, 1H), 7.62-7.57 (m, 1H), 7.08-7.03 (q, 1H), 4.87-4.84 (dd, J$_1$ = 1.72 Hz, J$_2$ = 11.29 Hz, 1H), 4.09-4.04 (m, 1H), 3.86-3.83 (d, J = 11.45 Hz), 3.09-3.03 (m, 1H), 2.53-2.48 (dd, J$_1$ = 5.03 Hz, J$_2$ = 11.73 Hz, 1H), 2.42-2.25 (m, 1H), 1.89-1.83 (m, 1H), 1.31-1.29 (d, J = 6.09 Hz, 3H); MS [M + H] 437.1. |

EXAMPLES 23-27

Referring to the synthetic method of example 14, the "A substituted by halogen" for addition with F-6 was replaced by

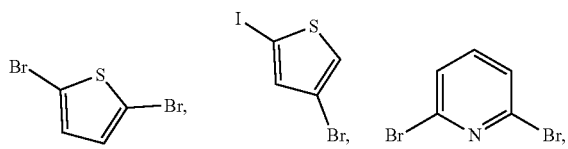

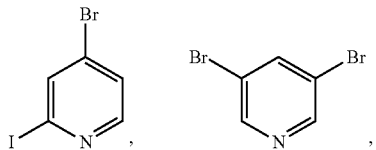

respectively to synthesize compounds of examples 23-27, as shown in Table 3 below;

TABLE 3

Compounds of examples 23-27

| Ex. | Structure of compound | MS & ¹H-NMR |
|---|---|---|
| 23 | | MS [M + H]: 437.51;<br>¹H-NMR (400 MHz, CDCl₃) δ 9.40 (s, 1H), 9.07 (d, J = 1.3 Hz, 1H), 8.15 (d, J = 1.3 Hz, 1H), 6.84-6.83 (d, J = 3.38 Hz, 1H), 6.78-6.77 (d, J = 3.38 Hz, 1H), 4.30 (dd, J = 11.3, 2.4 Hz, 1H), 4.10-4.02 (m, 4H), 3.76 (d, J = 11.2 Hz, 1H), 3.08 (dd, J = 11.4, 9.9 Hz, 1H), 2.49 (dd, J = 11.5, 4.6 Hz, 1H), 2.33 (ddd, J = 42.4, 14.2, 11.4 Hz, 1H), 1.88-1.76 (m, 1H), 1.31 (d, J = 6.2 Hz, 3H) |
| 24 | | MS [M + H]: 437.51 |
| 25 | | MS [M + H]: 432.47<br>¹H-NMR (400 MHz, CDCl₃) δ 9.51 (s, 1H), 9.04 (d, J = 1.3 Hz, 1H), 8.17 (d, J = 1.3 Hz, 1H), 7.76-7.62 (m, 1H), 7.56-7.52 (t, 1H), 7.37-7.35 (m, 1H), 4.34 (dd, J = 11.3, 2.4 Hz, 1H), 4.14-4.02 (m, 4H), 3.74 (d, J = 11.2 Hz, 1H), 3.02 (dd, J = 11.4, 9.9 Hz, 1H), 2.49 (dd, J = 11.5, 4.6 Hz, 1H), 2.33 (ddd, J = 42.4, 14.2, 11.4 Hz, 1H), 1.86-1.76 (m, 1H), 1.30 (d, J = 6.2 Hz, 3H) |

TABLE 3-continued
Compounds of examples 23-27
| Ex. | Structure of compound | MS & ¹H-NMR |
|---|---|---|
| 26 | 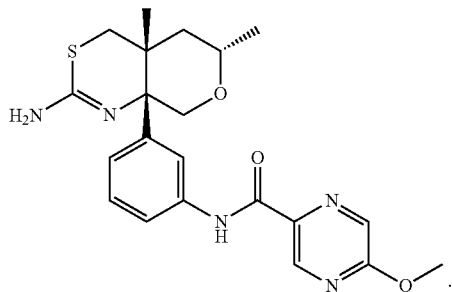 | MS [M + H]: 432.47 |
| 27 | | MS [M + H]: 432.47 |
EXAMPLE 28
Structure of the Compound is:
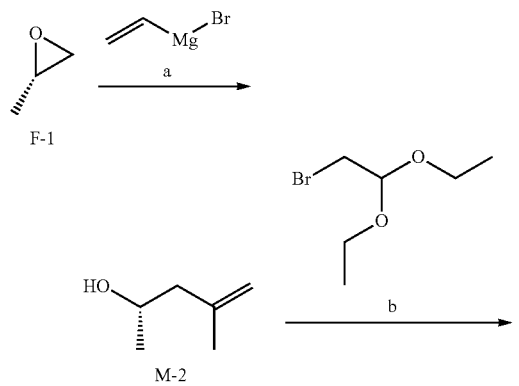
The synthetic route is as follows:
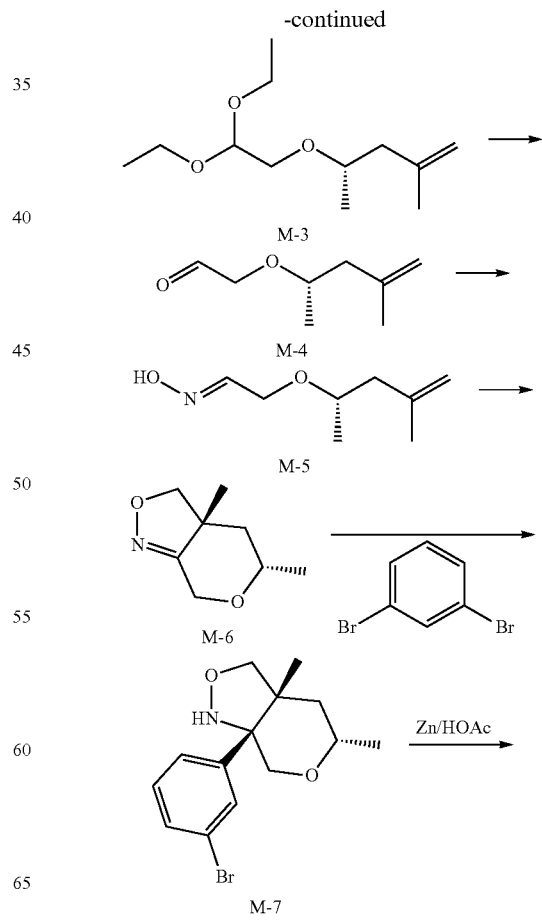

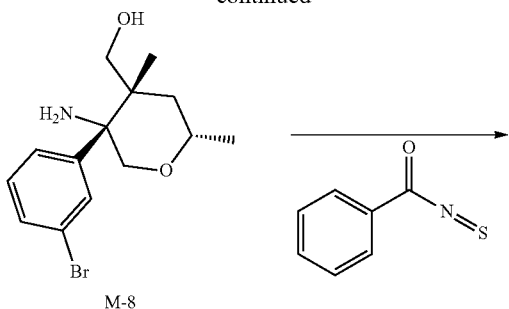

M-8

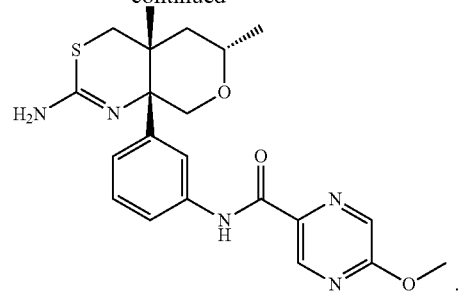

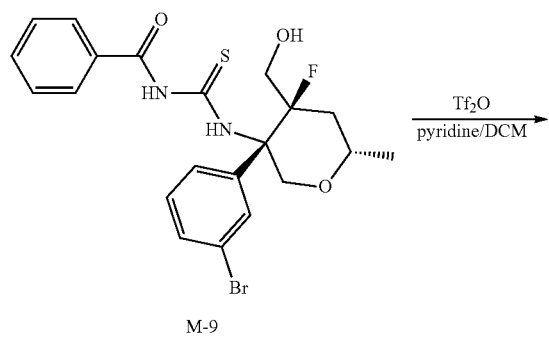

M-9

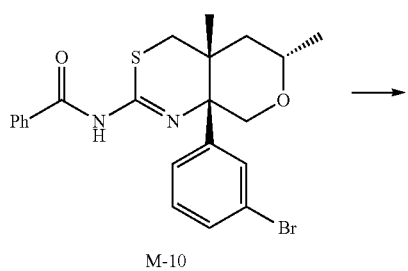

M-10

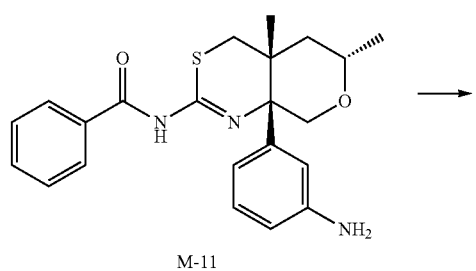

M-11

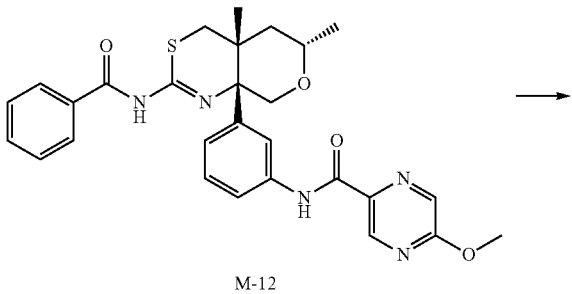

M-12

The preparation method for compound of this example includes the following steps:

1) Synthesis of compound M-2: S-epoxypropane (5.81 g, 0.10 mol) was added to anhydrous diethyl ether, then purged with argon and the temperature was decreased to −78° C. CuI (1.08 g, 0.006 mol) was added under argon gas, and the mixture was stirred for 30 min, then isopropenyl magnesium bromide (54.5 mL, 0.11 mol) was added dropwise at −78° C. The system temperature was kept at −78° C.~75° C. After completion of addition, the mixture was stirred at this temperature for 30 min, then naturally warmed to room temperature, and continually stirred for 18 h. The reaction solution was decreased to 0° C., then 50 mL ammonium chloride aqueous solution was added to quench the reaction. The mixture was extracted with diethyl ether (100 mL×3), and the organic phases were combined, dried, rotationally evaporated to dryness, and directly used in the next step;

2) Synthesis of compound M-3: the crude product obtained in the above step was added in 250 mL THF, and the mixture was decreased to 0° C. under argon gas, then NaH (17.6 g, 0.44 mol) was added batchwise. After completion of addition, the reaction was carried out at 0° C. for one hour, then warmed to room temperature, and the reaction was carried out for additional 1 h, then decreased to 0° C. again. Bromoacetaldehyde diethyl acetal (28.6 g, 0.145 mol) was added dropwise, and after completion of addition, the mixture was naturally warmed to room temperature, then heated to reflux. After reacting for 15 h, the temperature was decreased to 0° C. again, and Bromoacetaldehyde diethyl acetal (28.6 g, 0.145 mol) was added dropwise, then the reaction was heated to reflux for 10 h. After the completion of reaction, the temperature was decreased to 0° C., and ammonium chloride aqueous solution was added to quench the reaction. The organic phase was extracted with ethyl acetate (200 mL×3), and the organic phases were combined, dried, rotationally evaporated to dryness, and roughly passed through a column, then subjected to distillation, to obtain the product (13.6 g), with a total yield of 60% for two steps;

Nuclear magnetic resonance information for compound M-3: $^1$H-NMR (CDCl$_3$, 400 MHz) δ=4.78-4.70 (m, 2H), 4.59 (t, J=5.29 Hz, 1H), 3.74-3.42 (m, 7H), 2.36-2.31 (m, 1H), 2.09-2.04 (m, 1H), 1.26-1.20 (m, 9H), 1.15 (d, J=6.27 Hz, 3H); GC-MS: 216.2;

3) Synthesis of compound M-4: compound M-3 (13.6 g, 0.0629 mol) was dissolved in 150 mL THF, to which 2 mol/L HCl aqueous solution (37.4 mL) was then added dropwise at room temperature. After completion of addition, the reaction solution was heated to 55° C. and stirred for 1 h. After the reaction was completed, the temperature was decreased to room temperature, and the reaction solution was rotationally evaporated to half of the volume (the temperature of water bath in rotatory evaporator was below 35° C.), then ethyl acetate and water at a volume ratio of 1:1 were added. The phases were separated, and the aqueous phase was extracted with ethyl acetate (50 mL×3); the organic phases were combined, dried, rotationally evaporated to dryness, and directly used in the next step;

4) Synthesis of compound M-5: the crude product M-4 obtained in the above step was dissolved in EtOH/H$_2$O (200 mL/70 mL), then hydroxylamine hydrochloride (14.7 g, 21.1 mmol) and sodium acetate (28.8 g, 351.5 mmol) were added batchwise. After completion of addition, the mixture was heated to 60° C. and reacted for 10 h, and the reaction was completed by GC detection, to which 500 mL ethyl acetate and 100 mL water were added. The phases were separated, and the organic phase was dried, rotationally evaporated to dryness, passed through a column (PE~PE:EA=100~5:1), to obtain the product (2.0 g), with a total yield of 20% for two steps.

Nuclear magnetic resonance information for compound M-5: $^1$H-NMR (CDCl$_3$, 400 MHz) δ=7.50-7.47 (m, 0.5 H), 6.91-6.87 (m, 0.51), 4.81-4.73 (m, 2H), 4.44-4.30 (m, 1H), 4.21-4.04 (m, 1H), 3.67-3.59 (m, 1H), 2.38-2.30 (m, 1H), 2.11-2.04 (m, 1H), 1.74 (s, 3H), 1.16 (d, J=6.20 Hz, 3H); MS (M+1)=158.2;

5) Synthesis of compound M-6: compound M-5 (2.0 g, 12.7 mol) was dissolved in 60 mL dichloromethane, then placed in the water bath at room temperature, to which triethylamine (0.3 g, 3.0 mol) was added, then sodium hypochlorite aqueous solution (70 mL) was added dropwise. During the process of addition, the temperature of the system was kept no more than 25° C. After completion of addition, the reaction was stirred at room temperature overnight, and after completion of the reaction, the solution was stood for separation of phases. The organic phase was washed with saturated aqueous NaCl solution, and the organic phase was dried, rotationally evaporated to dryness, and passed through a column (PE~PE:EA=100~5:1), to obtain 0.2 g product, with a yield of 10%;

Nuclear magnetic resonance information for compound M-6: $^1$H-NMR (CDCl$_3$, 400 MHz) δ=4.56 (d, J=13.2 Hz, 1H), 4.24 (dd, J=2.96 Hz, 10.8 Hz, 2H), 3.85-3.73 (in, 2H), 1.98-1.88 (m, 1H), 1.75-1.62 (m, 1H), 1.34 (s, 3H), 1.24 (d, J=6.00 Hz, 3H); GC-MS: 155.2;

6) Compounds M-7 and M-8 were synthesized by reference to the operation steps and the experimental methods for compounds F-7 and F-8 in steps 7) and 8) of example 1;

7) Compounds M-9 and M-10 were synthesized by reference to the operation steps and the experimental methods for compounds F-14 and F-15 in steps 13) and 14) of example 1;

8) Compounds M-11, M-12, and the final product were synthesized by referrence to the operation steps and the experimental methods in example 14.

Effect Test

The activity assay for the compound of each example was carried out in this experimental example, and the detailed test method was as follows:

1. The test compound was formulated as 10 μmol/L solution in dimethylsulfoxide;

2. Starting from 10 μmol/L, by 3-fold serial dilution, the inhibitory activity of each compound against the enzyme was tested in singlet state at 10 doses;

3. IC$_{50}$ values of test compounds were finally obtained. Test results are shown in Table 4.

TABLE 4

| Activity test results of compounds | | |
|---|---|---|
| Compound | Compound | BACE1 (IC$_{50}$/nM) |
| Example 7 | 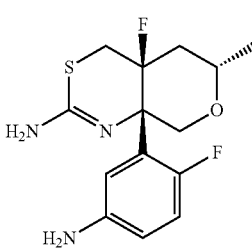 [SMILES: C[C@H]1C[C@@]2(F)CSC(N)=N[C@@]2(c2cc(N)ccc2F)CO1] | 5870 |
| Example 11 | 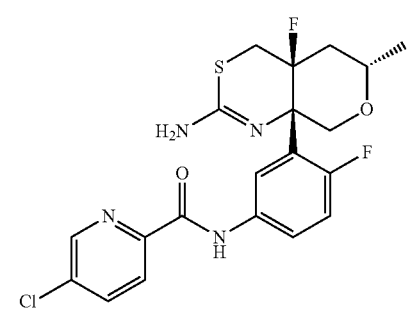 [SMILES: C[C@H]1C[C@@]2(F)CSC(N)=N[C@@]2(c2cc(NC(=O)c3ccc(Cl)cn3)ccc2F)CO1] | 172 |

TABLE 4-continued

Activity test results of compounds

| Compound | Compound | BACE1 (IC$_{50}$/nM) |
| --- | --- | --- |
| Example 12 | | 150 |
| Example 13 | | 213 |
| Example 14 | | 130 |
| Example 15 | | 225 |

TABLE 4-continued

Activity test results of compounds

| Compound | Compound | BACE1 (IC$_{50}$/nM) |
|---|---|---|
| Control Example (Control sample B-Secretase inhibitor IV) | 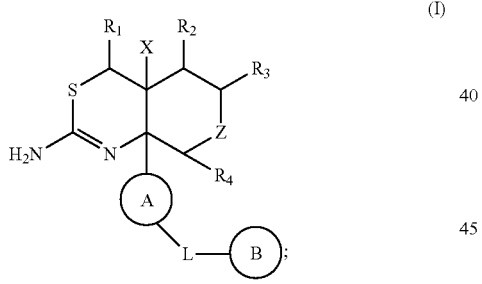 | 266 |

According to the results in Table 4, it can be seen that the synthesized compounds had very good inhibitory effect on BACE1, and most of them had higher activity than the control sample B-secretase inhibitor IV, the best one had about 2-fold higher activity. Thus, compounds of the present invention are very good BACE inhibitors, have a good prospect as potent drugs, and thus can be used to improve the current situation that the effective drugs are significantly shortage in treating Alzheimer's disease.

The invention claimed is:

1. Compound of formula (I), or a pharmaceutically acceptable salt, or stereoisomer thereof:

(I)

in formula (I), A is $C_{6-14}$ aryl, or $C_{6-14}$ aryl substituted by 1~4 substituents, or 5~6 membered heteroaryl, or 5~6 membered heteroaryl substituted by 1~4 substituents, or 9~10 membered benzo-fused heteroaryl, or 9~10 membered benzo-fused heteroaryl substituted by 1~4 substituents; said substituents are optionally selected from Group 1;

L is a single bond, oxygen atom, sulfur atom, —$NR_5$—, —$NR_5CO$—, —$NR_5COR_6$—, —$NR_5CONR_5$—, —$NR_5COO$—, —$NR_5SO_2$—, —$NR_5SO$—, or $C_{1-6}$ alkylene, or $C_{1-6}$ alkylene substituted by 1~3 substituents, or $C_{2-6}$ alkenylene, or $C_{2-6}$ alkenylene substituted by 1~3 substituents, or $C_{2-6}$ alkynylene, or $C_{2-6}$ alkynylene substituted by 1~3 substituents; wherein, $R_5$ is hydrogen atom, or $C_{1-6}$ alkyl, or $C_{1-6}$ alkyl substituted by 1~3 substituents; $R_{1-6}$ is $C_{1-6}$ alkyl, or $C_{1-6}$ alkyl substituted by 1~3 substituents; said substituents are optionally selected from Group 1;

B is $C_{1-6}$ alkyl, or $C_{1-6}$ alkyl substituted by 1~3 substituents, or $C_{3-8}$ cycloalkyl, or $C_{3-8}$ cycloalkyl substituted by 1~3 substituents, or $C_{6-14}$ aryl, or $C_{6-14}$ aryl substituted by 1~4 substituents, or 5~10 membered heteroaryl, or 5~10 membered heteroaryl substituted by 1~4 substituents; said substituents are optionally selected from Group 1;

$R_1$, $R_2$, and $R_4$ are independently from each other hydrogen atom, halogen atom, hydroxyl, amino, alkylamino, or $C_{1-6}$ alkyl, or $C_{1-6}$ alkyl substituted by 1~3 substituents, or $C_{1-6}$ alkoxyl, or $C_{1-6}$ alkoxyl substituted by 1~3 substituents, or 3~10 membered carbocyclic group, or 3~10 membered carbocyclic group substituted by 1~3 substituents, or $C_{6-14}$ aryl, or $C_{6-14}$ aryl substituted by 1~4 substituents, or 5~10 membered heteroaryl, or 5~10 membered heteroaryl substituted by 1~4 substituents; said substituents are optionally selected from Group 1;

$R_3$ is hydrogen atom, halogen atom, hydroxyl, amino, alkylamino, or $C_{1-6}$ alkyl, or $C_{1-6}$ alkyl substituted by 1~3 substituents, or $C_{1-6}$ alkoxyl, or $C_{1-6}$ alkoxyl substituted by 1~3 substituents, or 3~10 membered carbocyclic group, or 3~10 membered carbocyclic group substituted by 1~3 substituents, or $C_{1-4}$ aryl, or $C_{1-4}$ aryl substituted by 1~4 substituents, or 5~10 membered heteroaryl, or 5~10 membered heteroaryl substituted by 1~4 substituents; said substituents are optionally selected from Group 1;

Z is O, S, sulfoxide, sulfone, or —$NR_7$—, wherein $R_7$ is hydrogen atom, or $C_{1-6}$ alkyl, or $C_{1-6}$ alkyl substituted by 1~3 substituents, or $C_{6-14}$ aryl, or $C_{6-14}$ aryl substituted by 1~4 substituents, or 5~10 membered heteroaryl, or 5~10 membered heteroaryl substituted by 1~4 substituents; said substituents are optionally selected from Group 1;

Group 1 is hydrogen atom, halogen atom, hydroxyl, amino, cyano, amido, sulfonamido, difluoromethyl, trifluoromethyl, trifluoromethoxyl, $C_{1-6}$ alkylthio, $C_{1-6}$ alkoxyl, $C_{6-14}$ aryl, $C_{6-14}$ aryloxy, $C_{6-14}$ aryloxycarbonyl, $C_{6-14}$ arylcarbonyl, $C_{3-8}$ cycloalkyloxycarbonyl, $C_{3-8}$ cycloalkyl, $C_{3-8}$ cycloalkylthio, $C_{1-6}$ alkyl, $C_{1-6}$ alkylamino, $C_{1-6}$ alkylcarbonyl, $C_{2-6}$ alkenyl, $C_{2-6}$ alkynyl, 5~10 membered heteroaryl, or 5~10 membered heteroarylcarbonyl;

X is F, Cl, Br, or I or $C_{1-4}$ alkyl, or $C_{1-4}$ alkyl substituted by 1~4 substituents; said substituents are optionally selected from Group 1;

the structure of formula (I) contains L and B, or does not contain L and B.

2. The compound according to claim 1, or a pharmaceutically acceptable salt, or stereoisomer thereof, which is compound of formula (II), or a pharmaceutically acceptable salt, or stereoisomer thereof:

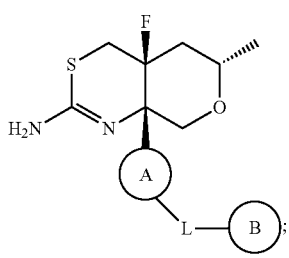

(II)

in formula (II), A is $C_{6-14}$ aryl, or $C_{6-14}$ aryl substituted by 1~4 substituents, or 5~6 membered heteroaryl, or 5~6 membered heteroaryl substituted by 1~4 substituents, or 9~10 membered benzo-fused heteroaryl, or 9~10 membered benzo-fused heteroaryl substituted by 1~4 substituents; said substituents are optionally selected from Group 1;

L is a single bond, oxygen atom, sulfur atom, —NR—, —NR$_5$CO—, —NR$_5$COR$_6$—, —NR$_5$CONR$_5$—, —NR$_5$COO—, —NR$_5$SO$_2$—, —NR$_5$SO—, or $C_{1-6}$ alkylene, or $C_{1-6}$ alkylene substituted by 1~3 substituents, or $C_{2-6}$ alkenylene, or $C_{2-6}$ alkenylene substituted by 1~3 substituents, or $C_{2-6}$ alkynylene, or $C_{2-6}$ alkynylene substituted by 1~3 substituents; wherein, R$_5$ is hydrogen atom, or $C_{1-6}$ alkyl, or $C_{1-6}$ alkyl substituted by 1~3 substituents; R$_6$ is $C_{1-6}$ alkyl, or $C_{1-6}$ alkyl substituted by 1~3 substituents; said substituents are optionally selected from Group 1;

B is $C_{1-6}$ alkyl, or $C_{1-6}$ alkyl substituted by 1-3 substituents or $C_{3-8}$ cycloalkyl, or $C_{3-8}$ cycloalkyl substituted by 1~3 substituents, or $C_{6-14}$ aryl, or $C_{1-14}$ aryl substituted by 1~4 substituents, or 5~10 membered heteroaryl, or 5~10 membered heteroaryl substituted by 1~4 substituents; said substituents are optionally selected from Group 1;

Group 1 is hydrogen atom, halogen atom, hydroxyl, amino, cyano, amido, sulfonamido, difluoromethyl, trifluoromethyl, trifluoromethoxyl, $C_{1-6}$ alkylthio, $C_{1-6}$ alkoxyl, $C_{6-14}$ aryl, $C_{6-14}$ aryloxy, $C_{6-14}$ aryloxycarbonyl, $C_{6-14}$ arylcarbonyl, $C_{3-8}$ cycloalkyloxyl carbonyl, $C_{3-8}$ cycloalkyl, $C_{3-8}$ cycloalkylthio, $C_{1-6}$ alkyl, $C_{1-6}$ alkylamino, $C_{1-6}$ alkylcarbonyl, $C_{2-6}$ alkenyl, $C_{2-6}$ alkynyl, 5~10 membered heteroaryl, or 5~10 membered heteroarylcarbonyl;

the structure of formula (II) contains L and B, or does not contain L and B.

3. The compound according to claim 1, or a pharmaceutically acceptable salt, or stereoisomer thereof, in which A is phenyl, or phenyl substituted by 1~4 substituents, or 5~6 membered heteroaryl, or 5~6 membered heteroaryl substituted by 1~4 substituents; said substituents are optionally selected from the group consisting of halogen atom, amino, cyano, difluoromethyl, trifluoromethyl, trifluoromethoxyl, $C_{1-6}$ alkoxyl, $C_{1-6}$ alkyl, and $C_{1-6}$ alkylamino.

4. The compound according to claim 1, or a pharmaceutically acceptable salt, or stereoisomer thereof, in which L is a single bond, or oxygen atom, or —NH—, or —NHCO—, or —NR$_5$SO$_2$—; B is 5~6 membered heteroaryl, or 5~6 membered heteroaryl substituted by 1~4 substituents; wherein, R$_5$ is hydrogen atom, or $C_{1-6}$ alkyl, or $C_{1-6}$ alkyl substituted by 1~3 substituents; said substituents are optionally selected from the group consisting of halogen atom, amino, cyano, difluoromethyl, trifluoromethyl, trifluoromethoxyl, $C_{1-6}$ alkoxyl, $C_{1-6}$ alkyl, $C_{2-6}$ alkynyl, and $C_{1-6}$ alkylamino.

5. The compound according to claim 3, or a pharmaceutically acceptable salt, or stereoisomer thereof, in which L is a single bond, or oxygen atom, or —NH—, or —NHCO—, or —NR$_5$SO$_2$—; B is 5~6 membered heteroaryl, or 5~6 membered heteroaryl substituted by 1~4 substituents; wherein, R$_5$ is hydrogen atom, or $C_{1-6}$ alkyl, or $C_{1-6}$ alkyl substituted by 1~3 substituents; said substituents are optionally selected from the group consisting of halogen atom, amino, cyano, difluoromethyl, trifluoromethyl, trifluoromethoxyl, $C_{1-6}$ alkoxyl, $C_{1-6}$ alkyl, $C_{2-6}$ alkynyl, and $C_{1-6}$ alkylamino.

6. The compound according to claim 1, or a pharmaceutically acceptable salt, or stereoisomer thereof, in which said compounds are selected from the group consisting of:

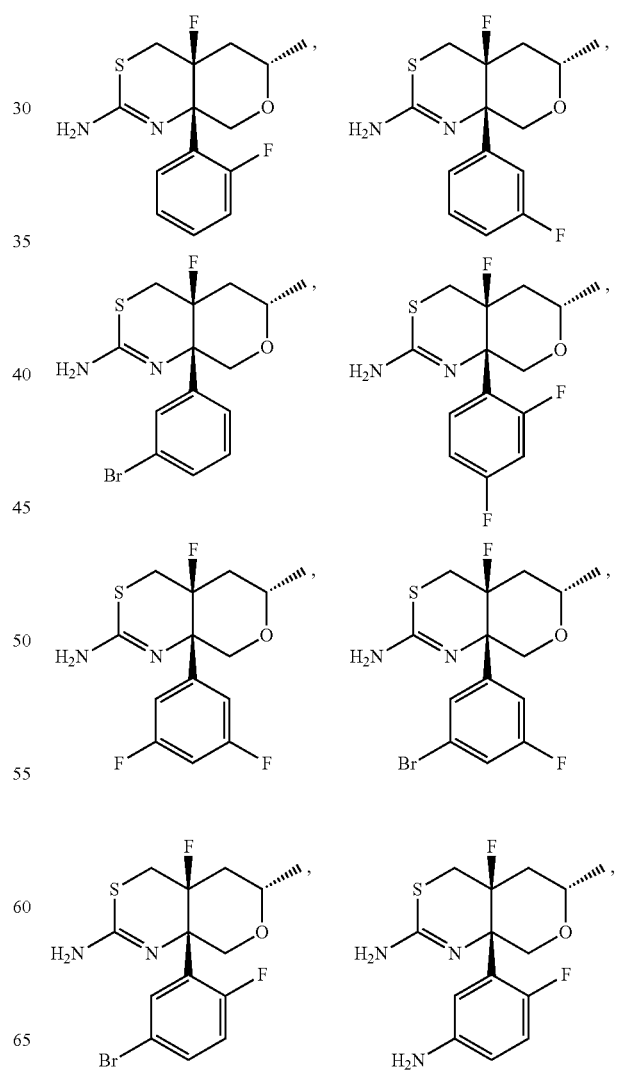

77
-continued
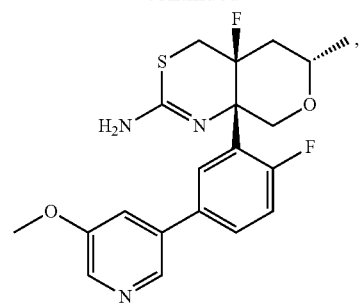
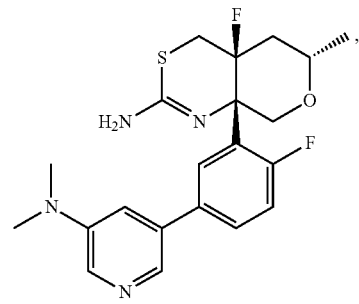
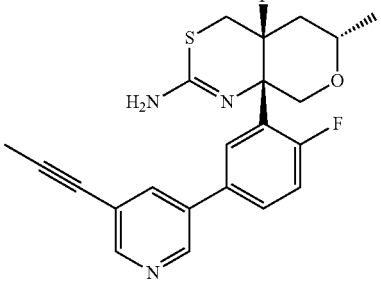
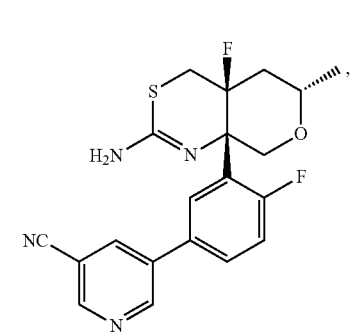
78
-continued
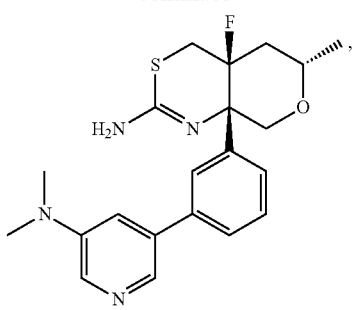
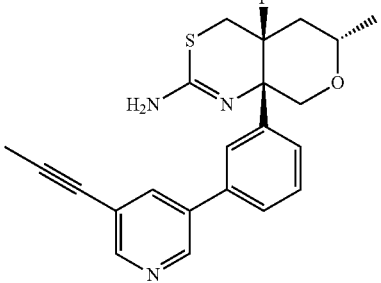
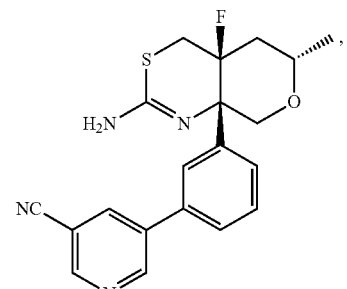
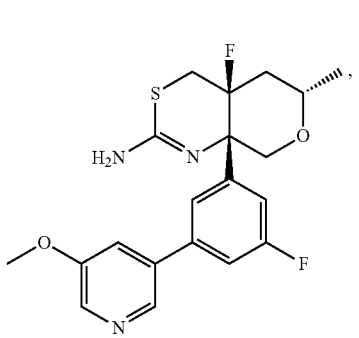
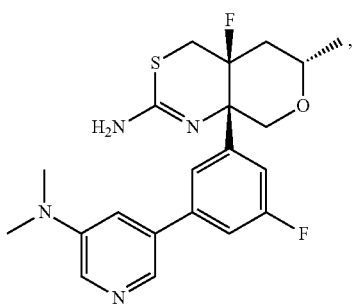

-continued
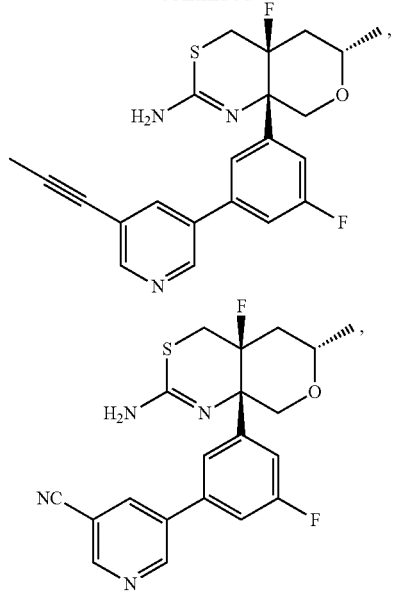
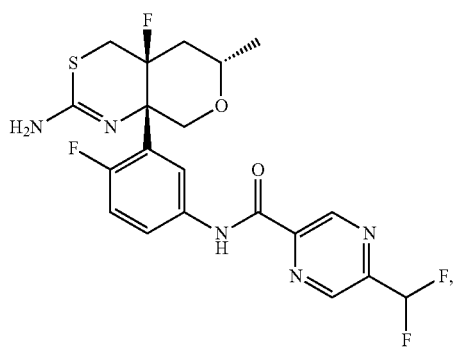
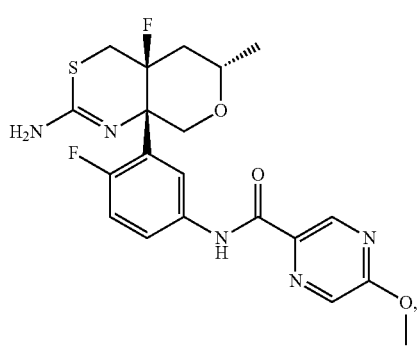
-continued
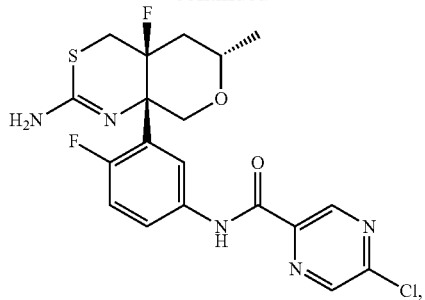
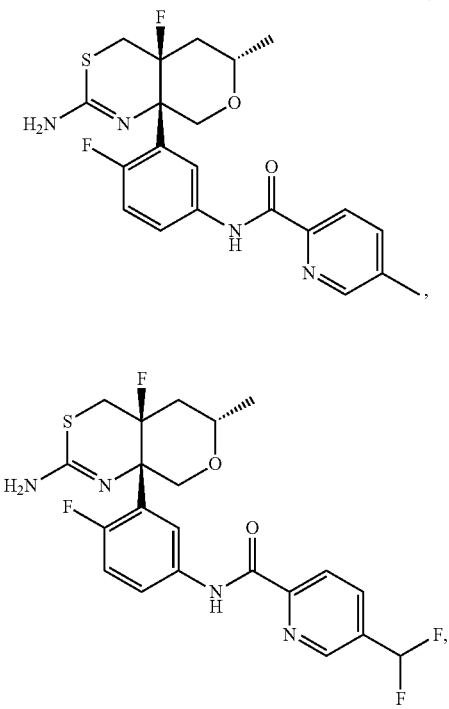
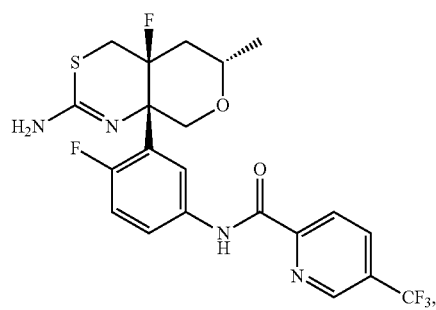

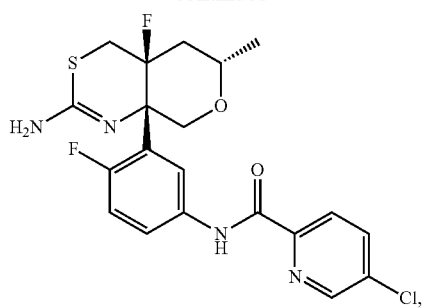
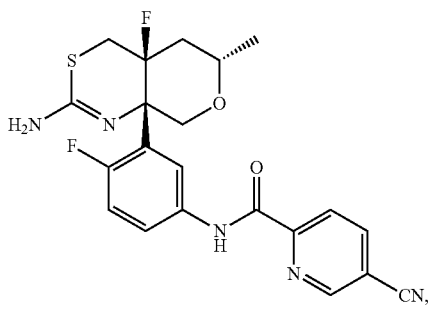
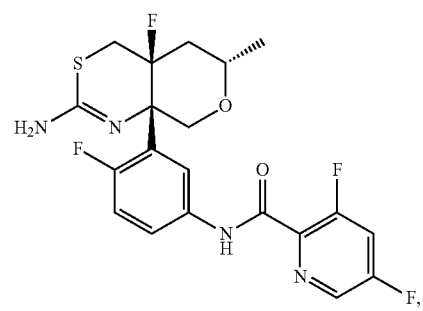
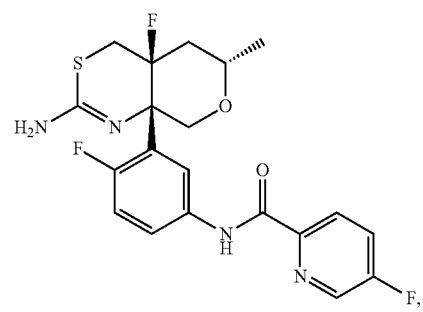
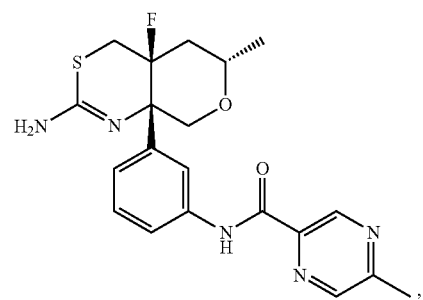
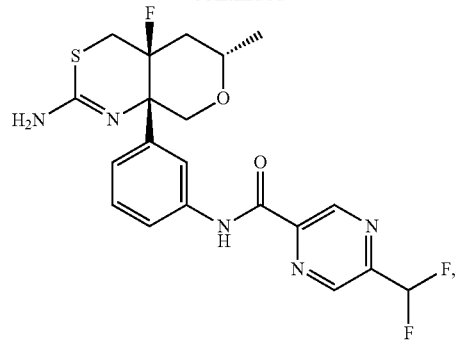
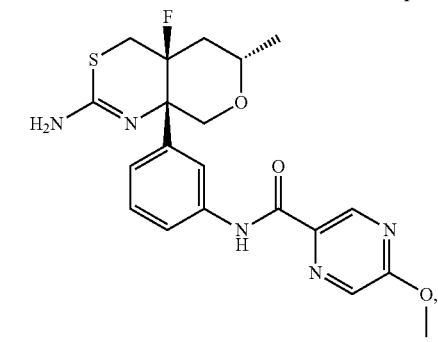
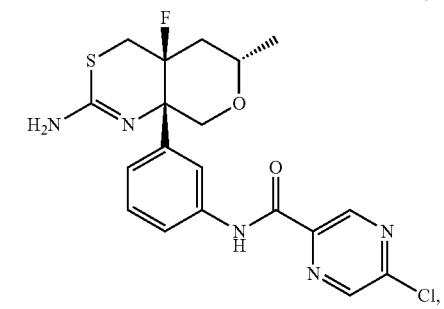
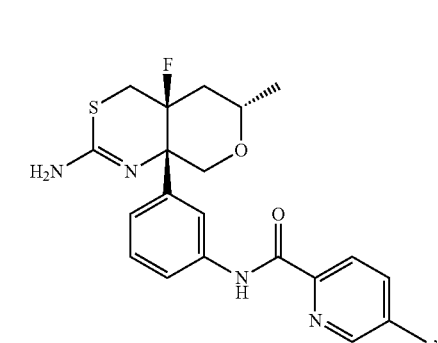
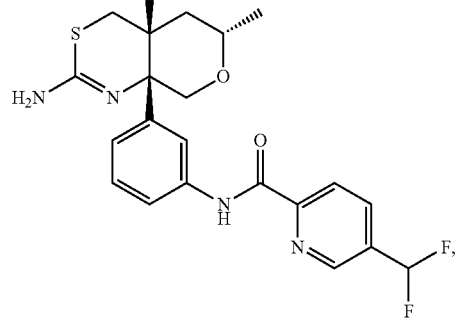

83
-continued
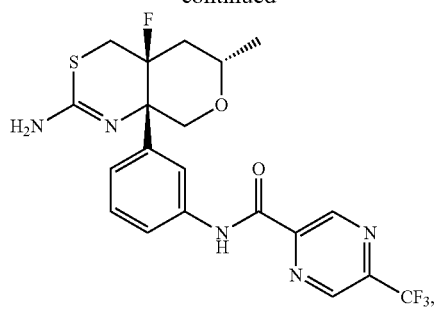
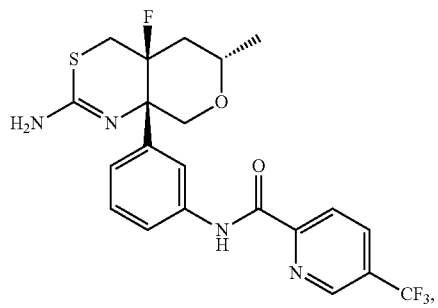
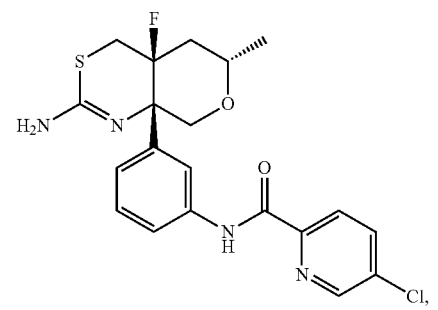
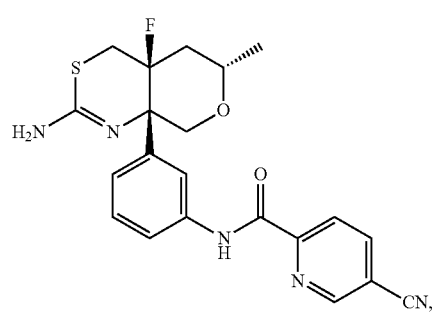
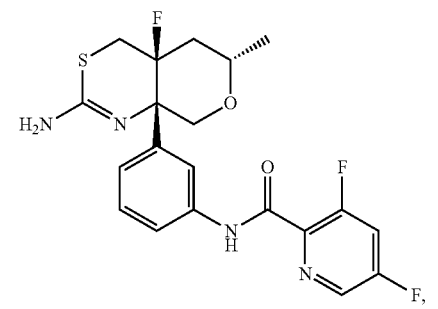
84
-continued
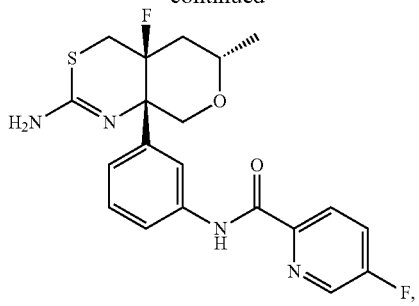
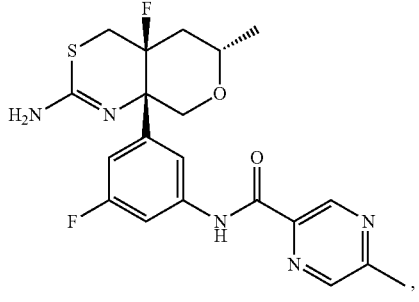
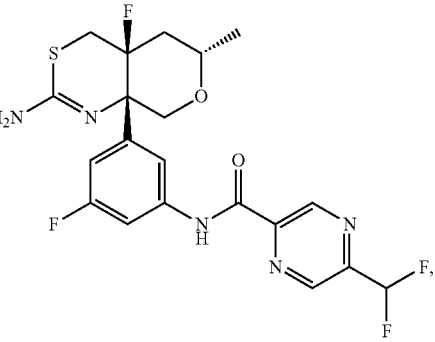
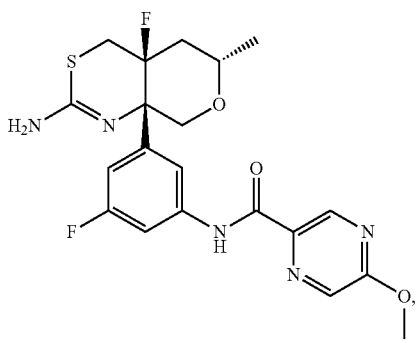
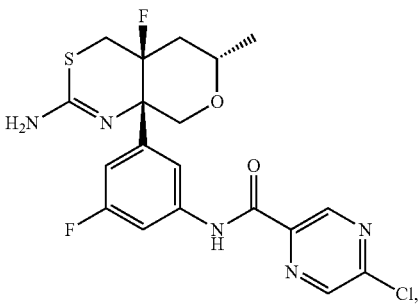

85
-continued
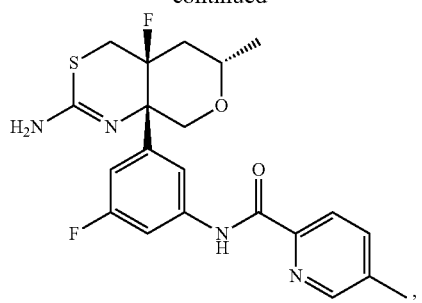
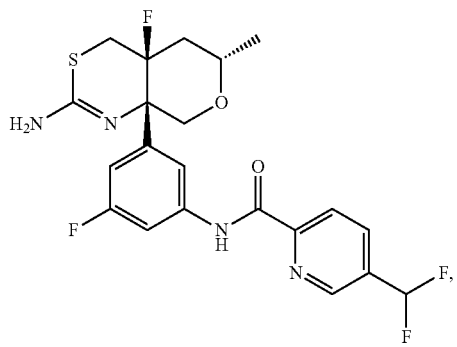
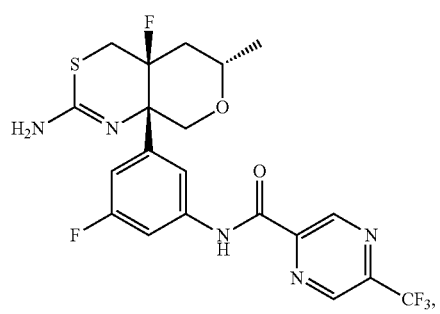
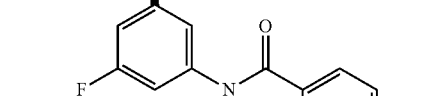
86
-continued
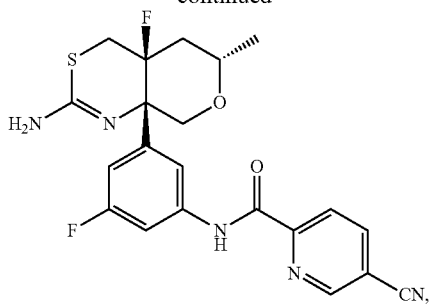
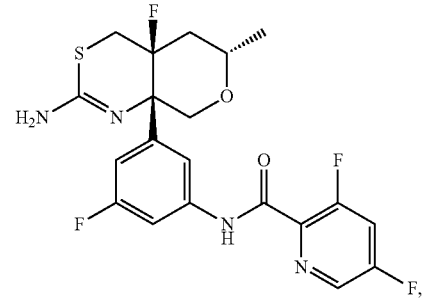
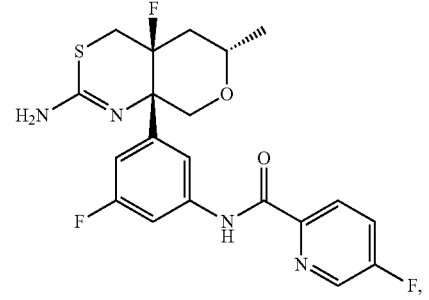 [SMILES: C[C@H]1C[C@@]2(F)CSC(N)=N[C@@]2(c2cccc(NC(=O)c3ccc(Cl)cn3)c2)CO1]
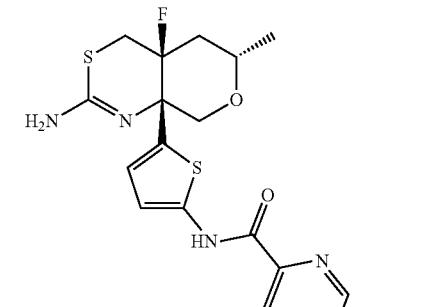
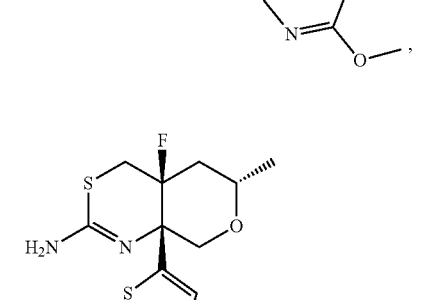
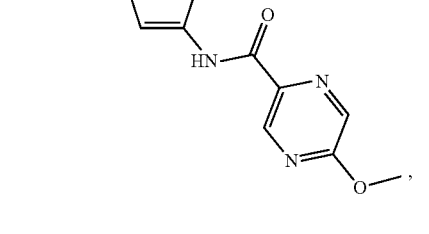

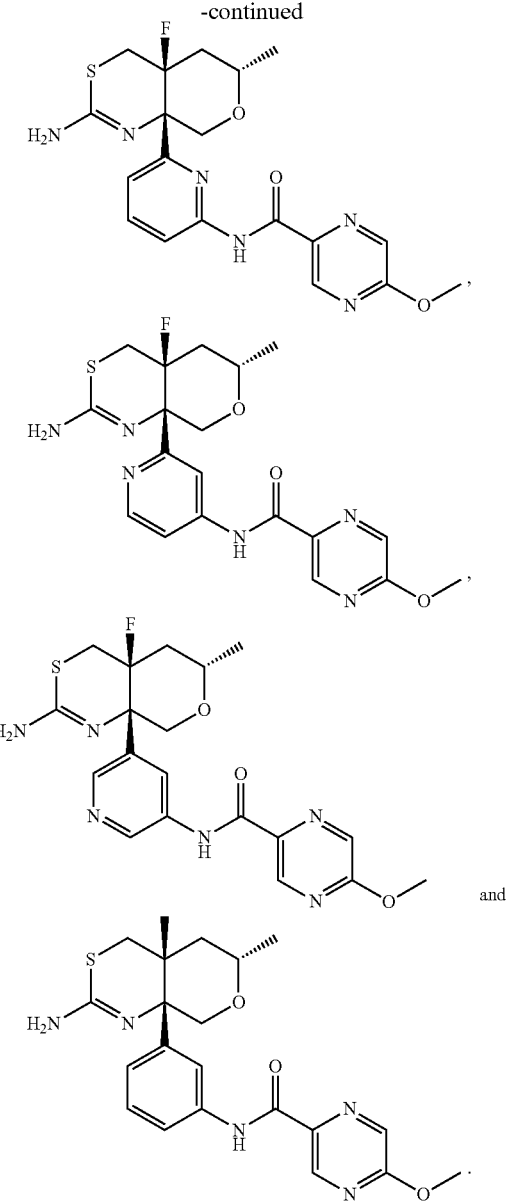

and

7. The compound according to claim 1, or a pharmaceutically acceptable salt, or stereoisomer thereof, said pharmaceutically acceptable salt is an inorganic acid salt or an organic acid salt of the compound; said inorganic acid salt is selected from the group consisting of hydrochloride, hydrobromate, hydriodate, sulfate, disulfate, nitrate, phosphate, and acid phosphate; said organic acid salt is selected from the group consisting of formate, acetate, trifluoroacetate, propionate, pyruvate, glycolate, oxalate, malonate, fumarate, maleate, lactate, malate, citrate, tartrate, methanesulfonate, ethanesulfonate, benzenesulfonate, salicylate, picrate, glutamate, ascorbate, camphorate, and camphorsulfonate.

8. A method for treatment of Alzheimer's disease, comprising administering to the subject the compound according to claim 1, or a pharmaceutically acceptable salt, or stereoisomer thereof.

9. A pharmaceutical composition comprising the compound according to claim 1, or a pharmaceutically acceptable salt, or stereoisomer thereof.

10. The compound according to claim 2, or a pharmaceutically acceptable salt, or stereoisomer thereof, in which A is phenyl, or phenyl substituted by 1~4 substituents, or 5~6 membered heteroaryl, or 5~6 membered heteroaryl substituted by 1~4 substituents; said substituents are optionally selected from the group consisting of halogen atom, amino, cyano, difluoromethyl, trifluoromethyl, trifluoromethoxyl, $C_{1-6}$ alkoxyl, $C_{1-6}$ alkyl, and $C_{1-6}$ alkylamino.

11. The compound according to claim 2, or a pharmaceutically acceptable salt, or stereoisomer thereof, in which L is a single bond, or oxygen atom, or —NH— or —NHCO—, or —NR$_5$SO$_2$—; B is 5~6 membered heteroaryl, or 5~6 membered heteroaryl substituted by 1~4 substituents; wherein, $R_5$ is hydrogen atom, or $C_{1-6}$ alkyl, or $C_{1-6}$ alkyl substituted by 1~3 substituents; said substituents are optionally selected from the group consisting of halogen atom, amino, cyano, difluoromethyl, trifluoromethyl, trifluoromethoxyl, $C_{1-6}$ alkoxyl, $C_{1-6}$ alkyl, $C_{2-6}$ alkynyl, and $C_{1-6}$ alkylamino.

12. The compound according to claim 2, or a pharmaceutically acceptable salt, or stereoisomer thereof, said pharmaceutically acceptable salt is an inorganic acid salt or an organic acid salt of the compound; said inorganic acid salt is selected from the group consisting of hydrochloride, hydrobromate, hydriodate, sulfate, disulfate, nitrate, phosphate, and acid phosphate; said organic acid salt is selected from the group consisting of formate, acetate, trifluoroacetate, propionate, pyruvate, glycolate, oxalate, malonate, fumarate, maleate, lactate, malate, citrate, tartrate, methanesulfonate, ethanesulfonate, benzenesulfonate, salicylate, picrate, glutamate, ascorbate, camphorate, and camphorsulfonate.

13. A method for treatment of Alzheimer's disease, comprising administering to the subject the compound according to claim 2, or a pharmaceutically acceptable salt, or stereoisomer thereof.

14. A pharmaceutical composition comprising the compound according to claim 2, or a pharmaceutically acceptable salt, or stereoisomer thereof.

* * * * *